(12) United States Patent
Gerner et al.

(10) Patent No.: US 10,655,183 B2
(45) Date of Patent: May 19, 2020

(54) CARCINOMA DIAGNOSIS AND TREATMENT BASED ON ODC1 GENOTYPE

(71) Applicant: THE ARIZONA BOARD OF REGENTS ON BEHALF OF THE UNIVERSITY OF ARIZONA, Tucson, AZ (US)

(72) Inventors: Eugene Gerner, Tucson, AZ (US); Patricia Thompson, Tucson, AZ (US); Tracy Brooks, Oxford, MS (US); Jenaro Garcia-Huidobro, Tucson, AZ (US)

(73) Assignee: ARIZONA BOARD OF REGENTS ON BEHALF OF UNIVERSITY OF ARIZONA, Tucson, AZ (US)

( * ) Notice: Subject to any disclaimer, the term of this patent is extended or adjusted under 35 U.S.C. 154(b) by 0 days.

(21) Appl. No.: 15/319,857

(22) PCT Filed: Jun. 18, 2014

(86) PCT No.: PCT/US2014/042979
§ 371 (c)(1),
(2) Date: Dec. 19, 2016

(87) PCT Pub. No.: WO2015/195120
PCT Pub. Date: Dec. 23, 2015

(65) Prior Publication Data
US 2017/0362658 A1    Dec. 21, 2017

(51) Int. Cl.
*C12Q 1/6886* (2018.01)
*A61K 31/192* (2006.01)
*A61K 31/198* (2006.01)

(52) U.S. Cl.
CPC .......... *C12Q 1/6886* (2013.01); *A61K 31/192* (2013.01); *A61K 31/198* (2013.01); *C12Q 2600/106* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 4,309,442 A | 1/1982 | Bey | |
| 4,330,559 A | 5/1982 | Bey et al. | |
| 4,413,141 A | 11/1983 | Bey et al. | |
| 4,499,072 A | 2/1985 | Sunkara | |
| 4,859,452 A | 8/1989 | Ajani et al. | |
| 4,925,835 A | 5/1990 | Heston | |
| 5,002,879 A | 3/1991 | Bowlin | |
| 5,814,625 A | 9/1998 | Larson et al. | |
| 5,843,929 A | 12/1998 | Larson et al. | |
| 6,258,845 B1 | 7/2001 | Gerner et al. | |
| 6,573,290 B1 | 6/2003 | Love | |
| 6,602,910 B2 | 8/2003 | Levenson | |
| 6,753,422 B2 | 6/2004 | O'Brien et al. | |
| 7,273,888 B2 | 9/2007 | Ramesh | |
| 7,592,319 B2 | 9/2009 | Li et al. | |
| 8,329,636 B2 | 12/2012 | Gerner et al. | |
| 9,072,778 B2 | 7/2015 | Bachmann | |
| 9,121,852 B2 | 9/2015 | Gerner et al. | |
| 9,937,141 B2 | 4/2018 | Gerner et al. | |
| 2002/0081611 A1 | 6/2002 | O'Brien | |
| 2002/0110590 A1 | 8/2002 | Shaked et al. | |
| 2005/0032726 A1 | 2/2005 | Li et al. | |
| 2005/0059690 A1 | 3/2005 | Newman et al. | |
| 2010/0197718 A1 | 8/2010 | Pisano et al. | |
| 2010/0317708 A1* | 12/2010 | Gerner ............. | A61K 31/192 514/406 |
| 2011/0256161 A1 | 10/2011 | Burns et al. | |
| 2012/0259013 A1 | 10/2012 | Motwani et al. | |
| 2013/0157972 A1 | 6/2013 | Cheng | |
| 2013/0164751 A1 | 6/2013 | Gerner et al. | |
| 2013/0216528 A1 | 8/2013 | Cheung et al. | |
| 2013/0217743 A1 | 8/2013 | Raj et al. | |
| 2015/0301060 A1 | 10/2015 | Gerner et al. | |
| 2016/0213634 A1 | 7/2016 | Gerner et al. | |

FOREIGN PATENT DOCUMENTS

| | | |
|---|---|---|
| CA | 2 165 481 | 1/1995 |
| EP | 2 438 919 | 4/2012 |
| JP | 2002-509884 | 4/2002 |

(Continued)

OTHER PUBLICATIONS

Sausville et al. (Cancer Research, 2006, vol. 66, pp. 3351-3354).*
Johnson et al. (British J. of Cancer, 2001, 84(10):1424-1431).*
Guo et al., Cancer Research 60, 6314-6317, 2000.*
"VANIQA®" (eflornithine hydrochloride) Prescription Information, dated Jul. 2010.
Alberts et al., "Do NSAIDs exert their colon cancer chemoprevention activities through the inhibition of mucosal prostaglandin synthetase?," *J. Cell. Biochem. Supp.*, (22):18-23, 1995.
Arber et al., "A K-ras oncogene increases resistance to sulindac-induces apoptosis in rat enterocytes", Gastroenterology, 113: 1892-1990, 1997.

(Continued)

*Primary Examiner* — Bong-Sook Baek
(74) *Attorney, Agent, or Firm* — Parker Highlander PLLC

(57) ABSTRACT

The present invention provides methods and kits a) for preventing and/or treating cancer (e.g., colorectal cancer, neuroblastoma) that is linked, in part, to high levels of ODC activity and increased cellular polyamine content, b) for predicting cancer patient survival, especially cancer patient's whose cancer is linked, in part, to high levels of ODC activity and increased cellular polyamine contents, and c) for selecting the corresponding treatment options for such patients based on the allelic nucleotide sequence or SNP at positions +263 and/or +316 of the ODC1 gene as well as cancer treatment methods, in each case, which include the determination of the ODC1 genotype at the +263 and/or +316 positions, as a means to guide treatment selection.

15 Claims, 21 Drawing Sheets
Specification includes a Sequence Listing.

(56) References Cited

FOREIGN PATENT DOCUMENTS

| | | |
|---|---|---|
| JP | 2012-511052 | 5/2012 |
| WO | WO 99/49859 | 10/1999 |
| WO | WO 01/68076 | 9/2001 |
| WO | WO 02/15895 | 2/2002 |
| WO | WO 2009/048932 | 4/2009 |
| WO | WO 2010/056919 | 5/2010 |
| WO | WO 2010/132817 | 11/2010 |
| WO | WO 2011/135459 | 11/2011 |
| WO | WO 2014/140072 | 9/2014 |
| WO | WO 2016/130918 | 8/2016 |
| WO | WO 2017/075576 | 5/2017 |

OTHER PUBLICATIONS

Babbar et al., "Induction of spermidine/spermine N1-acetyltransferase (SSAT) by aspirin in Caco-2 colon cancer cells," *Biochem. J.*, 394:317-24, 2006.

Bachrach et al., "Polyamines: new cues in cellular signal transduction," *News Physiol. Sci.*, 16:106-109, 2001.

Barry et al., "Ornithine decarboxylase polymorphism modification of response to aspirin treatment for colorectal adenoma prevention," *J. Natl. Cancer Inst.*, 98(20):1494-500, 2006.

Basuroy and Gerner, "Emerging concepts in targeting the polyamine metabolic pathway in epithelial cancer chemoprevention and chemotherapy," *J. Biochem.*, 139(1):27-33, 2006.

Bedi et al., "Inhibition of apoptosis during development of colorectal cancer," *Cancer Res.*, 55(9):1811-1816, 1995.

Bello-Fernandez et al., "The ornithine decarboxylase gene is a transcriptional target of c-Myc," *Proc. Natl. Acad. Sci. USA*, 90:7804-8, 1993.

Boolbol, et al., "Cyclooxygenase-2 overexpression and tumor formation are blocked by sulindac in a murine model of familial adenomatous polyposis," *Cancer Research*, 56:2556-2560, 1996.

Boone et al., "Biomarker end-points in cancer chemoprevention trails," *IARC Scientific Publications*, 142:273-280, 1997.

Boyle et al., "Polyamine contents in rectal and buccal mucosae in humans treated with oral difluoromethylornithine," *Cancer Epidemiol. Biomarkers Prev.*, 1:131-135, 1992.

Brabender et al., "Upregulation of ornithine decarboxylase mRNA expression in Barrett's esophagus and Barrett's-associated adenocarcinoma," *J. Gastrointest. Surg.*, 5:174-181; discussion 182, 2001.

Braverman et al., "Ornithine decarboxylase: an unreliable marker for the identification of population groups at risk for colonic neoplasia", *Am. J. Gastronenterology*, 85:723-726, 1990.

Childs et al., "Polyamine-dependent gene expression," *Cell. Molec. Life Sci.*, 60:1394-1406, 2003.

Croghan et al., "Dose-related alpha-difluoromethylornithine ototoxicity," *Am. J. Clin. Oncol.*, (14):331-5, 1991.

Derynck et al., "TGF-beta signaling in tumor suppression and cancer progression," *Nature Genetics*, 29:117-29, 2001.

DuBois et al., "G1 delay in cells overexpressing prostaglandin endoperoxide synthase-2," *Cancer Res.*, 56:733-737, 1996.

Erdman et al., "APC-dependent changes in expression of genes influencing polyamine metabolism, and consequences for gastrointestinal carcinogenesis, in the Min mouse," *Carcinogenesis*, 20(9):1709-13, 1999.

Extended European Search Report issued in European Patent Application No. 10775626.4, dated Feb. 4, 2013.

Fearon et al., "A genetic model for colorectal tumorigenesis," *Cell*, 61:759-767, 1990.

Fultz and Gerner, "APC-dependent regulation of ornithine decarboxylase in human colon tumor cells," *Mol. Carcinog.*, 34:10-8, 2002.

Gann et al., "Low-dose aspirin and incidence of colorectal tumors in a randomized trial," *J. Natl. Cancer Inst.*, 85:1220-1224, 1993.

Gerner and Meyskens, "Polyamines and cancer: old molecules, new understanding," *Nature Rev. Cancer*, 4:781-92, 2004.

Gerner et al., "Combination chemoprevention for colon cancer targeting polyamine synthesis and inflammation," *Clinical Cancer Research*, 15(3):758-761, 2009.

Gerner et al., "Gastrointestinal tissue polyamine contents of patients with Barrett's esophagus treated with alpha-difluoromethylornithine," *Cancer Epidemiol. Biomarkers Prev.*, 3:325-330, 1994.

Gerner, "Impact of dietary amino acids and polyamines on intestinal carcinogenesis and chemoprevention in mouse models," *Biochemical Society Transactions*, 35(2):322-325, 2007.

Giardiello et al., "Ornithine decarboxylase and polyamines in familial adenomatous polyposis," *Cancer Res.*, (57):199-201, 1997.

Greenberg et al., "Reduced risk of large-bowel adenomas among aspirin users," *J. Natl. Cancer Inst.*, 85:912-916, 1993.

Guo et al., "Functional analysis of human ornithine decarboxylase alleles," *Cancer Res.*, 60(22):6314-6317, 2000.

Hanif et al., "Effects of nonsteroidal anti-inflammatory drugs on proliferation and on induction of apoptosis in colon cancer cells by a prostaglandin-independent pathway," *Biochemical Pharmacology*, (52):237-245, 1996.

Hessels et al., "Microbial flora in the gastrointestinal tract abolishes cytostatic effects of α-difluoromethylornithine in vivo," *Int. J. Cancer*, 43: 1155-1164, 1989.

Hixson et al., "Ornithine decarboxylase and polyamines in colorectal neoplasia and mucosa," *Cancer Epidemiology Biomarkers Prev.*, 2:369-374, 1993.

Hixson et al., "Sources of variability in measurements of ornithine decarboxylase activity and polyamine contents in colorectal mucosa," *Cancer Epidemoil. Biomarkers Prev.*, 3:317-323, 1994.

Hubner et al., "Ornithine decarboxylase G316A genotype is prognostic for colorectal adenoma recurrence and predicts efficacy of aspirin chemoprevention," *Clin. Cancer Res.*, 14(8):2303-9, 2008.

Hughes, et al., "Polyamines reverse non-steroidal anti-inflammatory drug-induced toxicity in human colorectal cancer cells", *Biochem J*, 374:481-8, 2003.

Ignatenko et al., "Dietary putrescine reduces the intestinal anticarcinogenic activity of sulindac in a murine model of familial adenomatous polyposis," Nutrition and Cancer, 56(2): 172-181, 2006.

Ignatenko et al., "Role of c-Myc in intestinal tumorigenesis of the ApcMin/+ mouse," *Cancer Biol. Ther.*, 5(12):1658-64, 2006.

Iwamoto et al., "Expression of beta-catenin and full-length APC protein in normal and neoplastic colonic tissues," *Carcinogenesis*, 21:1935-40, 2000.

Jass et al., "Emerging concepts in colorectal neoplasia," *Gastroenterology*, 123:862-876, 2002.

Kawamori, et al., "Chemopreventive activity of celecoxib, a specific cyclooxygenase-2 inhibitor, against colon carcinogenesis," *Cancer Research*, 58:409-412, 1998.

Kelloff et al., "Chemopreventive drug development: perspectives and progress," Cancer Epidemiology Biomarks and Prevention, 3:85-98, 1994.

Kelloff et al., "New agents for cancer chemoprevention," *J. Cell. Biochem.*, 265:1-28, 1996.

Kelloff et al., "Perspectives on chemoprevention agent selection and short term clinical prevention trials," European J. Cancer Prevention, 5(Supp. 2):79-85, 1996.

Kingsnorth et al., "Effects of alpha-difluoromethylornithine and 5-fluorouracil on the proliferation of a human colon adenocarcinoma cell line," *Cancer Res.*, 43(9):4035-8, 1983.

Kruh et al., "Expression Pattern of MRP in Human Tissues and Adult Solid Tumor Cell Lines," *J. Natl. Cancer Inst.*, 87(16):1256-1258, 1995.

Ladenheim et al., "Effect of sulindac on sporadic colonic polyps," *Gastroenterology*, 108:1083-1087, 1995.

Lanza et al., "Peptic ulcer and gastrointestinal hemorrhage associated with nonsteroidal anti-inflammatory drug use in patients younger than 65 years. A large health maintenance organization cohort study," *Arch. Intern. Med.*, 155:1371-1377, 1995.

Le et al., "Effects of socioeconomic status and treatment disparities in colorectal cancer survival," *Cancer Epidemiol. Biomarkers Prev.*, 17:1950-62, 2008.

Levin et al., "Relationship between ornithine decarboxylase levels in anaplastic gliomas and progression-free survival in patients

(56) References Cited

OTHER PUBLICATIONS treated with DFMO-PCV chemotherapy," *International Journal of Cancer*, 121:(10): 2279-2283, 2010.

Linsalata et al., "Nutritional factors and polyamine metabolism in colorectal cancer," *Nutrition*, 24:382-389, 2008.

Lipkin, "New rodent models for studies of chemopreventive agents," *J. Cell Biochem. Suppl.*, 28-29:144-7, 1997.

Love et al., "Randomized phase I chemoprevention dose-seeking study of alpha-difluoromethylornithine," *J. Natl. Cancer Inst.*, 85:732-7, 1993.

Luk and Baylin, "Ornithine decarboxylase as a biologic marker in familial colonic polyposis," *N. Engl. J. Med.*, 311(2):80-83, 1984.

Lupulescu, "Control of precancer cell transformation into cancer cells: its relevance to cancer prevention," *Cancer Detect. Prev.*, 20(6):634-637, 1996.

Martinez et al., "Pronounced reduction in adenoma recurrence associated with aspirin use and a polymorphism in the ornithine decarboxylase gene," *Proc. Natl. Acad. Sci. USA*, 100:7859-64, 2003.

Matsubara et al., "Association between high levels of ornithine decarboxylase activity and favorable prognosis in human colorectal carcinoma," *Clinical Cancer Res.*, 1:665-71, 1995.

McGarrity et al., "Colonic polyamine content and ornithine decarboxylase activity as markers for adenomas," *Cancer*, 66:1539-1543, 1990.

McLaren et al., "Longitudinal assessment of air conduction audiograms in a phase III clinical trial of difluoromethylornithine and sulindac for prevention of sporadic colorectal adenomas," *Cancer Prev. Res.*, 1(7):514-21, 2008.

Meyskens and Gerner, "Development of difluoromethylornithine as a chemoprevention agent for the management of colon cancer," *J. Cell. Biochem.*, 22:126-131, 1995.

Meyskens et al., "Development of difluoromethylornithine (DFMO) as a chemoprevention agent," *Clin. Cancer Res.*, 5:945-951, 1999.

Meyskens et al., "Difluoromethylornithine plus sulindac for the prevention of sporadic colorectal adenomas: a randomized placebo-controlled, double-blind trial," *Cancer Prev. Res.*, 1(1):32-8, 2008.

Meyskens et al., "Dose de-escalation chemoprevention trial of alpha-difluoromethylornithine in patients with colon polyps," *J. Natl. Cancer Inst.*, 86(15):1122-1130, 1994.

Meyskens et al., "Effect of alpha-difluoromethylornithine on rectal mucosal levels of polyamines in a randomized, double-blinded trial for colon cancer prevention," *J. Natl. Cancer Inst.*, 90(16):1212-8, 1998.

Muscat et al., "Nonsteroidal antiinflammatory drugs and colorectal cancer," *Cancer*, 74:1847-1854, 1994.

O'Brien et al., "Differences in ornithine decarboxylase and androgen receptor allele frequencies among ethnic groups," *Molec. Carcinog.*, 41(2):120-3, 2004.

Office Action, issued in Chinese Application No. 201080031983.5, dated Apr. 14, 2014.

Office Action, issued in Chinese Application No. 201080031983.5, dated Dec. 31, 2014.

Office Communication issued in U.S. Appl. No. 12/780,592, dated Mar. 20, 2012.

Office Communication, issued in U.S. Appl. No. 13/697,984, dated Jul. 1, 2014.

Pardali and Moustakas, "Actions of TGF-beta as tumor suppressor and pro-metastatic factor in human cancer," *Biochimica et Biophysica Acta*, 1775:21-62, 2007.

Pasricha et al., "The effects of sulindac on colorectal proliferation and apoptosis in familial adenomatous polyposis," *Gastroenterology*, 109:994-998, 1995.

Paz et al., "Plyamines are oncometabolites that regulate the LIN28/let-7 pathway in colorectal cancer cells," *Molecular Carcinogensis*, 2013.

PCT International Search Report and Written Opinion, issued in International application No. PCT/US10/34974, dated Jul. 2, 2010.

PCT International Search Report and Written Opinion, issued in International Application No. PCT/US2011/036464, dated Jan. 19, 2012.

PCT International Search Report and Written Opinion, issued in International Application No. PCT/US2013/067305, dated Jan. 2, 2014.

PCT International Search Report and Written Opinion, issued in International Application No. PCT/US2014/042979, dated Jan. 29, 2015.

Peel et al., "Characterization of hereditary nonpolyposis colorectal cancer families from a population-based series of cases," *J. Natl. Cancer Inst.*, 92:1517-22, 2000.

Pegg, "Recent advances in the biochemistry of polyamines in eukaryotes," *Biochem.*, 234(2):249-262, 1986.

Piazza et al., "Antineoplastic drugs sulindac sulfide and sulfone inhibit cell growth by inducing apoptosis," *Cancer Res.*, (55):3110-3116, 1995.

Piazza et al., "Apoptosis primarily accounts for the growth-inhibitory properties of sulindac metabolites and involves a mechanism that is independent of cyclooxygenase inhibition, cell cycle arrest, and p53 induction," *Cancer Res.*, (57):2452-2459, 1997a.

Piazza et al., "Sulindac sulfone inhibits azoxymethane-induced colon carcinogenesis in rats without reducing prostaglandin levels," *Cancer Res.*, (57):2909-2915, 1997b.

Pollard and Luckert, "Prevention and treatment of primary intestinal tumors in rats by piroxicam," *Cancer Res.*, 49:6471-6473, 1989.

Porter et al., "Polyamine biosynthetic activity in normal and neoplastic human colorectal tissue," Cancer, 60:1275-1281, 1987.

Quemener et al., "Polyamine deprivation: a new tool in cancer treatment", *Institute of Anticancer Research*, 14:443-448, 1994.

Raj et al., "Role of dietary polyamines in a phase III clinical trial of difluoromethylornithine (DFMO) and sulindac for prevention of sporadic colorectal adenomas", *British Journal of Cancer*, 108(3):512-518, 2013.

Rao et al., "Chemoprevention of colon carcinogenesis by sulindac, a nonsteroidal anti-inflammatory agent," *Cancer Res.*, (55):1464-1472, 1995.

Reddy et al., "Chemoprevention of colon carcinogenesis by concurrent administration of piroxicam, a nonsteroidal antiinflammatory drug with D,L-alpha-difluoromethylornithine, an ornithine decarboxylase inhibitor, in diet," *Cancer Research*, 50:2562-2568, 1990.

Reddy et al., "Dose-related inhibition of colon carcinogenesis by dietary piroxicam, a nonsteroidal antiinflammatory drug, during different stages of rat colon tumor development," *Cancer Res.*, 47:5340-5346, 1987.

Roberts and Wakefield, "The two faces of transforming growth factor beta in carcinogenesis," *Proc. Natl. Acad. Sci. USA*, 100:8621-3, 2003.

Samaha et al., "Modulation of apopotsoi by sulindac, curcumin, phenylethyl-3-methylcaffeate, and 6-phenylhexyl isothiocyanate, apoptotic index as a biomarker in colon and cancer chemoprevention promotion," Cancer Res., (57):1301-1305, 1997.

Seiler and Knodgen, "High-performance liquid chromatographic procedure for the simultaneous determination of the natural polyamines and their monoacetyl derivatives," *J.Chromatogr.*, 221(2):227-235, 1980.

Seiler et al., "Endogenous and exogenous polyamines in support of tumor growth", *Cancer Research*, 50:5077-5083, 1990.

Simoneau et al., "Alpha-difluoromethylornithine and polyamine levels in the human prostate: results of a phase IIa trial," *J. Natl. Cancer Inst.*, 93:57-9, 2001.

Simoneau et al., "The effect of difluoromethylornithine on decreasing prostate size and polyamines in men: results of a year-long phase IIb randomized placebo-controlled chemoprevention trial," *Cancer Epidemiol. Biomarkers Prev.*, 17:292-9, 2008.

Singh and Reddy, "Molecular markers in chemoprevention of colon cancer. Inhibition of expression of ras-p21 and p53 by sulindac during azoxymethane-induced colon carcinogenesis," *Annals. NY Acad. Sci.*, (768):205-209, 1995.

(56) References Cited

OTHER PUBLICATIONS

Singh et al., "*Bifidobacterium longum*, a lactic acid-producing intestinal bacterium inhibits colon cancer and modulates the intermediate biomarkers of colon carcinogenesis," *Carcinogenesis*, 18:833-841, 1997.
Singh et al., "Modulation of azoxymethane-induced mutational activation of ras protooncogenes by chemopreventive agents in colon carcinogenesis," *Carcinogenesis*, (15):1317-1323, 1994.
Smithson et al., "Discovery of potent and selective inhibitors of Trypanosoma brucei ornithine decarboxylase," The Journal of Biological Chemistry, 265(22):16771-16781, 2010.
Soda et al., "Polyamine-rich food decreases age-associated pathology and mortality in aged mice," Experimental Gerontology, 44: 727-732, 2009.
Su et al., "Multiple intestinal neoplasia caused by a mutation in the murine homolog of the APC gene," Science, (256):668-670, 1992.
Supplementary European Search Report issued in European Application No. 11 78 1359, dated Nov. 5, 2013.
Tabib et al., "Role of polyamines in mediating malignant transformation and oncogene expression," *Int. J. Biochem. Cell. Biol.*, 31:1289-1295, 1999.
Tempero et al., "Chemoprevention of mouse colon tumors with difluoromethylornithine during and after carcinogen treatment," *Cancer Res.*, 49(21):5793-7, 1989.
Thomas and Thomas, "Polyamine metabolism and cancer," *J. Cell Mol. Med.*, 7:113-26, 2003.
Thompson et al., "Inhibition of mammary carcinogenesis by sulfone metabolite of sulindac," J. Natl. Cancer Inst., (87):125-1260, 1995.
Thompson et al., "Levels of rectal mucosal polyamines and prostaglandin E2 predict ability of DFMO and sulindac to prevent colorectal adenoma," *Gastroenterology*, 139(3): 797-805, 2010.
Thompson, et al., "Sulfone metabolite of sulindac inhibits mammary carcinogenesis", Cancer Research, 57:267-271, 1997.
Vane and Botting, "Mechanism of action of anti-inflammatory drugs," *Scand. J. Rheumatol.*, 25(Suppl. 102):9-21, 1996.
Visvanathan et al., "Association among an ornithine decarboxylase polymorphism, androgen receptor gene (CAG) repeat length and prostate cancer risk," *J. Urol.*, 171(2 Pt 1):652-5, 2004.
Wallace and Caslake, "Polyamines and colon cancer," Eur J Gastroenterol Helatol., 13(9): 1033-1039, 2001.
Wallace, "The physiological role of the polyamines," *Eur. J. Clin. Invest.*, 30:1-3, 2000.
Wang et al., "Mucosal polyamine measurements and colorectal cancer risk," *J. Cell. Biochem.*, 63:252-257, 1996.
Zell et al., "Associations of a polymorphism in the ornithine decarboxylase gene with colorectal cancer survival," *Clin. Cancer Res.*, 15(19):6208-16, 2009.
Zell et al., "*Ornithine decarboxylase (ODC)*-1 gene polymorphism effects on baseline tissue polyamine levels and adenoma recurrence in a randomized phase III adenoma prevention trial of DFMO+ sulindac versus placebo," *J. Clin. Oncol.*, 26(15S):Abstract 1502, 2008.
Zell et al., "Ornithine decarboxylase-1 polymorphism, chemoprevention with eflornithine and sulindac, and outcomes among colorectal adenoma patients," *J. Natl. Cancer Inst.*, 102(19):1513-1516, 2010.
Zell et al., "Risk and risk reduction involving arginine intake and meat consumption in colorectal tumorigenesis and survival," *Intl. J. Cancer*, 120:459-68, 2007.
Zell et al., "Risk of cardiovascular events in a randomized placebo-controlled, double-blind trial of difluoromethylornithine plus sulindac for the prevention of sporadic colorectal adenomas," *Cancer Prev. Res.*, 2(3):209-12, 2009.
Zell et al., "Survival after colorectal cancer diagnosis is associated with colorectal cancer family history," *Cancer Epidemiol. Biomarkers Prev.*, 17:3134-40, 2008.
Ziogas and Anton-Culver, "Validation of family history data in cancer family registries," *Am. J. Prev. Med.*, 24:190-8, 2003.
Zoumas-Morse et al., "Development of a polyamine database for assessing dietary intake," *J. Am. Diet. Assoc.*, 107:1024-1027, 2007.

Lozier, Ann M., et al. "Targeting ornithine decarboxylase reverses the LIN28/Let-7 axis and inhibits glycolytic metabolism in neuroblastoma." *Oncotarget* 6.1 (2015): 196.
Mackenzie, Gerardo G., et al. "Phospho-sulindac (OXT-328) combined with difluoromethylornithine prevents colon cancer in mice." *Cancer prevention research* 4.7 (2011): 1052-1060.
Office Communication issued in Japanese Patent Application No. 2016-574003, dated Feb. 20, 2018. English Translation.
Rial, Nathaniel S., Frank L. Meyskens, and Eugene W. Gerner. "Polyamines as mediators of APC-dependent intestinal carcinogenesis and cancer chemoprevention." *Essays in biochemistry* 46 (2009): 111-124.
Castel et al., "Treatment of high-risk neuroblastoma with anti-GD2 antibodies," Clinical and Translational Oncology, 12:788-793, 2010.
Erdman et al., "Assessment of Mutations in Ki-ras and P53 in colon cancers from azoxymethane- and dimethylhydrazine-treated rats," Mol. Carcin., (19):137-144, 1997.
Gamble et al., "Polyamine pathway inhibition as a novel therapeutic approach to treating neuroblastoma," Frontier in Oncology, 2(162):1-10, 2012.
Gerner, E. W., et al. "Rationale for, and design of, a clinical trial targeting polyamine metabolism for colon cancer chemoprevention." *Amino acids* 33.2 (2007): 189-195.
Goodeve, A. C., P. H. Reitsma, and J. H. McVey. "Nomenclature of genetic variants in hemostasis." *Journal of Thrombosis and Haemostasis* 9.4 (2011): 852-855.
Hogarty et al., "ODC1 is a critical determinant of MYCN oncogenesis and a therapeutic target in neuroblastoma," Cancer Res., 68:9735-9745, 2008.
Nishimura et al., "Independent roles of eIF5A and polyamines in cell proliferation," Biochem. J., 385:779-785, 2005.
Office Communication issued in U.S. Appl. No. 12/780,592, dated Aug. 14, 2012.
Office Communication issued in U.S. Appl. No. 13/709,753, dated Sep. 10, 2014.
Office Communication issued in U.S. Appl. No. 13/709,753, dated Apr. 21, 2015.
Office Communication issued in U.S. Appl. No. 14/841,750, dated Apr. 21, 2017.
Office Communication issued in U.S. Appl. No. 14/841,750, dated Nov. 24, 2017.
Office Communication issued in U.S. Appl. No. 13/697,984, dated Feb. 11, 2014.
Office Communication issued in U.S. Appl. No. 13/697,984, dated Apr. 22, 2015.
Office Communication issued in U.S. Appl. No. 13/697,984, dated Jul. 28, 2016.
Office Communication issued in U.S. Appl. No. 13/697,984, dated May 22, 2017.
Office Communication issued in Japanese Patent Application No. 2016-574003, dated Dec. 11, 2018. English Translation.
Rounbehler et al., "Targeting ornithine decarboxylase impairs development of MYCN-amplified neuroblastoma," Cancer Res., 69:547-553, 2009.
Saletta et al., "Molecular profiling of childhood cancer: Biomarkers and novel therapies," BBA Clinical, 1:59-77, 2014.
Samal et al., "AMXT-1501, a novel polyamine transport inhibitor, synergizes with DFMO in inhibiting neuroblastoma cell proliferation by targeting both ornithine decarboxylase and polyamine transport," Int. J. Cancer, 133:1323-1334, 2013.
Sholler, Giselle L. Saulnier, et al. "A phase I trial of DFMO targeting polyamine addiction in patients with relapsed/refractory neuroblastoma." *PLoS One* 10.5 (2015): e0127246.
Sholler et al., [abstract]. In: Proceedings of the 104th Annual Meeting of the American Association for Cancer Research; Apr. 6-10, 2013; Washington, DC. Philadelphia (PA): AACR; Cancer Res 2013;73(8 Suppl):Abstract nr LB-179. doi:10.1158/1538-7445.
Silva et al., "Role of peripheral polyamines in the development of inflammatory pain," Biochemical Pharmacology, 82:269-277, 2011.
Vargas et al., "Dietary Polyamine intake and polyamines measured in urine," Nutrition and Cancer, 66(7): 1144-1153, 2014.

(56) References Cited

OTHER PUBLICATIONS

Zeng, G. X., et al. "New concept and clinical application of colorectal intraepithelial neoplasia and carcinoma." Zhonghua wai ke za zhi [Chinese journal of surgery] 45.7 (2007): 449-451.

* cited by examiner

*Cell lines genotype*

| | ODC1 SNP | |
|---|---|---|
| | +263 | +316 |
| HT29 | GG | GA |
| HCT116 | GT | GG |

*Proteins expression*

SEQUENCE LISTING

```
<160> NUMBER OF SEQ ID NOS: 5

<210> SEQ ID NO 1
<211> LENGTH: 58
<212> TYPE: DNA
<213> ORGANISM: Artificial Sequence
<220> FEATURE:
<223> OTHER INFORMATION: Synthetic nucleic acid

<400> SEQUENCE: 1
ggagggaggg agcgagggcg ggagccgggg cgggctgcgg gccccgggcc ccgggcac      58

<210> SEQ ID NO 2
<211> LENGTH: 58
<212> TYPE: DNA
<213> ORGANISM: Artificial Sequence
<220> FEATURE:
<223> OTHER INFORMATION: Synthetic nucleic acid

<400> SEQUENCE: 2
gaagggaggg agcgagggcg ggagccgggg ctggctgcgg gccccgggcc ccgggcac      58

<210> SEQ ID NO 3
<211> LENGTH: 8184
<212> TYPE: DNA
<213> ORGANISM: Homo sapiens

<400> SEQUENCE: 3
gaagccgggg gcgggggcca cgcgtggggc aggcggtgct cggctcggct gacgtcggcc      60
```

-continued

```
cgccggcgcc ccaccagctc cgcgcgggcc cgggttggcc accgccgggc ccccgcccct    120
cccccggcgg tgtcccggcc ggaaccgatc gtggctggtt tgagctggtg cgtctccatg    180
gcgacccgcc ggtgctataa gtagggagcg gcgtgccgtg gggctttgtc agtccctcct    240
gtagccgccg ccgccgccgc ccgccgcccc tctgccagca gctccggcgc cacctcgggc    300
cggcgtctcc ggcgggcggg agccaggcgc tgacgggcgc ggcggggcg gccgagcgct    360 cctgcgcgctg cgactcaggc tccggcgtct gcgcttcccc atggggctgg cctgcgcgc    420 ctgggcgctc tgaggtgagg gactccccgg ccgcggagga agggagggag cgagggcggg    480
agccggggcg ggctgcgggc cccgggcccc gggcacgtgt gcggcgcgcc tcgccggcct    540
gcggagacac gtggtcgccg agcgggccac gaccttgagg cgccgcttcc tcccggcccg    600
gggttctccc gcggctggat aagggtgatc cgggcgcctc gttctgcccc cgtcttcaca    660
gctcggggct ggaggggcct aggggagacc cacccggaga ccctgcggcc ccgcgccggc    720
ctctttccca acccttcggc ggccgcgcgc tggccgggga gccgttgggg aggccctggc    780
ggccgcgcag caggtgcagg ggcgcagagc ccgggctcgc cttggtacag acgagcgggc    840 cccgccttg gcgccttcag tttccttcca gttttttattt tcgctgtgtc tacagagcag    900
atgacaccaa tttggaaacc cgcgagagtg ggtagagcta agatagtctt gctgtagtag    960
ctgtgatatt agatgctcgg ccatgactta gaggtgttta tttaaggact gtgaatgact   1020
cggtgatttc ggaaaagctt ggcttagatg aacggacata cacaggggag acagccctaa   1080
ggtttgcaga aaaggctgat tgtgctgttt gcgaagtcga ataattggt gaaagtgtag    1140 aaggcagaac ctctcaggaa tgtctgggga ggacaaagaa tgtgttggct gactttgttt   1200
aaacataaaa ttgggcagac tttaattgat ttgtgaaatt ttttttcaaag tttgtttgaa   1260 ttagccccta tctcttctaa cattatcctc ttgtgctaat tgattgacca ttttaaataa   1320
cttagctgtt acagaaagac cgaaaggtgt tcttcagtaa aatatattca gtaagttac    1380 ttaagtaacg ccttaaaaga tacagaaaag caaaaaagta ttggcgtatt aaaaagaaat   1440
caaaactttc caagtttagg cctgaacatt gccttaaaaa tatttaataa ggcctcaaat   1500
gacccagtcc gagactgcat gagcctattt attattaaat tgtaaatatt cttcatataa   1560
acaaaaatat ataaccatgt ctgtaacaaa aatggttttg ctagcgttgt tactctcttc   1620
ccttctccga ggggtgattt aggcaacttc ggaggttgac aatgccaagc agtcacaata   1680
gatagagctt taaagcaaat tctatgcatg ggtttggatt tatgacaggc ccgtcaccct   1740
gggcctgtca tagtaccccca tgccagagca aactgtgtcc ccgaaccatt gcctggcctc   1800
tgtgcccgta ggctgctggc actgaagtgg gttgcacagt ggaaaagaag aaagctctac   1860
ctggcagaaa ttttttaaagg ttaaaataaa taatttaag aaagctggtt cacaaggtgc   1920
cacatttgat gaaagcaaaa tacagtggct tttattgtta ctagagtgat gttcttgctt   1980 gttttttcttt tttggtgaag ttagccccaa attattctca tagctaagca aatacgagag   2040
tgactgtaag gacagttggc attcccggaa ttgctaaact tggtaggcaa cgctggttta   2100
agaatactga gttctagccg ggcgtggtgg ctcacgcctg taatcccaac actttgggag   2160
gctgaggcag gcggatcacc tgaggtcggg agttggagac cagcctgact aacatggaga   2220
aacgccatct ccactaaaaa tataaaatta gccaggcccc gggtgtggtg gcacatgccg   2280
gtaatcccag ctactcggga gactgaggca ggagaatcgc ttgaacccag gaggcggagg   2340
ttgaggtgag ccgagatcat gccattgcac tccagcctgg gcaacaagag taaaactctg   2400
```

```
tctcaaaaaa aaaaaaaaaa aatactgaat tctgatcagg taacagcaac tgtaatacaa      2460
tgtgataagt tgacttgaag attacagttt ttaagaagta tatcccagc taatacatga       2520 aaattaactc gtaaaatctc aaatgctcca gacatttcca tgatgcctgt tggtcagtaa      2580
aaatcattct aagacttagt ggaagtagga aatgtttgta tggctgtgta taaaggctat      2640
aatgtaatcc cagcactttg aagaccgag gcgggtggat cacctggggt caggagtttg       2700
agacccacct ggacaacgtg gtgaaatcct gtctctacta aaaacacaaa aattagccgg      2760
gcatggtggc aggcgcctgt aatcccagct gctggggagg ctgaggcagg agaatcgctt     2820
gaacccggga ggcagaggtt gcagtgagcc aagattgcac cgctgcactc cagcctgggt     2880
gacagcgtga gactctgtct caaaaaaaat aaaaagtct ataatgctat tttaagtttc       2940
taaggaactg aaactgctct gaaataaatc agaccattat aagactttt tccatatcag       3000 tgagctaagt gcagataagc ttctgaaact tgcatgctag attttttgg tacaaatatt       3060 tgaaatgctt agtgtgctgc cttggaaaaa cctggtattt tttgttgtgt ccttatactg      3120
ccaaggttta tggaatcatg taccttatgc ctagtaataa ttaggatgac caggccagtg     3180
agtggttcat atccggggca tgattagctc tgcgtgtgct cagccagtgc cccatcttca     3240
actcgatgtg ttcctaaggt agacagcaaa ttccctattt tatttctcag attgtcactg      3300
ctgttccaag ggcacacgca gagggatttg gaattcctgg agagttgcct ttgtgagaag     3360
ctggaaatat ttcttcaat tccatctctt agttttccat gtaagtattc agtttacatt       3420
tatgttgcag gttaatctta agaattgtat tgctaaggct tctaagtgaa tttctccact      3480
ctatttgcat tttgttgcat ttcagaggaa catcaagaaa tcatgaacaa ctttggtaat      3540
gaagagtttg actgccactt cctcgatgaa ggttttactg ccaaggacat tctggaccag     3600
aaaattaatg aagtttcttc ttctgtaagt atatgaggcc catgctggca gtgcagctga     3660
gagtgccagg caagtggaaa actttggcaa ggtctaagga agagcaatga ggcttacatg    3720
tcttgttatg gaatgtagaa attaattcac tggtggtaaa ttaatagtga taatggtgat    3780
actcatatca gtggctagac tcaaagagc aggattcatt gtgactgatg ggaatgaagg     3840
tcgctggcta ttggtgtggt gtgtggtgag gctgctagtg agtcacctgt gaccactctt    3900 gttcaggat gataaggatg ccttctatgt ggcagacctg ggagacattc taagaaaaca     3960
tctgaggtgg ttaaaagctc tccctcgtgt cacccccttt tatgcagtca aatgtaatga    4020
tagcaaagcc atcgtgaaga cccttgctgc taccgggaca ggattgact gtgctagcaa     4080 ggtaagcgat agcagcaggc ctcaaaagcg ttgtataaaa tgggcctggt attccccacg     4140
aggcagatac aagttgtgtt ttttgggcaa taaatgctca ctaaaggcaa atggggcggg    4200
ggggtacatg acaacttccc atgcttttct gtttattcca cgtgttaagc cacatatgga    4260
tagcatgaca ccactcttct ttttcagact gaaatacagt tggtgcagag tctgggggtg    4320
cctccagaga ggattatcta tgcaaatcct tgtaaacaag tatctcaaat taagtatgct    4380
gctaataatg gagtccagat gatgactttt gatagtgaag ttgagttgat gaaagttgcc    4440
agagcacatc ccaaagcaaa gtgagttatt ccccatctg agggcaagat cgggagcata    4500
agatatgtgg attcttatca aacaaactta aatttctgat tattatatt ctatacttta     4560 gtagaaagta gttgaaaccc ccattgagtc atgaagcctg ggactcaaac tacagaatat    4620
atcagcgaca gtatttagaa caggattgtt tttattttaa ttgtggctat aagtgaacat    4680
ctatcatgag acatttgctg cactttcctt gcttgtaggt tggttttgcg gattgccact   4740
gatgattcca aagcagtctg tcgtctcagt gtgaaattcg gtgccacgct cagaaccagc   4800
```

```
aggctccttt tggaacgggc gaaagagcta aatatcgatg ttgttggtgt caggtgagat    4860
tttggtggga tagctagagg tcaagacatt gaacagtttg agtttttacag gctttctcct   4920 agtgtttgct attattttaa gaaatactaa gacacagtgt ctcgtctctt tattttaccc    4980
cagcttccat gtaggaagcg gctgtaccga tcctgagacc ttcgtgcagg caatctctga    5040
tgcccgctgt gttttttgaca tgggggtgag tatacgtgac cctgttaggg aagggcggga   5100
cacaactgac aataactagt cttaattcta gagttaactt tttatggcag ttggttctgt    5160
attacatggg tttcagccta tctgctgcat acattttttgt tattagctgt ggatctggct   5220
gacttatttt cttgattcta ggctgaggtt ggtttcagca tgtatctgct tgatattggc    5280
ggtggctttc ctggatctga ggatgtgaaa cttaaatttg aagaggtaat ttagaacaaa    5340
actgtaatac tcagtagccg ttctaataaa ttccttttg gaatatttca aaatttaagt     5400
gtcttaacta ataccacaat gggctgaagt gtcttggtgt gatatttttga gtgatttctt   5460 tgtgctgtct gacattacac ttgataccat ttggtttttct aaagtgtgaa tcagctttcc   5520
cagaagtctt ggataattgg ttacattgga aatcatggct cacacctgta atccagcact    5580
tggggaggcc aaggtggtag gatcacttga gcccaggagt ttgagaccag cctgggcaac    5640
acagtgagac cccatctcta caaaaaaaat tttaaaatta gcctggtgtg gtggcgggca    5700
cctgtaatcc cagctacttg gaaggctgag gtgggaggat cacttgagcc caggaggttg    5760
aggctgcagt gagccatgat catgccactg cactcagcct gggctacaga gtgagaccct    5820
gtctcaaaaa aaaaaagaa aaagcatgtt gctgtgggct tcctagagaa tatgctgact     5880
gtagcacatc atcaccccaa atgtgctttg ctagacctat gcttcctctc cttaaaatac    5940
ttgaaatgtt tagtcactta ggaagttaag ccattatatt ggtgcttgaa tttataaaat    6000
atatccacat ggtttgttaa aatcatgacg taggcagaat aggattttta tcctgttggc    6060
atgtatttgt taaaatgttt tgacatcttg atgccttcct aggtagtagt tagttgcgta    6120
ctgttctttg ataaaaatca tacccataac atcctaaagg atatagggtg cctggagggg    6180
aatgaaaacg agccacctgg gatatgtagc ctggttttca gggagatgtt gatgttttt     6240 tgcttttgtt actttaatga taaacctgtc tgttgatgcc tggtctcatg atgtcatgtc    6300
acaaggccct gtgatgttac tccccatgt gaatttccca caatgaaggc tgctctttct     6360
tttctgtttc actctcttag atcaccggcg taatcaaccc agcgttggac aaatactttc    6420
cgtcagactc tggagtgaga atcatagctg agcccggcag atactatgtt gcatcagctt    6480
tcacgcttgc agtaatatc attgccaaga aaattgtatt aaaggaacag acgggctctg     6540
atggtatgta taaaggacga atcacttcat gtataactga agctgatgc aaaaagtcat     6600 taagattgtt gatctgcctt tctagacgaa gatgagtcga gtgagcagac ctttatgtat    6660
tatgtgaatg atggcgtcta tggatcatt aattgcatac tctatgacca cgcacatgta     6720
aagccccttc tgcaaaaggt aatttctgag catactgtat aaaacaatta agaggactgg    6780
tcacaacacg tgtaattaag tagtacttcc tctctccgtc tctttatata gagacctaaa    6840
ccagatgaga agtattattc atccagcata tggggaccaa catgtgatgg cctcgatcgg    6900
attgttgagc gctgtgacct gcctgaaatg catgtgggtg attggatgct ctttgaaaac    6960
atgggcgctt acactgttgc tgctgcctct acgttcaatg gcttccagag gccgacgatc    7020
tactatgtga tgtcagggcc tgcgtggtaa gtaagccatg catgttgatg gtgctgccaa    7080
gaataggcac cttcttggat gtgtgcttct tgtctagacg aataagaaat tgtcttgcct    7140
```

```
                                                                -continued aagattaaat atatatggat atttttccta agaaaagttt tagaaaagac tgatgagtgt    7200
atttctatgt aattggaata tatttaagtt catgccatgt gtcttgtggt ttccttatta    7260
ccaaaacggt gactgaagaa acgcttgctt tagaaataca ttgaattggc caggtgtgct    7320
ggctcacacc tgaaatcaca acacattggg aggccaaggc agaaggatca cttgagccca    7380
ggagttcgag cctgggcaac atagtgagac cctgtctcta caaaaaatta aaaaattagt    7440
tggccatggt agtgggcgcc tgtagtccca gctgcttggc taaggtgaga ggtttgcttg    7500
agcctgggag gttgaggctg cggtgagcta tgatagcacc attgtattcc agcctgagta    7560
acagagaaag accctgtctc agaaaaaaaa aaaatacatt gaattgtttc ctgatgggaa    7620
gtaaatactc tcatgcccag ttaggagtga gtcagggttt ttaatatgcc acttttctt     7680 tctcaggcaa ctcatgcagc aattccagaa ccccgacttc ccacccgaag tagaggaaca    7740
ggatgccagc accctgcctg tgtcttgtgc ctgggagagt gggatgaaac gccacagagc    7800
agcctgtgct tcggctagta ttaatgtgta gatagcactc tggtagctgt taactgcaag    7860
tttagcttga attaagggat ttgggggggac catgtaactt aattactgct agttttgaaa    7920
tgtctttgta agagtagggt cgccatgatg cagccatatg gaagactagg atatgggtca    7980
cacttatctg tgttcctatg gaaactattt gaatatttgt tttatatgga ttttttattca   8040 ctcttcagac acgctactca agagtgcccc tcagctgctg aacaagcatt tgtagcttgt    8100
acaatggcag aatgggccaa aagcttagtg ttgtgacctg tttttaaaat aaagtatctt    8160
gaaataatta ggcattggga cgtt                                           8184

<210> SEQ ID NO 4
<211> LENGTH: 17
<212> TYPE: DNA
<213> ORGANISM: Artificial Sequence
<220> FEATURE:
<223> OTHER INFORMATION: Synthetic nucleic acid

<400> SEQUENCE: 4
cctgggcgct ctgaggt                                                   17

<210> SEQ ID NO 5
<211> LENGTH: 17
<212> TYPE: DNA
<213> ORGANISM: Artificial Sequence
<220> FEATURE:
<223> OTHER INFORMATION: Synthetic nucleic acid

<400> SEQUENCE: 5
aggaagcggc gcctcaa                                                   17
```

CARCINOMA DIAGNOSIS AND TREATMENT BASED ON ODC1 GENOTYPE

The invention was made with government support under Grant Nos. R01 CA123065 and P50 CA095060 awarded by the National Institutes of Health. The government has certain rights in the invention.

The present application is a national phase application under 35 U.S.C. § 371 of International Application No. PCT/US2014/042979, filed Jun. 18, 2014, the entire contents of which are incorporated herein by reference.

BACKGROUND OF THE INVENTION

1. Field of the Invention

The present invention relates generally to the fields of cancer biology and medicine. More particularly, it concerns methods for the diagnosis, prevention, and treatment of carcinomas and risk factors thereof.

2. Description of Related Art

A major impediment to the translation of cancer chemoprevention research into clinical practice has been marginal agent efficacy and toxicities that exceed benefit (Psaty and Potter, 2006; Lippman, 2006). For example, the demonstrated marked efficacy of polyamine-inhibitory combination of long-term daily oral D,L-α-difluoromethylornithine (DFMO, eflornithine) and sulindac among colorectal adenoma (CRA) patients was recently demonstrated (Meyskens et al., 2008); however, treatment was associated with modest, subclinical ototoxicity (McLaren et al., 2008) and a greater number of cardiovascular events among patients with high baseline cardiovascular risk (Zell et al., 2009). Identifying genetic features that identify the suitability of a patient for a given preventative or curative treatment regime would be a major benefit.

For example, there remains a need for effective and less toxic methods for treating and preventing colorectal cancers and other carcinomas. According to the National Cancer Institute, there were approximately 147,000 new cases and 50,000 deaths from colorectal cancer in the United States in 2009. Current treatment protocols, especially those for colon cancers and polyps, include tumor resection, chemotherapy, and radiation therapy. A single nucleotide polymorphism (SNP) in intron 1 of the human ODC1 gene affects ODC1 transcription (Guo et al., 2000) and has been investigated as a genetic marker for colorectal adenoma (CRA) risk (Martinez et al., 2003; Barry et al., 2006; Hubner et al., 2008). The reported minor A-allele frequency is approximately 25% and despite differences across race/ethnicity, ODC1 genotype distribution is in Hardy-Weinberg equilibrium within each race (O'Brien et al., 2004; Zell et al., 2009). Individuals homozygous for the ODC1 minor A-allele have reduced risk of adenoma recurrence compared to those with the major G-allele (Martinez et al., 2003; Hubner et al., 2008). Furthermore, the ODC1 A-allele (AA or GA genotype, but not GG genotype) and reported aspirin usage have been associated with reduced colon polyp recurrence (Martinez et al., 2003; Barry et al., 2006; Hubner et al., 2008), and a statistically significant 50% reduced risk of advanced adenomas (Barry et al., 2006). Whether the ODC1 genotype, at this and other SNPs, differentially affects adenoma recurrence, tissue polyamine responses, toxicity profiles and how it may be used to determine the suitability of preventative and curative treatments would be a major advantage.

SUMMARY OF THE INVENTION

Thus, in accordance with the present invention, there are provided methods of treatment, prevention, and/or diagnosis related to identifying a patient's genotype at least at position +263 of at least one ODC1 allele.

In one aspect, there is provided a method for the preventative or curative treatment of carcinoma in a patient comprising:
  a) obtaining results from a test that determines the patient's genotype at position +263 of at least one ODC1 allele; and
  b) if the results indicate that the patient's genotype at position +263 of at least one allele of the ODC1 gene is T, administering to the patient effective amounts of a pharmaceutical therapy comprising:
    (i) a first agent that inhibits ornithine decarboxylase (ODC) within the patient; and
    (ii) a second agent that modulates the polyamine pathway to reduce overall polyamine content within the patient when combined with the first agent.

In some embodiments, the second agent may also increase the expression of spermidine/spermine $N^1$-acetyltransferase within the patient. In some embodiments, the results may be obtained by receiving a report containing said genotype or taking a patient history that reveals the results. In some embodiments, step a) may comprise testing the patient's genotype at position of +263 of at least one ODC1 allele.

In some embodiments, the test may determine the nucleotide base at position +263 of one allele of the ODC1 gene in the patient. In some embodiments, the test may determine the nucleotide bases at position +263 of both alleles of the ODC1 gene in the patient. In some embodiments, the results may indicate that the patient's genotype at position +263 of both alleles of the ODC1 gene is TT. In some embodiments, the results may indicate that the patient's genotype at position +263 of both alleles of the ODC1 gene is TG.

In some embodiments, the method may further comprise obtaining results from a test that determines the patient's genotype at position +316 of at least one ODC1 allele and administering to the patient an effective amount of therapy if the results indicate that the patient's genotype at position +316 of at least one allele of the ODC1 gene is G.

In some embodiments, the method may further comprise obtaining results from a test that determines the sequence of at least one of the patient's ODC1 alleles and administering to the patient an effective amount of therapy if the results indicate that the sequence of at least one of the patient's ODC1 alleles comprises at least one change, in addition to the presence of a T at position +263, as compared to the sequence provided in SEQ ID NO: 3. In some embodiments, the at least one change may be a change identified in Table A. In some embodiments, the at least one change may be a change identified in Table 2.

In some embodiments, the method may further comprise obtaining results from a test that determines the sequence of at least one of the patient's ODC1 alleles and administering to the patient an effective amount of therapy if the results indicate that the sequence of at least one of the patient's ODC1 alleles comprises at least one change, in addition to the presence of a T at position +263 and a G at position +316, as compared to the sequence provided in SEQ ID NO: 3. In some embodiments, the at least one change may be a change identified in Table A. In some embodiments, the at least one change may be a change identified in Table 2.

In some embodiments, the pharmaceutical therapy may further comprise increasing the dosage of the first or the second agent if the patient was already being treated with the pharmaceutical therapy, but at a lower dosage, prior to obtaining to the results of the test. In some embodiments, the pharmaceutical therapy may further comprise increasing the dosage of the first and the second agent if the patient was already being treated with the pharmaceutical therapy, but at a lower dosage, prior to obtaining to the results of the test. In some embodiments, the first agent may be α-difluoromethylornithine (DFMO). In some embodiments, the second agent may be a non-aspirin containing non-steroidal anti-inflammatory drug (NSAID). In some embodiments, the non-aspirin containing NSAID may be a selective COX-2 inhibitor. In some embodiments, the non-aspirin containing NSAID may be sulindac or celecoxib. In some embodiments, the non-aspirin containing NSAID may be sulindac.

In another aspect, there is provided a method for the treatment of colorectal carcinoma risk factors in a patient comprising:
a) obtaining results from a test that determines the patient's genotype at position +263 of at least one ODC1 allele; and
b) if the results indicate that the patient's genotype at position +263 of at least one allele of the ODC1 gene is T, administering to the patient effective amounts of a pharmaceutical therapy comprising:
   (i) a first agent that inhibits ornithine decarboxylase (ODC) within the patient; and
   (ii) a second agent that modulates the polyamine pathway to reduce overall polyamine content within the patient when combined with the first agent,
wherein the method prevents the formation of new aberrant crypt foci, new adenomatous polyps or new adenomas with dysplasia in the patient.

In some embodiments, the second agent may also increase the expression of spermidine/spermine $N^1$-acetyltransferase within the patient. In some embodiments, the method may prevent the formation of new aberrant crypt foci in the patient. In some embodiments, the method may prevent the formation of new adenomatous polyps in the patient. In some embodiments, the method may prevent the formation of new adenomas with dysplasia in the patient. In some embodiments, the results may be obtained by receiving a report containing said genotype or taking a patient history that reveals the results. In some embodiments, step a) may comprise testing the patient's genotype at position of +263 of at least one ODC1 allele.

In some embodiments, the test may determine the nucleotide base at position +263 of one allele of the ODC1 gene in the patient. In some embodiments, the test may determine the nucleotide bases at position +263 of both alleles of the ODC1 gene in the patient. In some embodiments, the results may indicate that the patient's genotype at position +263 of both alleles of the ODC1 gene is TT. In some embodiments, the results may indicate that the patient's genotype at position +263 of both alleles of the ODC1 gene is TG.

In some embodiments, the method may further comprise obtaining results from a test that determines the patient's genotype at position +316 of at least one ODC1 allele and administering to the patient an effective amount of therapy if the results indicate that the patient's genotype at position +316 of at least one allele of the ODC1 gene is G.

In some embodiments, the method may further comprise obtaining results from a test that determines the sequence of at least one of the patient's ODC1 alleles and administering to the patient an effective amount of therapy if the results indicate that the sequence of at least one of the patient's ODC1 alleles comprises at least one change, in addition to the presence of a T at position +263, as compared to the sequence provided in SEQ ID NO: 3. In some embodiments, the at least one change may be a change identified in Table A. In some embodiments, the at least one change may be a change identified in Table 2.

In some embodiments, the method may further comprise obtaining results from a test that determines the sequence of at least one of the patient's ODC1 alleles and administering to the patient an effective amount of therapy if the results indicate that the sequence of at least one of the patient's ODC1 alleles comprises at least one change, in addition to the presence of a T at position +263 and a G at position +316, as compared to the sequence provided in SEQ ID NO: 3. In some embodiments, the at least one change may be a change identified in Table A. In some embodiments, the at least one change may be a change identified in Table 2.

In some embodiments, the pharmaceutical therapy may further comprise increasing the dosage of the first or the second agent if the patient was already being treated with the pharmaceutical therapy, but at a lower dosage, prior to obtaining to the results of the test. In some embodiments, the pharmaceutical therapy may further comprise increasing the dosage of the first and the second agent if the patient was already being treated with the pharmaceutical therapy, but at a lower dosage, prior to obtaining to the results of the test. In some embodiments, the first agent may be α-difluoromethylornithine (DFMO). In some embodiments, the second agent may be a non-aspirin containing non-steroidal anti-inflammatory drug (NSAID). In some embodiments, the non-aspirin containing NSAID may be a selective COX-2 inhibitor. In some embodiments, the non-aspirin containing NSAID may be sulindac or celecoxib. In some embodiments, the non-aspirin containing NSAID may be sulindac In another aspect, there is provided a method for evaluating the suitability of a patient for preventative or curative treatment of carcinoma, comprising:
a) obtaining results from a test that determines the patient's genotype at position +263 of at least one ODC1 allele; and
b) if the results indicate that the patient's genotype at position +263 of at least one allele of the ODC1 gene is T, identifying the patient as suitable for treatment by a pharmaceutical therapy, said therapy comprising combined effective amounts of a first agent that inhibits ornithine decarboxylase (ODC) within the patient; and a second agent that modulates the polyamine pathway to reduce overall polyamine content within the patient when combined with the first agent.

In some embodiments, the second agent may also increase the expression of spermidine/spermine $N^1$-acetyltransferase within the patient. In some embodiments, the results may be obtained by receiving a report containing said genotype or taking a patient history that reveals the results. In some embodiments, step a) may comprise testing the patient's genotype at position of +263 of at least one ODC1 allele.

In some embodiments, the test may determine the nucleotide base at position +263 of one allele of the ODC1 gene in the patient. In some embodiments, the test may determine the nucleotide bases at position +263 of both alleles of the ODC1 gene in the patient. In some embodiments, the results may indicate that the patient's genotype at position +263 of both alleles of the ODC1 gene is TT. In some embodiments, the results may indicate that the patient's genotype at position +263 of both alleles of the ODC1 gene is TG.

In some embodiments, the method may further comprise obtaining results from a test that determines the patient's genotype at position +316 of at least one ODC1 allele and administering to the patient an effective amount of therapy if the results indicate that the patient's genotype at position +316 of at least one allele of the ODC1 gene is G.

In some embodiments, the method may further comprise obtaining results from a test that determines the sequence of at least one of the patient's ODC1 alleles and administering to the patient an effective amount of therapy if the results indicate that the sequence of at least one of the patient's ODC1 alleles comprises at least one change, in addition to the presence of a T at position +263, as compared to the sequence provided in SEQ ID NO: 3. In some embodiments, the at least one change may be a change identified in Table A. In some embodiments, the at least one change may be a change identified in Table 2.

In some embodiments, the method may further comprise obtaining results from a test that determines the sequence of at least one of the patient's ODC1 alleles and administering to the patient an effective amount of therapy if the results indicate that the sequence of at least one of the patient's ODC1 alleles comprises at least one change, in addition to the presence of a T at position +263 and a G at position +316, as compared to the sequence provided in SEQ ID NO: 3. In some embodiments, the at least one change may be a change identified in Table A. In some embodiments, the at least one change may be a change identified in Table 2.

In some embodiments, the pharmaceutical therapy may further comprise increasing the dosage of the first or the second agent if the patient was already being treated with the pharmaceutical therapy, but at a lower dosage, prior to obtaining to the results of the test. In some embodiments, the pharmaceutical therapy may further comprise increasing the dosage of the first and the second agent if the patient was already being treated with the pharmaceutical therapy, but at a lower dosage, prior to obtaining to the results of the test. In some embodiments, the first agent may be α-difluoromethylornithine (DFMO). In some embodiments, the second agent may be a non-aspirin containing non-steroidal anti-inflammatory drug (NSAID). In some embodiments, the non-aspirin containing NSAID may be a selective COX-2 inhibitor. In some embodiments, the non-aspirin containing NSAID may be sulindac or celecoxib. In some embodiments, the non-aspirin containing NSAID may be sulindac.

In another aspect, there is provided a method for preventing the development or recurrence of a carcinoma in a patient at risk therefor comprising:
 a) obtaining results from a test that determines the patient's genotype at position +263 of at least one ODC1 allele; and
 b) administering to the patient combined effective amounts of α-difluoromethylornithine (DFMO) and a non-aspirin containing non-steroidal anti-inflammatory drug (NSAID) if the results indicate that the patient's genotype at position +263 of at least one allele of the ODC1 gene is T.

In some embodiments, the second agent may also increase the expression of spermidine/spermine $N^1$-acetyltransferase within the patient. In some embodiments, the results may be obtained by receiving a report containing said genotype or taking a patient history that reveals the results. In some embodiments, step a) may comprise testing the patient's genotype at position of +263 of at least one ODC1 allele.

In some embodiments, the test may determine the nucleotide base at position +263 of one allele of the ODC1 gene in the patient. In some embodiments, the test may determine the nucleotide bases at position +263 of both alleles of the ODC1 gene in the patient. In some embodiments, the results may indicate that the patient's genotype at position +263 of both alleles of the ODC1 gene is TT. In some embodiments, the results may indicate that the patient's genotype at position +263 of both alleles of the ODC1 gene is TG.

In some embodiments, the method may further comprise obtaining results from a test that determines the patient's genotype at position +316 of at least one ODC1 allele and administering to the patient an effective amount of therapy if the results indicate that the patient's genotype at position +316 of at least one allele of the ODC1 gene is G.

In some embodiments, the method may further comprise obtaining results from a test that determines the sequence of at least one of the patient's ODC1 alleles and administering to the patient an effective amount of therapy if the results indicate that the sequence of at least one of the patient's ODC1 alleles comprises at least one change, in addition to the presence of a T at position +263, as compared to the sequence provided in SEQ ID NO: 3. In some embodiments, the at least one change may be a change identified in Table A. In some embodiments, the at least one change may be a change identified in Table 2.

In some embodiments, the method may further comprise obtaining results from a test that determines the sequence of at least one of the patient's ODC1 alleles and administering to the patient an effective amount of therapy if the results indicate that the sequence of at least one of the patient's ODC1 alleles comprises at least one change, in addition to the presence of a T at position +263 and a G at position +316, as compared to the sequence provided in SEQ ID NO: 3. In some embodiments, the at least one change may be a change identified in Table A. In some embodiments, the at least one change may be a change identified in Table 2.

In another aspect, there is provided a method for treating a patient at risk for development or recurrence of carcinoma with α-difluoromethylornithine (DFMO) and a non-aspirin containing non-steroidal anti-inflammatory drug (NSAID), comprising administering to the patient effective amounts of α-difluoromethylornithine (DFMO) and a non-aspirin containing non-steroidal anti-inflammatory drug (NSAID), wherein the patient has been identified as having a T at position +263 of at least one ODC1 allele.

In some embodiments, the results may indicate that the patient's genotype at position +263 of both alleles of the ODC1 gene is TT. In some embodiments, the results may indicate that the patient's genotype at position +263 of both alleles of the ODC1 gene is TG.

In another aspect, there is provided a method for treating a carcinoma in a patient comprising:
 a) obtaining results from a test that determines the patient's genotype at position +263 of at least one ODC1 allele; and
 b) administering to the patient combined effective amounts of α-difluoromethylornithine (DFMO) and a non-aspirin containing non-steroidal anti-inflammatory drug (NSAID) if the results indicate that the patient's genotype at position +263 of the ODC1 gene of at least one allele is T.

In some embodiments, the second agent may also increase the expression of spermidine/spermine $N^1$-acetyltransferase within the patient. In some embodiments, the results may be obtained by receiving a report containing said genotype or taking a patient history that reveals the results. In some embodiments, step a) may comprise testing the patient's genotype at position of +263 of at least one ODC1 allele.

In some embodiments, the test may determine the nucleotide base at position +263 of one allele of the ODC1 gene in the patient. In some embodiments, the test may determine the nucleotide bases at position +263 of both alleles of the ODC1 gene in the patient. In some embodiments, the results may indicate that the patient's genotype at position +263 of both alleles of the ODC1 gene is TT. In some embodiments, the results may indicate that the patient's genotype at position +263 of both alleles of the ODC1 gene is TG.

In some embodiments, the method may further comprise obtaining results from a test that determines the patient's genotype at position +316 of at least one ODC1 allele and administering to the patient an effective amount of therapy if the results indicate that the patient's genotype at position +316 of at least one allele of the ODC1 gene is G.

In some embodiments, the method may further comprise obtaining results from a test that determines the sequence of at least one of the patient's ODC1 alleles and administering to the patient an effective amount of therapy if the results indicate that the sequence of at least one of the patient's ODC1 alleles comprises at least one change, in addition to the presence of a T at position +263, as compared to the sequence provided in SEQ ID NO: 3. In some embodiments, the at least one change may be a change identified in Table A. In some embodiments, the at least one change may be a change identified in Table 2.

In some embodiments, the method may further comprise obtaining results from a test that determines the sequence of at least one of the patient's ODC1 alleles and administering to the patient an effective amount of therapy if the results indicate that the sequence of at least one of the patient's ODC1 alleles comprises at least one change, in addition to the presence of a T at position +263 and a G at position +316, as compared to the sequence provided in SEQ ID NO: 3. In some embodiments, the at least one change may be a change identified in Table A. In some embodiments, the at least one change may be a change identified in Table 2.

In some embodiments, the pharmaceutical therapy may further comprise increasing the dosage of the first or the second agent if the patient was already being treated with the pharmaceutical therapy, but at a lower dosage, prior to obtaining to the results of the test. In some embodiments, the pharmaceutical therapy may further comprise increasing the dosage of the first and the second agent if the patient was already being treated with the pharmaceutical therapy, but at a lower dosage, prior to obtaining to the results of the test. In some embodiments, the first agent may be α-difluoromethylornithine (DFMO). In some embodiments, the second agent may be a non-aspirin containing non-steroidal anti-inflammatory drug (NSAID). In some embodiments, the non-aspirin containing NSAID may be a selective COX-2 inhibitor. In some embodiments, the non-aspirin containing NSAID may be sulindac or celecoxib. In some embodiments, the non-aspirin containing NSAID may be sulindac.

In variations on any of the above embodiments, the non-aspirin containing NSAID may be a selective COX-2 inhibitor. In some embodiments, the non-aspirin containing NSAID may be sulindac or celecoxib. In some embodiments, the non-aspirin containing NSAID may be sulindac. In some embodiments, DFMO and sulindac may be administered systemically. In some embodiments, DFMO and sulindac may be administered by distinct routes. In some embodiments, the DFMO or the non-aspirin containing NSAID may be administered orally, intraarterially or intravenously. In some embodiments, the DFMO may be administered orally. In some embodiments, the effective amount of DFMO may be 500 mg/day. In some embodiments, the DFMO may be administered intravenously. In some embodiments, the effective amount of DFMO may be from about 0.05 to about 5.0 g/m$^2$/day. In some embodiments, the DFMO and the non-aspirin containing NSAID may be formulated for oral administration. In some embodiments, the DFMO and the non-aspirin containing NSAID may be formulated as a hard or soft capsule or a tablet. In some embodiments, the DFMO and the non-aspirin containing NSAID may be administered every 12 hours. In some embodiments, the DFMO and the non-aspirin containing NSAID may be administered every 24 hours. In some embodiments, the effective amount of sulindac may be from about 10 to about 1500 mg/day. In some embodiments, the effective amount of sulindac may be from about 10 to about 400 mg/day. In some embodiments, the effective amount of sulindac may be 150 mg/day. In some embodiments, DFMO may be administered prior to sulindac. In some embodiments, DFMO may be administered after sulindac. In some embodiments, DFMO may be administered before and after sulindac. In some embodiments, DFMO may be administered concurrently with sulindac. In some embodiments, DFMO may be administered at least a second time. In some embodiments, sulindac may be administered at least a second time.

In variations on any of the above embodiments, the patient may have a solid tumor, and said method may further comprise resection of said solid tumor. In some embodiments, DFMO and sulindac may be administered prior to said resection. In some embodiments, DFMO and sulindac may be administered after said resection.

In variations on any of the above embodiments, the carcinoma may be colorectal cancer, neuroblastoma, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, or glioblastoma. In some embodiments, the carcinoma may be colorectal cancer. In some embodiments, the colorectal cancer may be stage I. In some embodiments, the colorectal cancer may be stage II. In some embodiments, the colorectal cancer may be stage III. In some embodiments, the colorectal cancer may be stage IV.

In variations on any of the above embodiments, the method may prevent the formation of new advanced colorectal neoplasms within the patient. In some embodiments, the method may prevent ototoxicity or the risk thereof within the patient. In some embodiments, the method may prevent the formation of new right-sided advanced colorectal neoplasms. In some embodiments, the method may prevent the formation of new left-sided advanced colorectal neoplasms.

In variations on any of the above embodiments, the patient may have been identified as having one or more adenomatous polyps in the colon, rectum or appendix. In some embodiments, the patient may have been identified as having one or more advanced colorectal neoplasms. In some embodiments, the patient may have been identified as having one or more left-side advanced colorectal neoplasms. In some embodiments, the patient may have been identified as having one or more right-sided advanced colorectal neoplasms. In some embodiments, the patient may have been diagnosed with familial adenomatous polyposis. In some embodiments, the patient may have been diagnosed with Lynch syndrome. In some embodiments, the patient may have been diagnosed with familial colorectal cancer type X.

In some embodiments, the patient may satisfy the Amsterdam Criteria or the Amsterdam Criteria II. In some embodiments, the patient may have a history of resection of one or more colorectal adenomas. In some embodiments, the patient may have an intraepithelial neoplasia or a precancerous lesion associated ODC hyperactivity. In some embodiments, the patient may have an intraepithelial neoplasia or a precancerous lesion and elevated cellular polyamine levels.

In variations on any of the above embodiments, the patient may be human.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

As used herein, the term "$IC_{50}$" refers to an inhibitory dose which is 50% of the maximum response obtained.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
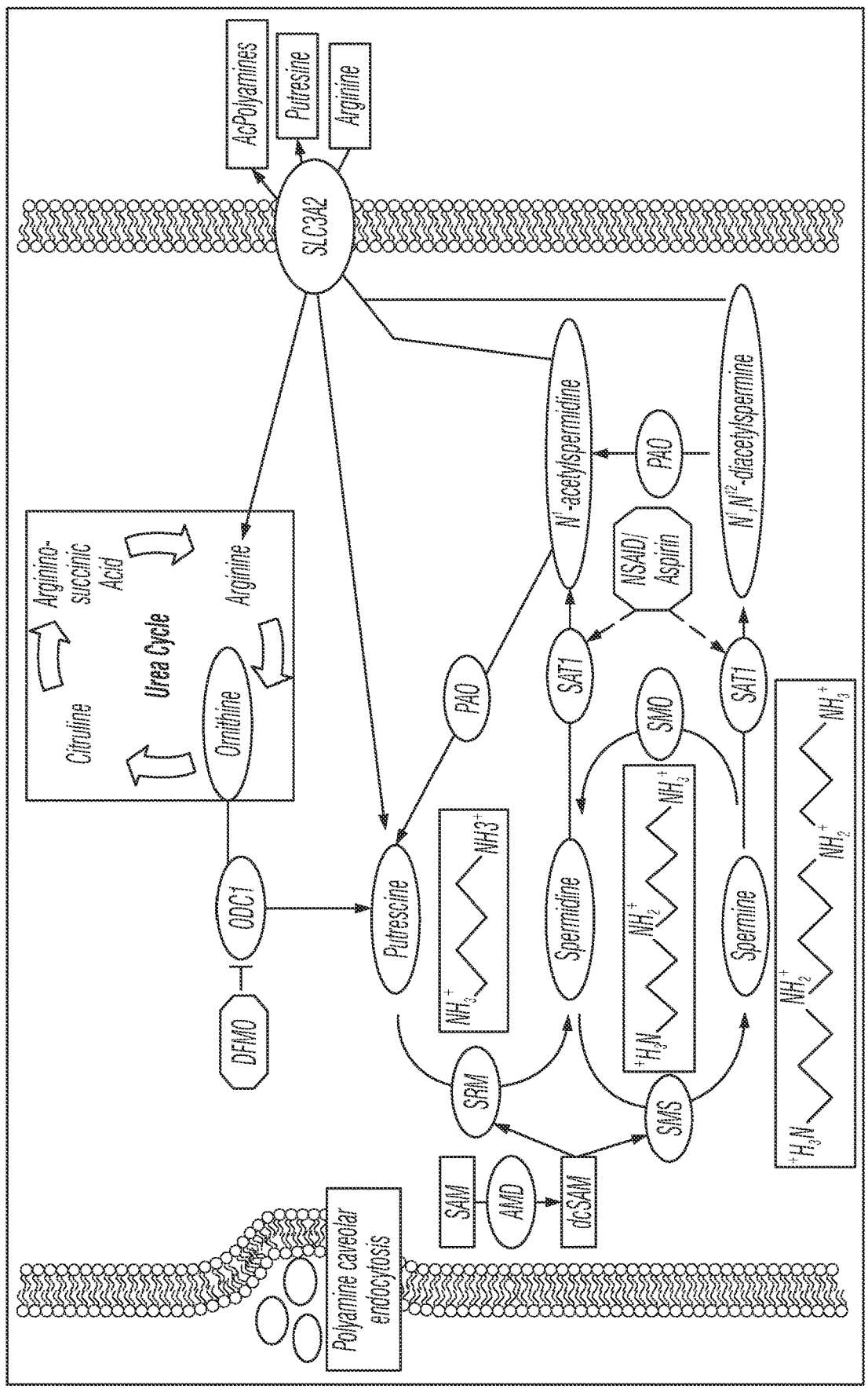
FIG. 1. A schematic representation of polyamine metabolism in mammals. The metabolism of arginine in the urea cycle (square) results in ornithine production. Ornithine decarboxylase (ODC1), the first enzyme in the polyamine (ovals) pathway, converts ornithine to putresine. Decarboxylation of S-adenosylmethionine (SAM), by S-adenosylmethionine decarboxylase (AMD) yields decarboxylated SAM (dcSAM), which donates its propyl amine moiety (not shown) for the formation of spermidine and subsequently spermine by spermidine synthase (SRM) and spermine synthase (SMS), respectively. The opposite reaction, spermine to spermidine, is catalyzed by spermine oxidase (SMO). Spermidine and spermine can be mono and either mono or di-acetylated by spermidine/spermine acetyl acetyltransferase (SAT1) to be exported by the SLC3A2 transporter. Both acetylated polyamines can be converted back to putresine by polyamine oxidase (PAO). Polyamine caveolar endocytosis from luminal bacteria and SLC3A2-dependent putresine importer are also shown. The drug difluoromethylornithine (DFMO) blocks the activity of the ODC enzyme decreasing the level of polyamine. Non-steroidal anti-inflammatory drugs (NSAID) and aspirin induce the activity of the SAT1 enzyme to further increase the export of acetylated polyamine from the cell.

Dysregulation of cellular metabolism is associated with multiple diseases including cancer. Polyamines are organic cations shown to control gene expression at the transcriptional, post-transcriptional, and translational level. The activity of ornithine decarboxylase (ODC), the first enzyme in polyamine synthesis, is associated with normal and neoplastic growth. Increased polyamine levels and ODC activity are associated with increased risk of colorectal neoplasia. ODC expression is regulated in part by E-box transcription factors, including MYC and MAD family members. The ODC1 gene contains several SNPs that are associated with the risk of colorectal neoplasia, the third leading cause of cancer death. A single nucleotide polymorphism (SNP; rs2302615 located +316 nucleotides 3' of the transcription start site) in the ODC1 intron 1 promoter region has been found to be both functional and prognostic for risk of colorectal carcinogenesis. Both transcriptional activator MYC and transcriptional repressor MAD preferentially bind the ODC1 promoter element containing the minor A-allele at SNP+316, which is flanked by two E-boxes, resulting in allele-specific expression. Also the ODC1 +316 SNP is associated with both risk of metachronous colorectal adenoma, especially in non-steroidal anti-inflammatory drug (NSAID) users, and is detrimental for survival after colorectal cancer diagnosis, as well as other phenotypes, such as meat consumption and polyamine intake.

As described herein, a comprehensive investigation of the genetic variability in the ODC1 gene was performed. The frequencies of 12 SNPs occurring in participants of a clinical cancer prevention trial were determined. Haplotypes accounting for over 90% of the genetic diversity in ODC1 were identified. Two ODC1 intron 1 SNPs, rs2302616 (located +263 nucleotides 3' of the transcription start site) and rs2302615, were found to be associated with disease processes and accounted for more than half of the participants in the clinical trial. Both SNPs predicted metachronous adenoma and response to agents targeting the polyamine pathway in participants of the clinical trial. The rs2302616 SNP functionally modulated a DNA G-quadruplex structure and predicted the ODC1 rate-limiting product putrescine by genotype. Both SNPs cooperated to modulate ODC1 transcriptional activity involving both a G-quadruplex structure and Sp1 binding site at rs2302616, and rs2302615 flanked MYC-binding E-boxes. Haplotype analysis using both SNPs might provide better discrimination of both disease prognosis and treatment prediction in cancer patients.

In several aspects, methods are provided that comprise predicting the suitability, efficacy, toxicity, and/or dosage of anti-carcinoma combination therapies comprising an ornithine decarboxylase (ODC) inhibitor and a spermidine/spermine $N^1$-acetyltransferase expression agonist based at least in part on the patient's ODC1 promoter genotype.

The present invention also involves the delivery of therapeutic compounds to individuals exhibiting pre-cancerous symptoms to prevent the onset of cancer and/or to prevent the onset of cancer risk factors, such as the formation of new aberrant crypt foci, the formation of new adenomatous polyps or new adenomas with dysplasia. Cells of this category include polyps and other precancerous lesions, premalignancies, preneoplastic or other aberrant phenotypes indicating probable progression to a cancerous state, based at least in part on the patient's ODC1 promoter genotype.

I. ASPECTS OF THE PRESENT INVENTION

The naturally occurring polycationic polyamines (putrescine, spermidine and spermine) are ubiquitous, low-molecular weight aliphatic amines that play multifunctional roles in cell growth, development, and survival (Larque et al., 2007). Ornithine decarboxylase (ODC1) is the first enzyme in polyamine biosynthesis and catalyzes the formation of putrescine from ornithine. The ODC gene is essential for cell survival in early murine development (Bailey et al., 2010). ODC1 is regulated by the WNT signaling pathway, a major cascade governing epithelial development (Mishra et al., 2005; Groden et al., 1991). In carcinogenic tissue, the dysregulation of the WNT pathway by loss of the adenomatous polyposis coli (APC) tumor suppression gene leads to increased expression of ODC1, via a c-MYC dependent process, and thus polyamine synthesis (Kinzler et al., 1991; Reya and Clevers, 2005; Kern et al., 1991; Moser et al., 1990).

The ODC promoter/intron 1 region contains multiple sequences that allow transcriptional control via response to hormones, growth factors, tumor promoters, and transcription factors (Pegg, 2009). In addition, ODC1 might be regulated by ncRNA. The 5' flanking region of ODC1 has a long non-coding RNA (lncRNA) named LOC101929715 and ODC1 intron 1 encodes SNORA80B, a small nucleolar RNA (snoRNA), both of which are uncharacterized at the transcriptional level and for their downstream effects.

Polyamine metabolism is a validated pathway for chemoprevention and treatment of cancer. Evidence from cell line experiments, mouse models, and clinical trials validate this pathway as a target for colorectal cancer prevention. Currently two clinical trials are on-going, including one in FAP (Identifier: NCT01483144) and another in neuroblastoma (Identifier: NCT01586260). To date, the mechanisms by which polyamines elicit their tumorigenic effects and the molecular mechanisms to explain clinical outcomes are poorly understood (Sporn and Hong, 2008; Zell et al., 2010; Fultz and Gerner, 2002).

A SNP in intron 1 of ODC1 with a G to A change is located at position +316 relative to the transcription start site (TSS) and is flanked by two c-MYC-binding E-boxes (Pena et al., 1993; Kumar et al., 2009; Nilsson et al., 2004). A clinical association has been established between ODC1 +316 genotype and reduced risk of colorectal adenoma (CRA) recurrence by different studies, especially in aspirin users (Walhout et al., 1998; Martinez et al., 2003; Barry et al., 2006; Hubner et al., 2008; Hughes et al., 2010). However, in sporadic colorectal cancer, the ODC1 +316 A-allele is associated with poor survival (Martinez et al., 2003). ODC1 +316 is functional and may have both promoting and inhibiting effect on colorectal carcinogenesis by affecting the levels of transcription of ODC1. These dual roles can be explained at the molecular level because both E-box activators (c-MYC expression in transformed epithelium) and repressors (MAD1 expression in normal epithelium) bind preferentially to the ODC1 +316 A-allele, as demonstrated by allele-specific promoter reporter luciferase and chromatin immunoprecipitation (ChIP) experiments (Martinez et al., 2003).

In the studies described herein, the importance of genetic variability in ODC1 was investigated using isogenic luciferase reporters lacking an SV40 enhancer (pGL3-Basic, Promega). Since ODC1 contains numerous SNPs (see Table A), a comprehensive investigation to understand the significance of the genetic variability in ODC1 and its 3' and 5' flanking regions was conducted (Huppert and Balasubramanian, 2005). These studies also sought to understand the molecular mechanisms that explain the clinical associations in this disease process (Huppert and Balasubramanian, 2005). The frequencies of 49 ODC1 SNPs were confirmed in 196 patients participating in a DFMO/sulindac cancer prevention trial (Erdman et al., 1999) using a SNP genotyping array and allele-specific discrimination. Eleven ODC1 SNPs with minor allele frequencies around 10% were identified and determined to be common haplotypes accounting for more than 90% of participants. SNPs in intron 1 and exon 2 (part of the 5' UTR) of ODC1 were carefully examined for their association with phenotype. Computational approaches showed that SNPs in the 5' UTR disrupt an internal ribosome entry site (IRES) that allows differential regulation at the level of translation. Those SNPs did not show variability in the presently described clinical samples and SNP database and/or did not associate with phenotype, such as polyamine levels or polyp occurrence. The transcriptional contribution of a single SNP, which exists in a GC-rich region in intron 1 capable of forming a G-quadruplex DNA secondary structure, was further studied.

In the studies described herein, the ODC1 +263 SNP was identified, validated, and found to modulate a G-quadruplex structure. In addition, the ODC1 +263 SNP was studied in the context of previous work focusing on ODC1 +316 SNP in relation to clinical outcome and response to DFMO/sulindac treatment.

The ODC1 +263 SNP (rs2302616) (1) divided observed frequencies in two major groups in participants of the clinical trial, (2) is located within a GC-rich region forming a DNA secondary structure called a G-quadruplex (G4) as predicted by computational studies using Quadparser software (Messeguer et al., 2002), (3) disrupted a consensus Sp1/Sp3 transcription factor binding sequence as predicted by PROMO software (Farre et al., 2003; Raiber et al., 2012), and (4) predicted statistically significant putrescine levels by genotype in normal tissue at baseline in participants of the DFMO/sulindac trial. Thus, the ODC1 +263 SNP may be involved in a novel molecular mechanism of gene regulation, which may refine genotype associations with clinical parameters.

The ability of the ODC1 +263 SNP to affect a G-quadruplex DNA secondary structure was studied using circular dichroism (CD), melting temperature, and EMSA. The ODC1 +263 SNP was able to form a G-quadruplex structure with either G or T at this position. In addition, the thermal stability of the G-quadruplex structure demonstrated that the ODC1 +263 G-allele forms a more stable G-quadruplex structure than the ODC1 +263 T-allele. Isogenic reporter luciferase plasmids were constructed to test the functional significance of the ODC1 +263 SNP. The T-allele drove more luciferase expression, which is consistent with the in vitro thermal stability assays. The effects of the Sp1 transcription factor were studied in vitro and in vivo. In vitro, Sp1 modulated the equilibrium between the G-quadruplex structure and double-stranded (ds) DNA, as previously reported (Kumar et al., 1997). The HCT116 colorectal cancer cell line was used to study the role of Sp1 transcription factor using genetic approaches. When Sp1 protein was knocked down using siRNA technology, an induction of ODC1 transcription was observed for both ODC1 +263 alleles. This transcriptional activation was higher in the presence of the G-allele, which forms the more stable G-quadruplex structure. In addition full-length Sp1 protein was over-expressed using a mammalian expression vector (pN3). Sp1 protein did not significantly down-regulate ODC1 expression. When this observation is taken together with the in vitro data, in which the equilibrium between G-quadruplex and dsDNA is dependent on the concentration of Sp1 protein, it can be concluded that the overexpression of Sp1 protein is maintaining the ODC1 promoter-driven plasmid in a state of dsDNA, which is not responsive to higher concentrations of Sp1 protein. In contrast, the equilibrium appeared to favor the G-quadruplex conformation over dsDNA when Sp1 expression was knocked down. The G-quadruplex conformation appears to induce the expression of the ODC1 promoter-driven plasmid, where the stability of the G-quadruplex, or its association with other transcription factors, may be affecting the level of transcription of ODC1.

Diplotypes were constructed using both ODC1 +263 and +316 SNPs since they are close enough to preclude the occurrence of an intervening recombination event. Limited haplotypes were found, which argue for a selective pressure over ODC1. More likely the ODC1 +263 SNP is a later event than ODC1 +316 SNP in evolution. A comprehensive investigation of the genetic variability in ODC1 was performed and limited haplotype diversity accounting for over 90% of the population was found. Mechanistically, two of the haplotypes, which account for more than half of the participants, were addressed. Both ODC1 intron 1 SNPs were found to be associated with disease processes, and both predicted metachronous adenoma and response to treatment in participants of the DFMO/sulindac trial. Only SNP rs2302616 predicted the ODC1 rate-limiting product putrescine by genotype, which highlights the importance of the transcriptional control of ODC1. Both SNPs modulated ODC1 transcriptional activity involving a G-quadruplex structure and the Sp1 binding at ODC1 +263, and ODC1 +316-flanked MYC-binding E-boxes. c-MYC cooperated with Sp1 to activate the transcription of ODC1, in a mechanism that involves the N-terminal domain of Sp1 and the stability of the G-quadruplex formation. Thus, the ODC1 +263 SNP is functional in the regulation of ODC1, as well as the previously reported ODC1 +316 SNP, and they are likely working together to regulate ODC1 transcription.

TABLE A

Known SNPs in ODC1

| SNP ID | Chr 2 pos | Sequence | SNP ID | Chr 2 pos | Sequence |
|---|---|---|---|---|---|
| rs138392792 | 10432240(+) | C/G | rs189103228 | 10438687(+) | A/G |
| rs28362422 | 10432253(−) | C/T | rs59246308 | 10438762(+) | C/T |
| rs28362421 | 10432273(−) | TGTGT | rs148879789 | 10438847(+) | A/G |
| rs181100171 | 10432376(+) | C/G | rs12616336 | 10438892(+) | A/G |
| rs147275701 | 10432382(+) | A/G | rs28362381 | 10438984(−) | A/G |
| rs28362420 | 10432403(−) | G/A | rs28362380 | 10439012(−) | A/G |
| rs28362419 | 10432596(−) | A/G | rs7608353 | 10439022(+) | A/G |
| rs16856239 | 10432691(+) | C/T | rs7558222 | 10439043(+) | A/T |
| rs117634324 | 10432708(+) | C/G | rs192090667 | 10439130(+) | C/T |
| rs28362418 | 10432759(−) | G/A | rs184171467 | 10439155(+) | C/G |
| rs185195027 | 10432860(+) | C/T | rs138219715 | 10439317(+) | A/C |
| rs189662188 | 10432890(+) | A/G | rs7558559 | 10439401(+) | T/A |
| rs28362417 | 10433046(−) | T/C | rs28362379 | 10439466(−) | T/G |
| rs144846017 | 10433100(+) | C/T | rs200357846 | 10439566(+) | —/C |
| rs183432213 | 10433133(+) | A/G | rs116245326 | 10439575(+) | C/T |
| rs1049500 | 10433199(−) | C/T | rs28362378 | 10439602(−) | T/C |
| rs189035164 | 10433299(+) | C/T | rs144229860 | 10439606(+) | —/TCAA |
| rs111950270 | 10433319(+) | T/— | rs10490729 | 10439625(+) | G/C |
| rs150895708 | 10433385(+) | C/G | rs28362377 | 10439736(−) | A/— |
| rs191790424 | 10433391(+) | C/T | rs28362376 | 10439777(−) | T/C |
| rs28362416 | 10433501(−) | C/T | rs181138553 | 10439797(+) | C/T |
| rs28362415 | 10433600(−) | G/T | rs2430422 | 10440101(+) | A/G |
| rs183702659 | 10433706(+) | C/T | rs146435265 | 10440263(+) | C/G |
| rs28362413 | 10433774(−) | C/G | rs115030661 | 10440277(+) | C/A |
| rs112139879 | 10433865(+) | A/G | rs2302615 | 10440370(+) | C/T |
| rs188227508 | 10433869(+) | C/T | rs28362374 | 10440411(−) | C/T |
| rs1804032 | 10433989(−) | T/C | rs2302616 | 10440423(+) | C/A |
| rs28362411 | 10434031(−) | A/G | rs375952999 | 10434510(+) | A/G |
| rs28362410 | 10434111(−) | A/G | rs377608345 | 10434363(+) | C/T |
| rs28362409 | 10434123(−) | G/A | rs371025449 | 10437296(+) | A/G |
| rs200587333 | 10434124(+) | A/G | rs28362387 | 10438046(−) | C/T |
| rs368447466 | 10434128(+) | C/T | rs79403289 | 10438002(+) | T/A |
| rs111482605 | 10434185(+) | A/C/T | rs376445830 | 10436986(+) | C/T |
| rs141844180 | 10434275(+) | G/A | rs367574241 | 10436166(+) | A/C |
| rs201790003 | 10434306(+) | A/T | rs374601465 | 10433193(+) | C/G |
| rs115655138 | 10434342(+) | C/T | rs377353326 | 10439682(+) | A/C |
| rs28362407 | 10434428(−) | G/A | rs28362385 | 10438101(−) | G/T |
| rs147667657 | 10434455(+) | G/T | rs369239741 | 10435683(+) | —/A |
| rs61733046 | 10434481(+) | C/T | rs28362408 | 10434142(−) | TTAA/— |
| rs115291858 | 10434494(+) | A/G | rs34007534 | 10439802(+) | C/G |
| rs114981547 | 10434509(+) | C/T | rs375812175 | 10436085(+) | G/T |
| rs150152038 | 10434526(+) | C/G | rs373811110 | 10435556(+) | C/T |
| rs28362406 | 10434539(−) | C/A | rs140096943 | 10437348(+) | C/T |
| rs186920569 | 10434600(+) | C/T | rs373334646 | 10436872(+) | G/T |
| rs7599144 | 10434641(+) | C/T | rs5829265 | 10586259(+) | —/T/TT |
| rs145483973 | 10434647(+) | A/G | rs376565027 | 10434569(+) | A/G |
| rs191387936 | 10434691(+) | A/C/T | rs112161284 | 10434462(+) | C/T |
| rs6708087 | 10434698(+) | A/T | rs376999558 | 10433332(+) | C/T |
| rs28362405 | 10434724(−) | C/T | rs148808377 | 10437372(+) | C/T |
| rs144020397 | 10434745(+) | C/G | rs375809058 | 10437555(+) | G/T |
| rs146453850 | 10434767(+) | C/T | rs149519682 | 10434250(+) | A/G |
| rs7559979 | 10434911(+) | G/A | rs113063419 | 10432961(+) | T/A |
| rs2357550 | 10435022(+) | T/C | rs376058087 | 10434019(+) | A/G |
| rs140976041 | 10435057(+) | C/G | rs373311476 | 10434096(+) | A/G |
| rs184125549 | 10435071(+) | G/T | rs143684877 | 10436472(+) | T/G |
| rs143138545 | 10435218(+) | A/G | rs372685666 | 10438634(+) | A/G |
| rs3832141 | 10435244(−) | A/— | rs138150709 | 10436549(+) | G/A |

TABLE A-continued

Known SNPs in ODC1

| SNP ID | Chr 2 pos | Sequence | SNP ID | Chr 2 pos | Sequence |
|---|---|---|---|---|---|
| rs1405948 | 10435392(−) | C/T | rs34562944 | 10440430(+) | —/G |
| rs148268330 | 10435548(+) | A/T | rs373940182 | 10436216(+) | C/T |
| rs13396481 | 10435553(+) | C/T | rs35616112 | 10435468(+) | —/A |
| rs11538363 | 10435633(−) | C/T | rs367991974 | 10437015(+) | A/G |
| rs190678797 | 10435710(+) | A/T | rs144020639 | 10433899(+) | C/T |
| rs193033745 | 10435763(+) | C/T | rs376744105 | 10436788(+) | G/T |
| rs138255982 | 10435765(+) | G/T | rs373354898 | 10438438(+) | A/G |
| rs200737468 | 10435816(+) | C/T | rs141788096 | 10433101(+) | G/A |
| rs199713576 | 10435817(+) | A/G | rs200204650 | 10436034(+) | C/T |
| rs114387410 | 10435923(+) | A/G | rs11538368 | 10436189(−) | G/T |
| rs28362402 | 10435942(−) | T/— | rs145681887 | 10435905(+) | G/A |
| rs201608190 | 10435951(+) | A/C | rs34608521 | 10440181(+) | —/G |
| rs374811349 | 10435981(+) | A/G | rs370233699 | 10433187(+) | A/G |
| rs143840340 | 10435994(+) | A/G | rs377617130 | 10437257(+) | C/G |
| rs188863393 | 10436004(+) | C/T | rs373083738 | 10432551(+) | C/T |
| rs28362401 | 10436022(−) | G/C | rs367560002 | 10433983(+) | C/T |
| rs116522452 | 10436076(+) | C/T | rs376226682 | 10433636(+) | C/T |
| rs200691250 | 10436078(+) | A/C/G | rs14589 | 10432800(−) | T/C |
| rs115102834 | 10436097(+) | G/A | rs368504231 | 10433870(+) | A/G |
| rs185441020 | 10436143(+) | A/C | rs143912083 | 10433088(+) | A/C |
| rs114826666 | 10436157(+) | C/T | rs372696508 | 10433202(+) | A/G |
| rs188346039 | 10436199(+) | A/T | rs374437813 | 10433840(+) | C/G |
| rs201790435 | 10436205(+) | G/A | rs139964676 | 10433132(+) | C/T |
| rs3752661 | 10436254(+) | T/C | rs3036408 | 10438508(+) | —/T/TT |
| rs139158278 | 10436302(+) | A/G | rs143860094 | 10435632(+) | C/T |
| rs28362400 | 10436333(−) | C/T | rs141854481 | 10434527(+) | G/A |
| rs28362399 | 10436354(−) | T/C | rs111489863 | 10432618(+) | C/T |
| rs180900746 | 10436356(+) | A/C | rs28362414 | 10433645(−) | G/A |
| rs149399944 | 10436407(+) | A/G | rs375870896 | 10432416(+) | —/G |
| rs28362398 | 10436428(−) | C/G | rs11538369 | 10436556(−) | C/T |
| rs200293974 | 10436477(+) | A/G | rs372547055 | 10434104(+) | A/G |
| rs202023169 | 10436659(+) | A/T | rs372516888 | 10433060(+) | G/T |
| rs192347282 | 10436825(+) | C/T | rs371877950 | 10437475(+) | A/G |
| rs138359527 | 10436858(+) | C/T | rs368205761 | 10435059(+) | C/G |
| rs28362397 | 10436871(−) | C/T | rs138045213 | 10434061(+) | C/G |
| rs187081116 | 10436931(+) | C/G | rs372154312 | 10436671(+) | C/T |
| rs114251583 | 10436933(+) | G/A | rs373507220 | 10436057(+) | C/T |
| rs113748944 | 10437079(+) | T/C | rs373045430 | 10435853(+) | C/T |
| rs190569727 | 10437172(+) | C/T | rs375286431 | 10437243(+) | C/T |
| rs182814014 | 10437195(+) | A/T | rs139046118 | 10434371(+) | A/G |
| rs28362396 | 10437206(−) | A/G | rs375522035 | 10437500(+) | A/G |
| rs28362395 | 10437209(−) | G/A | rs79553909 | 10435076(+) | C/T |
| rs201242857 | 10437349(+) | A/G | rs113241465 | 10436150(+) | C/T |
| rs6738288 | 10437396(+) | C/T | rs139506756 | 10434381(+) | G/A |
| rs6753098 | 10437488(+) | A/G | rs371443385 | 10434003(+) | A/G |
| rs187187788 | 10437529(+) | C/T | rs140323723 | 10436474(+) | G/A |
| rs2302613 | 10437534(+) | T/C | rs142575004 | 10434380(+) | C/T |
| rs11538365 | 10437535(−) | A/G | rs200858806 | 10435076(+) | —/T |
| rs2302614 | 10437543(+) | A/C | rs368830902 | 10436547(+) | C/G |
| rs191647439 | 10437549(+) | C/T | rs28362404 | 10434935(−) | A/T |
| rs11538367 | 10437560(−) | G/A | rs142326792 | 10434458(+) | G/A |
| rs28364601 | 10437596(−) | C/T | rs141834302 | 10434015(+) | G/A |
| rs28362393 | 10437690(−) | G/A | rs374816611 | 10440127(+) | A/G |
| rs28362392 | 10437691(−) | A/G | rs34885558 | 10439740(+) | A/T |
| rs142996021 | 10437792(+) | A/G | rs201000268 | 10435244(+) | A/T |
| rs182910693 | 10437802(+) | C/G | rs374970523 | 10435708(+) | C/T |
| rs28362391 | 10437807(−) | T/G | rs369462606 | 10438095(+) | A/G |
| rs139044363 | 10437829(+) | C/G | rs371084891 | 10433231(+) | A/G |
| rs28362390 | 10437880(−) | C/G | rs34145750 | 10439769(+) | C/T |
| rs28362389 | 10437914(−) | A/C | rs376328527 | 10435950(+) | A/G |
| rs10490728 | 10437919(+) | T/C | rs370823383 | 10436234(+) | A/T |
| rs28362388 | 10437935(−) | T/C | rs377578357 | 10436075(+) | C/T |
| rs28362386 | 10438086(−) | G/A | rs371880025 | 10432278(+) | A/G |
| rs28362384 | 10438106(−) | C/T | rs375790950 | 10433855(+) | C/T |
| rs28362383 | 10438119(−) | G/C | rs377240327 | 10433966(+) | A/G |
| rs193283609 | 10438139(+) | A/G | rs370929260 | 10437048(+) | C/T |
| rs3771117 | 10438246(−) | C/T | rs61733045 | 10436111(+) | C/T |
| rs185506311 | 10438287(+) | C/T | rs369100609 | 10434156(+) | C/T |
| rs140938192 | 10438596(+) | A/G | rs111239078 | 10437158(+) | C/T |
| rs59173521 | 10438633(+) | C/T | rs377151038 | 10434136(+) | A/G |
| rs13401475 | 10438670(+) | A/G | rs371947722 | 10434555(+) | A/G |

II. COLORECTAL CANCER

Colorectal cancer refers to a cancer that forms in the tissues of the colon or rectum, with an estimation of 102,480 and 40,340 new cases diagnosed in 2013 in the United States, respectively. About 50,830 will die of colorectal cancer in 2013 in the United States according to the National Cancer Institute. It is the fourth most common cancer in men, after skin, prostate, and lung cancer. It is also the fourth most common cancer in women, after skin, breast, and lung cancer. Recent rapid declines in colorectal cancer incidence rates have largely been attributed to increases in screening that can detect and allow the removal of precancerous polyps (Siegel et al., 2013). The colon and rectum are parts of the digestive system, which plays a fundamental role in absorption of nutrients, minerals, water and others. They form a long, muscular tube called the large intestine (also called the large bowel), which receives partly digested food coming from the small intestine. The colon is the first 4 to 5 feet of the large intestine, and the rectum is the last several inches. The colon is the longest part of the large intestine and is divided in four different parts: ascending colon, transverse colon, descending colon, and sigmoid colon. The ascending colon, which is connected to the small intestine by the cecum, travels up the right side of the abdomen. The transverse colon crosses the abdomen side-to-side hanging off the stomach. The descending colon goes down the left abdomen and continues until a short curve at the end of the organ known as the sigmoid colon, which ends just before the rectum. The function of the colon is to remove water, salt, and some nutrients from the remaining food and turn the rest into solid waste or stool. The stool, which is temporally stored, passes from the colon into the rectum and then out of the body through the anus.

Colorectal cancer is a disease in which cells in the colon or rectum become abnormal and divide without control, forming a mass called a tumor. The majority of colorectal cancers are adenocarcinomas, which develop from benign polyps known as adenomas (Stewart et al., 2006). Colon polyps are normal growths that form a small protuberance on the inside lining of the upper part of the large intestine (colon or rectum). Surgical removal of adenomas by a procedure called colonoscopy is associated with a 75%-90% lower risk of colorectal cancer, as evidenced by a prospective observational study (Winawer et al., 1993). Studies from patients undergoing colonoscopy suggests that a sizable fraction of the general population's risk for colorectal cancer resides in individuals who develop colorectal neoplasia or colorectal adenomatous polyps (Thompson and Gerner, 2009). Most colon polyps are harmless, but some can progress to invasive cancer (Kronborg and Fenger, 1999; Martinez et al., 2001). Colon polyps found in the early stages can usually be removed safely and completely by a colonoscopy surgical procedure. There are three main types of colon polyps: hyperplastic, inflammatory and adenomatous or adenomas. Hyperplastic polyps occur most often in the descending colon and rectum. Larger, right-sided hyperplastic polyps may become cancerous. Inflammatory polyps usually result from ulcerative colitis and are not a major cancer risk. There are three types of adenomatous polyps or adenomas: villous, tubular and tubulovillous. They can be pedunculated with an elongated stalk of tissue supported with a peduncle or sessile, which lacks a stalk, known as cauliflower-like appearance or flat adenomas. Tubular adenomas are the most common (75%), least likely to develop in colorectal cancer, and may occur everywhere in the colon often on a stalk. Villous adenomas are more likely to become cancerous, often sessile, located in the rectal area, less well differentiated, and account for about 10% of adenomas. The tubulovillous adenomas are 15% of adenomas, and the degree of villous component is correlated with premalignant risk.

According to the model of colon tumorigenesis proposed by Fearon and Vogelstein in 1990, colorectal cancer develops as a multistep process that involves the progression from normal mucosa to small and then large adenomas leading to invasive cancer and metastasis (Fenoglio and Lane, 1974; Morson, 1974; Fearon and Vogelstein, 1990). In support of this widely accepted view, subjects who were negative for adenoma at baseline were followed for an average of 5.3 years and no cancers and low rates of any colorectal adenoma (16.0%) or advanced colorectal cancer (1.3%) were confirmed (Imperiale et al., 2008). This is in contrast to the risk observed in patients who had previously undergone resection for a colorectal adenoma (postpolypectomy patients), which reported rates of any colorectal adenoma (46.7%), advanced colorectal adenomas (11.2%), and invasive cancers (0.6%) with a mean time of follow-up of four years (Martinez et al., 2009). A large polyp prevention trial found that recurrent polyp size and risk of colorectal cancer was strongly related to polyp size determined at entry into the trial (Baron et al., 1999). Risk increases sizably with the detection of more-advanced colorectal adenomas at screening and with the severity of clinical and histological findings at endoscopy examination. Conversely, lack of colorectal adenomas at screening is associated with very low risk for colorectal cancer (Thompson and Gerner, 2009; Martinez et al., 2009; Lieberman et al., 2007). These observations suggested a modification of the molecular multistep process involved in the original polyp-carcinoma sequence. Based on evidence for monoclonal derivation of cancer and an understanding that the neoplastic cells in the initial polyp were removed at the entry colonoscopy, it would be expected that new recurrent polyp size would be normally distributed to reflect stochastic events in carcinogenesis and be independent of initial polyp size (Gerner et al., 2003). The actual model proposed by Martinez and collaborators (Martinez et al., 2001) predicted that carcinogenesis resulting from certain initiating events (e.g., chemical carcinogens and genetic rick factors) and the responses to chemoprevention strategies are influenced by genetic variability. The model is consistent with APC as being an early genetic alteration in colon carcinogenesis, which is muted in essentially all polyps (Iwamoto et al., 2000). Subsequent cancer risk is influenced by variability in APC or other downstream genetic factors among individuals (Gerner et al., 2003).

Between 20% and 35% of the population over the age of 50 years will present with a colorectal adenoma in their lifetime, with 20%-50% of those individuals experiencing separate new adenomas, or metachronous occurrence(s), of colorectal adenomas at follow-up examinations (Thompson and Gerner, 2009). It is estimated that only 2%-5% of sporadic colorectal adenomas have the potential to progress to malignancy. Thus, one of the most relevant risk factors for colorectal cancers in clinical practice is the development of colorectal adenomas, particularly if colorectal adenoma formation is persistent (Thompson and Gerner, 2009). Regular screening for colon polyps helps prevent colon cancer, which is often fatal when it is found in later stages. The use of colonoscopy for the identification of colorectal adenomas and subsequent surveillance in individuals who screen positive for colorectal adenoma has resulted in extensive use of endoscopy, contributing to increased costs and excess risk from numerous procedures (Thompson and Gerner, 2009).

Recommendations of follow-up intervals for patients after polypectomy have been establish by the American Cancer Society, the U.S. Multi-Society Task Force on Colorectal Cancer, and the American College of Radiology (Levin et al., 2008). The guidelines, which aid in decision-making regarding follow-up intervals, establish a three group risk-stratification: 1) High-risk with 3-year follow-up, 2) Low-risk group with 5-10-year follow-up, and 3) Average-risk group with 10-year follow-up. The risk-stratification guidelines are based on the clinical and histologic characteristics of the colorectal adenoma removed at baseline and include adenoma size, histology, degree of dysplasia, and multiplicity (Winawer et al., 2006). Overall, colorectal cancer is potentially preventable with colonoscopy screening, especially considering the potential prevention benefit of colorectal adenoma removal, as well as both the modification of diet and lifestyle factors, and the use of chemoprevention strategies (Thompson and Gerner, 2009; Chan and Giovannucci, 2010; Blackburn et al., 2010).

A. Molecular Pathways of Colorectal Cancer

Recent studies recognized that colorectal cancers can be classified by their molecular characteristics. These molecular features include chromosomal instability (CIN), microsatellite instability (MSI), and hypermethylation of a set of select genes known as CpG Island Methylator Phenotype (CIMP). CIN tumors account for approximately 80% of the colorectal cancers in which genetic instability drives the adenoma-carcinoma sequence. MSI is detected in about 15%-20% of all colorectal cancers and it is likely preceded by CIMP. Some colon cancers lack both MSI and CIN (Georgiades et al., 1999). A specific pathway of intense DNA hypermethylation was discovered and called the CIMP phenotype (Toyota et al., 1999). This finding has been corroborated by Cheng and collaborators where they reported an inverse relationship between CIN and CIMP, suggesting that they are two distinct mechanisms of generating molecular diversity that rarely overlap (Cheng et al., 2008). Finally, 3% of MSI cases are associated with Lynch syndrome, which is caused by germline mutations in a DNA mismatch repair (MMR) gene, accompanied by loss of the wild-type allele through a loss of heterozygosity (LOH) event or methylation, which explains the apparent overlap between MSI and CIN. The other 12% are caused by sporadic, acquired hypermethylation of the promoter of the MLH1 gene, which occurs in tumors with the CIMP phenotype (Herman et al., 1998; Boland and Goel, 2010). MSI can be considered to be a consequence of either CIMP or Lynch syndrome in addition to the loss of the wild-type copy of the MMR gene (Boland et al., 2009). Issa and collaborators suggested a new view of colorectal cancer development (Issa, 2008). Instead of the linear multistep model of colorectal carcinogenesis progression proposed by Fearon and Volgestein (Fearon and Vogelstein, 1990), sporadic colorectal cancer seems to arise from (at least) three distinct parallel modes. The first and second pathways are the most homogeneous, with clear distinctions in precursor lesions (serrated vs. tubular adenomas), genetics (BRAF vs. APC and p53 mutations, MSI vs. CIN), epigenetics (CIMP positive vs. negative) and outcome (good vs. average). The third pathway is more heterogeneous or perhaps incompletely understood. It may arise mostly from villous adenomas, but perhaps also from serrated adenomas. It has a different form of CIMP, predominant KRAS but occasional BRAF mutations, usually lacks CIN, and has a worse prognosis, with apparently lower responsiveness to chemotherapy. The prevalence of the first pathway is estimated at 10% to 20%, the second is 50% to 70%, and the third is 10% to 30%.

B. Polyamines and Colorectal Cancer

Polyamines (putresine, spermidine, and spermine) control gene expression at the transcriptional and post transcriptional levels, implicating them as potential functional regulators of cancer progression (Xie et al., 1997; Russell and Snyder, 1968). An association between high levels of polyamines and cancer was first reported in the late 1960s by Russell and Snyder (Casero and Marton, 2007), who measured high levels of ODC1 activity in regenerated rat liver and in several human cancers. Studies have demonstrated that colorectal cancers are associated with elevated levels of polyamines (Xie et al., 1997; Thomas and Thomas, 2001). Polyamines are unique because of their flexible polycationic nature that allows them to bind electrostatically to negatively charged macromolecules, including nucleic acids, acidic proteins, and membranes (Larque et al., 2007). Complex regulation controls intracellular polyamine pool sizes through combined actions of de novo synthesis, retro-conversion, degradation, efflux, and uptake of polyamines. The major sources of exogenous polyamines, transported into gastro-intestinal tissue by endocytic and solute transport mechanisms, are diet and intestinal luminal bacteria (Uemura et al., 2010; Uemura et al., 2008). Polyamines are synthesized through the action of the enzyme ornithine decarboxylase (ODC1), the first enzyme in polyamine biosynthesis, which catalyzes the formation of putrescine from ornithine. Putrescine is subsequently converted into spermidine through the actions of S-adenosylmethionine decarboxylase 1 (AMD1) and spermidine synthase (SRM). Spermidine is then converted into spermine by AMD1 and spermine synthase (SMS). The aminopropyl groups that form the higher polyamines come from the decarboxylation of S-adenosylmethionine (SAM) by AMD1 producing decarboxylated SAM (dcSAM). Spermidine/spermine $N^1$-acetyltransferase (SAT1) adds one terminal acetyl group to spermidine and one or two terminal acetyl groups to spermine, which subsequently promotes the export of acetylated polyamines by the SLC3A2 transporter (Tabor et al., 1980). Spermine oxidase (SMO) converts non-acetylated spermine to spermidine. Acetylpolyamine oxidase (PAO) also aids in polyamine homeostasis by converting acetylated spermidine and spermine back to putrescine, using monoacetylated spermidine as an intermediary (Xie et al., 1997) (FIG. 1).

Polyamines regulate important cellular processes, including cell proliferation and viability. Genetic evidence indicates that polyamines are required for optimal growth of bacteria (Balasundaram et al., 1991) and are essential for aerobic growth in yeast (Lux et al., 1980). The cellular functions of polyamines also include intestinal mucosal maturation and cell migration (McCormack and Johnson, 2001; Basuroy and Gerner, 2006). Polyamines have been shown to influence transcription, RNA stabilization, translation and translational frameshifting, and protein degradation (Childs et al., 2003; Janne et al., 2004; Pegg, 1988; Pegg, 2006; Pegg, 2009, Shantz and Levin, 2007; Igarashi and Kashiwagi, 2000; Matsufuji et al., 1995; Meyskens et al., 2008).

Polyamine metabolism is a validated pathway for chemoprevention of colorectal cancer by a prospective, randomized, placebo-controlled, double-blind clinical trial using low doses of difluoromethylornithine (DFMO)/sulindac and an on-going clinical trial on FAP (Identifier: NCT01483144). The combination treatment was associated with a 70% reduction of all, and over a 90% reduction of advanced and/or multiple colorectal adenomas in patients with prior colon polyps (Erdman et al., 1999). DFMO, an irreversible suicide inhibitor of the ODC enzyme, inhibits MYC-dependent carcinogenesis in rodent models, suppressing intestinal polyamine content and tumorigenesis in the Apc/Min mouse (Ignatenko et al., 2006; Giardiello, 1997). Genetic studies corroborate epidemiological studies that have documented elevated ODC expression and activity during colorectal tumorigenesis (Luk and Baylin, 1984; Pendeville et al., 2001). ODC plays an essential role in murine development, and proper homeostasis of polyamine pools appears to be required for cell survival prior to gastrulation, since Odc1 knockout is lethal in murine embryos 3.5 days after fertilization (Bailey et al., 2010). In addition, the importance of ODC1 in tumorigenesis has been proven by both the haploinsufficiency for Odc1, which modifies mouse skin tumor susceptibility, and with the use of DFMO alone in skin and prostate chemoprevention trials (Guo et al., 2005; Simaneau et al., 2001; Simoneau et al., 2008; Rounbehler et al., 2009). In the MYCN-induced neuroblastoma mouse model, DFMO treatment, but not Odc heterozygosity, impairs lymphoma malignancy development (George et al., 2005). A clinical trial is on-going in human patients with neuroblastoma (Identifier: NCT01586260). The causative role of ODC in carcinogenesis has been observed upon overexpression of ODC1 by transfection in vitro and in vivo in transgenic mice (Hayes et al., 2006; Feith et al., 2006). Overexpression of the intracellular noncompetitive ODC1 inhibitor antizyme in transgenic mice has been shown to reduce carcinogenesis, since that antizyme targets ODC1 for proteasome degradation and decreases polyamine levels (Feith et al., 2001; Tang et al., 2004; Babbar et al., 2003).

The mechanism underlying the relationship between aspirin use and the polyamine pathway with decreased new adenoma formation are not exactly known, but it appears to involve the action of aspirin and others non-steroidal anti-inflammatory drugs (NSAIDs) on polyamine catabolism and export. NSAIDs transcriptionally activate the SAT1 enzyme which, by acetylation of spermidine and spermine, targets both of them to be excreted by an SLC3A2-dependent arginine/putrecine antiporter (Tabor et al., 1980; Babbar et al., 2006; Ignatenko et al., 2008; Paz et al., 2014).

The mechanisms by which polyamines elicit their tumorigenic effects and the molecular mechanisms to explain the clinical outcome remains poorly understood (Sporn et al., 2008; Zell et al., 2010; Fultz and Gerner, 2002).

C. Ornithine Decarboxylase and Colorectal Cancer

Major oncogenic pathways are involved in regulation of ODC1 transcription. ODC1 is regulated by the WNT signaling pathway, one of the major cascades governing epithelial development (Mishra et al., 2005; Groden et al., 1991). The adenomatous polyposis coli (ARC) tumor suppression gene is a component of the WNT cascade, and is mutated or lost in the germline of individuals with familial adenomatous polyposis (FAP), a heritable form of colon cancer (Kinzler et al., 1991; He et al., 1998). APC is also mutated in almost 90% of human colon cancers and 30% of melanoma skin cancers (Iwamoto et al., 2000). ODC1 expression and polyamine content are elevated in intestinal tissue, and a specific inhibitor of ODC1 suppresses intestinal carcinogenesis in the $Apc^{Min/+}$ mouse, an animal model for FAP (Ignatenko et al., 2006). APC mutation is an early event in colon carcinogenesis, and is, therefore, considered to be an initiating event. In this model, mutated APC led to a decrease in antizyme and SAT1 expression, indicating that APC controls the polyamine metabolic pathway in the colon. In carcinogenic tissue, loss of APC and dysregulation of the WNT pathway leads to increased expression of the c-MYC oncogene and other growth-related genes (Mishra et al., 2005; Kinzler et al., 1991; Reya and Clever, 2005; Kern et al., 1991; Moser et al., 1990). APC mutation prevents GSK-3β phosphorylation of β-catenin, which would normally lead to its proteosomal degradation. Mutated APC leads to stabilization and accumulation of β-catenin in the nucleus, where it forms a complex with the TCF/LEF (T-cell factor/lymphoid-enhancing factor) transcription factor, to activate specific growth-related genes to alter gene expression, such as c-MYC and cyclin D1 (Reya and Clever, 2005; Kern et al., 1991). Germ-line and somatic mutation within different regions of the APC gene are associated with different disease phenotypes, with a hot spot in the β-catenin binding site. Mutations in codons 1403 to 1578 are associated with extracolonic manifestation, whereas mutations in codons 78 to 167 and codons 1581 2843 are seen in attenuated FAP. The roles of different deletions of the APC gene have been studied with genetically altered mouse models. The C57BL/6 Min (multiple intestinal neoplasia) mouse was the first model developed, which harbors a stop codon at codon 850 on the APC gene (Oshima et al., 1996). Subsequently other mouse models harboring different APC deletions have been reported, each one with a different phenotype (Fodde, 2002; Boyd and Farnham, 1999). Genetic alteration of other gene (such as COX-1, COX-2, NOS2, P53, MLH1, MLH2, SMAD4, K-RAS, and others), either in combination with mutated APC or alone, have also been reported to affect colorectal cancer and may be a better model of sporadic colon carcinogenesis (Gerner et al., 2003).

The modification of the colorectal carcinogenesis model proposed by Fearon and Volgestein from Martinez and collaborators predicts that downstream of APC signaling pathways, the colorectal risk is affected by genetic variability of other genetic factors that confer different responses to chemoprevention strategies among individuals (Martinez et al., 2001; Fearon and Vogelsten, 1990; Gerner et al., 2003). In addition, CIN, MSI, and CIMP are pathways of colorectal cancer in which genetic and epigenetics changes are important in the progression from normal to neoplastic colonic tissue. Genetic variability in these alterations, or downstream mediators of these early genetic and epigenetic alterations have an important role in this progression. Loss of APC function leads to increased expression of the c-MYC oncogene, which is required for the proliferation of normal cells, and its aberrant expression can lead to uncontrolled growth and cancer (Mishra et al., 2005; Reya and Clevers, 2005; Hermeking, 2003; Bello-Fernandez et al., 1993). c-MYC encodes a transcription factor that has been demonstrated to directly target the ODC1 gene (Pena et al., 1993; Kumar et al., 2009). ODC1 expression is increased in intestinal tissues of the min mouse model supporting the evidence that APC affects the expression of ODC (Ignatenko et al., 2006). Subsequent work showing that conditional expression of wild-type APC suppresses ODC expression in a MYC-dependent manner in human colon tumor cells supports the hypothesis that ODC is a modifier of APC-dependent tumorigenesis (Mishra et al., 2005). In addition, studies using the min mouse model with a conditional deletion of c-MYC in the intestinal and colonic mucosa showed that c-MYC plays an important role in the development of intestinal tumors via increased proliferation and suppressed apoptosis, without an apparent effect on normal intestinal mucosa (Giardiello, 1997).

ODC1 has three c-MYC-binding elements (E-boxes) in the region from −400 to +400 bp relative to the transcription start site (TSS). Polyamine-induced nuclear c-MYC interacts with MAX, and this complex binds to the E-box sequence (CACGTG) to activate transcription of target genes, such as ODC1, thus accelerating polyamine biosynthesis (Pena et al., 1993; Kumar et al., 2009; Guo et al., 2000; Walhout et al., 1998; Walhout et al., 1997; Nilsson et al., 2004). The transcription repressor MAD1/MAX also binds to these elements to regulate the transcription level of ODC1 in proliferative cells (Pegg, 2009; Zell et al., 2009). ODC1 promoter activity is influenced by cooperative interactions involving these neighboring E-boxes (Martinez et al., 2003). Since ODC1 expression has been linked to cancer development, individuals with specific genetic variability may exhibit an increased predisposition for colon polyp development. The relationship between ODC1 polymorphism and the risk of adenoma recurrence has been assessed in participants of a large randomized, double-blind wheat bran fiber colon cancer prevention trial at the Arizona Cancer Center in Tucson, Ariz. (Martinez et al., 2001). A single nucleotide polymorphism (rs2302615) exists in intron 1 of human ODC1 between two E-boxes with a G/A variation located 316 nucleotides downstream of the transcription start site (Walhout et al., 1998; Martinez et al., 2003; Barry et al., 2006; Hubner et al., 2008; Hughes et al., 2010). A substantial and statistically significant effect of the ODC1 +316 SNP on risk of adenoma recurrence has been found, especially in aspirin users, with a strong correlation between recurrent polyp size and risk of colorectal cancer (Walhout et al., 1998; Martinez et al., 2003; Barry et al., 2006; Hubner et al., 2008; Hughes et al., 2010). The risk of adenoma recurrence was found to be almost half in AA homozygous individuals who reported taking aspirin (Barry et al., 2006). Barry and collaborators (Hubner et al., 2008) in the Aspirin/Folate Polyp Prevention Study found a non-statistically significant association between ODC1 genotype and colorectal cancer recurrence in individuals randomly assigned to placebo or aspirin treatment (81 or 325 mg daily). This study also found that ODC1 genotype modified the effect of aspirin on adenoma risk. Although aspirin treatment had no protective effect among subjects with a GG genotype, it was associated with a statistically significant reduced risk of any adenoma among subjects with at least one A allele. Hubner and collaborators (Hughes et al., 2010) in a United Kingdom Colorectal Adenoma Prevention reported that the rare ODC1 +316 AA homozygotes had reduced colorectal adenoma recurrence risk, with an additional lower recurrence risk if aspirin was administered. At the same time a recent study from Hughes and collaborators reported no correlation between ODC1 +316 genotype and colorectal cancer in a Czech Republic case control series with no data on aspirin or stage of disease (Zell et al., 2012). A population-based study of 400 of stage I-III colorectal cancer cases from the California Irvine Gene-Environment Study of Familial Colorectal Cancer reported that the specific outcome of colorectal cancer patients is dependent on ODC1 +316 genotype with a higher colorectal cancer-specific risk of death for individuals with ODC1 GA/AA genotypes (Martinez et al., 2003). In addition, a statistically significant interaction has been found between ODC1 +316 genotype and DFMO/sulindac treatment with respect to adenoma recurrence, but not with any polyamine levels. Specifically, individuals homozygous for the G-allele had lower risk of adenoma recurrence after treatment than GA/AA individuals (Fultz and Gerner, 2002). Experiments with the ODC1 +316 SNP promoter-reporter luciferase constructs transfected into the colon cancer cell lines showed that the A-allele drives more luciferase than the G-allele (Walhout et al., 1998; Martinez et al., 2003). In co-transfection experiments, the A-allele presents increased binding of E-box transcription factors, such as MYC and MAD, compared to the G-allele (Walhout et al., 1998; Martinez et al., 2003). Also, a significant metachronous adenoma risk reduction was detected between dietary polyamine intake groups, as well as meat consumption, and DFMO/sulindac treatment (Zell et al., 2007; Raj et al., 2013; Vargas et al., 2012). Those studies validated previous associations between dietary polyamine intake and risk of colorectal adenoma polyps from other clinical trials and confirm a modifiable dietary risk factor for colorectal adenoma (Campello et al., 2010).

III. DIFLUOROMETHYLORNITHINE (DFMO)

DFMO, also known as eflornithine, has the following chemical designation: 2-(difluoromethyl)-dl-ornithine. It is an enzyme-activated irreversible inhibitor of ornithine decarboxylase (ODC), the rate limiting enzyme of the polyamine biosynthetic pathway. As a result of this inhibition of polyamine synthesis, the compound is effective in preventing cancer formation in many organ systems, inhibiting cancer growth, and reducing tumor size. It also has synergistic action with other antineoplastic agents.

DFMO decreases APC-dependent intestinal tumorigenesis in mice (Erdman et al., 1999). Oral DFMO administered daily to humans inhibits ODC enzyme activity and polyamine contents in a number of epithelial tissues (Love et al., 1993; Gerner et al., 1994; Meyskens et al., 1994; Meyskens et al., 1998; Simoneau et al., 2001; Simoneau et al., 2008). DFMO, in combination with the non-steroidal anti-inflammatory drug (NSAID) sulindac, has been reported to markedly lower the adenoma recurrence rate among individuals with colonic adenomas when compared to placebos in a randomized clinical trial (Meyskens et al., 2008).

DFMO was originally synthesized by Centre de Recherche Merrell, Strasbourg. Current FDA approvals include:
a) African sleeping sickness. High dose systemic IV dosage form—not marketed (Sanofi/WHO); and
b) Hirsutis (androgen-induced excess hair growth) topical dosage form.
No oral formulations are currently approved.

DFMO and its use in the treatment of benign prostatic hypertrophy are described in two patents, U.S. Pat. Nos. 4,413,141, and 4,330,559. U.S. Pat. No. 4,413,141 describes DFMO as being a powerful inhibitor of ODC, both in vitro and in vivo. Administration of DFMO causes a decrease in putrescine and spermidine concentrations in cells in which these polyamines are normally actively produced. Additionally, DFMO has been shown to be capable of slowing neoplastic cell proliferation when tested in standard tumor models. U.S. Pat. No. 4,330,559 describes the use of DFMO and DFMO derivatives for the treatment of benign prostatic hypertrophy. Benign prostatic hypertrophy, like many disease states characterized by rapid cell proliferation, is accompanied by abnormal elevation of polyamine concentrations. The treatment described within this reference can be administered to a patient either orally or parenterally.

DFMO can potentially be given continuously with significant anti-tumor effects. This drug is relatively non-toxic at low doses of 0.4 $g/m^2$/day to humans while producing inhibition of putrescine synthesis in tumors. Studies in a rat-tumor model demonstrate that DFMO infusion can produce a 90% decrease in tumor putrescine levels without suppressing peripheral platelet counts.

Side effects observed with DFMO include effects on hearing at high doses of 4 g/m$^2$/day that resolve when it is discontinued. These effects on hearing are not observed at lower doses of 0.4 g/m$^2$/day when administered for up to one year (Meyskens et al., 1994). In addition, a few cases of dizziness/vertigo are seen that resolve when the drug is stopped. Thrombocytopenia has been reported predominantly in studies using high "therapeutic" doses of DFMO (>1.0 g/m$^2$/day) and primarily in cancer patients who had previously undergone chemotherapy or patients with compromised bone marrow. Although the toxicity associated with DFMO therapy are not, in general, as severe as other types of chemotherapy, in limited clinical trials it has been found to promote a dose-related thrombocytopenia. Moreover, studies in rats have shown that continuous infusion of DFMO for 12 days significantly reduces platelet counts compared with controls. Other investigations have made similar observations in which thrombocytopenia is the major toxicity of continuous i.v. DFMO therapy. These findings suggest that DFMO may significantly inhibit ODC activity of the bone marrow precursors of megakaryocytes. DFMO may inhibit proliferative repair processes, such as epithelial wound healing.

A phase III clinical trial assessed the recurrence of adenomatous polyps after treatment for 36 months with difluoromethylornithine (DFMO) plus sulindac or matched placebos. Temporary hearing loss is a known toxicity of treatment with DFMO, thus a comprehensive approach was developed to analyze serial air conduction audiograms. The generalized estimating equation method estimated the mean difference between treatment arms with regard to change in air conduction pure tone thresholds while accounting for within-subject correlation due to repeated measurements at frequencies. Based on 290 subjects, there was an average difference of 0.50 dB between subjects treated with DFMO plus sulindac compared with those treated with placebo (95% confidence interval, −0.64 to 1.63 dB; P=0.39), adjusted for baseline values, age, and frequencies. In the normal speech range of 500 to 3,000 Hz, an estimated difference of 0.99 dB (−0.17 to 2.14 dB; P=0.09) was detected. Dose intensity did not add information to models. There were 14 of 151 (9.3%) in the DFMO plus sulindac group and 4 of 139 (2.9%) in the placebo group who experienced at least 15 dB hearing reduction from baseline in two or more consecutive frequencies across the entire range tested (P=0.02). Follow-up air conduction done at least six months after the end of treatment showed an adjusted mean difference in hearing thresholds of 1.08 dB (−0.81 to 2.96 dB; P=0.26) between treatment arms. There was no significant difference in the proportion of subjects in the DFMO plus sulindac group who experienced clinically significant hearing loss compared with the placebo group. The estimated attributable risk of ototoxicity from exposure to the drug was 8.4% (95% confidence interval, −2.0% to 18.8%; P=0.12). There was a <2 dB difference in mean threshold for patients treated with DFMO plus sulindac compared with those treated with placebo. The results of this study were discussed in greater detail in McLaren et al., 2008, which is incorporated herein by reference in its entirety.

IV. NSAIDs

NSAIDs are anti-inflammatory agents that are not steroids. In addition to anti-inflammatory actions, they have analgesic, antipyretic, and platelet-inhibitory actions. They are used primarily in the treatment of chronic arthritic conditions and certain soft tissue disorders associated with pain and inflammation. They act by blocking the synthesis of prostaglandins by inhibiting cyclooxygenase, which converts arachidonic acid to cyclic endoperoxides, precursors of prostaglandins. Inhibition of prostaglandin synthesis accounts for their analgesic, antipyretic, and platelet-inhibitory actions; other mechanisms may contribute to their anti-inflammatory effects. Certain NSAIDs also may inhibit lipoxygenase enzymes or phospholipase C or may modulate T-cell function (AMA Drug Evaluations Annual, 1814-5, 1994).

The nonsteroidal anti-inflammatory drugs (NSAIDs), including aspirin, ibuprofen, piroxicam (Reddy et al., 1990; Singh et al., 1994), indomethacin (Narisawa, 1981), and sulindac (Piazza et al., 1997; Rao et al., 1995), effectively inhibit colon carcinogenesis in the AOM-treated rat model. NSAIDs also inhibit the development of tumors harboring an activated Ki-ras (Singh and Reddy, 1995). NSAIDs appear to inhibit carcinogenesis via the induction of apoptosis in tumor cells (Bedi et al., 1995; Lupulescu, 1996; Piazza et al., 1995; Piazza et al., 1997b). A number of studies suggest that the chemopreventive properties of the NSAIDs, including the induction of apoptosis, is a function of their ability to inhibit prostaglandin synthesis (reviewed in DuBois et al., 1996; Lupulescu, 1996; Vane and Botting, 1997). Studies, however, indicate that NSAIDs may act through both prostaglandin-dependent and -independent mechanisms (Alberts et al., 1995; Piazza et al., 1997a; Thompson et al., 1995; Hanif, 1996). Sulindac sulfone, a metabolite of the NSAID sulindac, lacks COX-inhibitory activity yet induces apoptosis in tumor cells (Piazza et al., 1995; Piazza et al., 1997b) and inhibits tumor development in several rodent models of carcinogenesis (Thompson et al., 1995; Piazza et al., 1995, 1997a).

Several NSAIDs have been examined for their effects in human clinical trials. A phase IIa trial (one month) of ibuprofen was completed and even at the dose of 300 mg/day, a significant decrease in prostoglandin E$_2$ (PGE$_2$) levels in flat mucosa was seen. A dose of 300 mg of ibuprofen is very low (therapeutic doses range from 1200-3000 mg/day or more), and toxicity is unlikely to be seen, even over the long-term. However, in animal chemoprevention models, ibuprofen is less effective than other NSAIDs.

A. Sulindac and its Major Metabolites, Sulindac Sulfone and Sulindac Sulfide

Sulindac is a non-steroidal, anti-inflammatory indene derivative with the following chemical designation; (Z)-5-fluoro-2-methyl-1-((4 (methylsulfinyl)phenyl)methylene) 1H-indene-3-acetic acid (Physician's Desk Reference, 1999). The sulfinyl moiety is converted in vivo by reversible reduction to a sulfide metabolite and by irreversible oxidation to a sulfone metabolite (exisulind). See U.S. Pat. No. 6,258,845, which is incorporated herein by reference in its entirety. Sulindac, which also inhibits Ki-ras activation, is metabolized to two different molecules that differ in their ability to inhibit COX, yet both are able to exert chemopreventive effects via the induction of apoptosis. Sulindac sulfone lacks COX-inhibitory activity, and most likely facilitates the induction of apoptosis in a manner independent of prostaglandin synthesis. Available evidence indicates that the sulfide derivative is at least one of the biologically active compounds. Based on this, sulindac may be considered a prodrug.

Sulindac (Clinoril®) is available, for example, as 150 mg and 200 mg tablets. The most common dosage for adults is 150 to 200 mg twice a day, with a maximal daily dose of 400 mg. After oral administration, about 90% of the drug is absorbed. Peak plasma levels are achieved in about 2 h in fasting patients and 3 to 4 h when administered with food. The mean half-life of sulindac is 7.8 h; the mean half-life of the sulfide metabolite is 16.4 h. U.S. Pat. Nos. 3,647,858 and 3,654,349 cover preparations of sulindac, both are incorporated by reference herein in their entireties.

Sulindac is indicated for the acute and long-term relief of signs and symptoms of osteoarthritis, rheumatoid arthritis, ankylosing spondylitis, acute gout, and acute painful shoulder. The analgesic and anti-inflammatory effects exerted by sulindac (400 mg per day) are comparable to those achieved by aspirin (4 g per day), ibuprofen (1200 mg per day), indomethacin (125 mg per day), and phenylbutazone (400 to 600 mg per day). Side effects of sulindac include mild gastrointestinal effects in nearly 20% of patients, with abdominal pain and nausea being the most frequent complaints. CNS side effects are seen in up to 10% of patients, with drowsiness, headache, and nervousness being those most frequently reported. Skin rash and pruritus occur in 5% of patients. Chronic treatment with sulindac can lead to serious gastrointestinal toxicity such as bleeding, ulceration, and perforation.

The potential use of sulindac for chemoprevention of cancers, and in particular colorectal polyps, has been well studied. Two recent U.S. patents (U.S. Pat. Nos. 5,814,625 and 5,843,929) detail potential chemopreventive uses of sulindac in humans. Both patents are incorporated herein in their entireties. Doses of sulindac claimed in U.S. Pat. No. 5,814,625 range from 10 mg to 1500 mg per day, with preferred doses of 50 mg to 500 mg per day. However, at the higher doses, the biggest problem with the use of sulindac as a single agent in chemoprevention is its well-known toxicities and moderately high risk of intolerance. The elderly appear to be especially vulnerable, as the incidence of side effects is higher in those over the age of 60. It is noted that this age group is most likely to develop colorectal cancer, and therefore, most likely to benefit from chemoprevention.

B. Combinations of NSAIDs

Combinations of various NSAIDs are also used for various purposes. By using lower doses of two or more NSAIDs, it is possible to reduce the side effects or toxicities associated with higher doses of individual NSAIDs. For example, in some embodiments, sulindac may be used together with celecoxib. In some embodiments, the one or both of the NSAIDS are selective COX-2 inhibitors. Examples of NSAIDS that may be used either alone or in combination include, but are not limited to, ibuprofen, naproxen, fenoprofen, ketoprofen, flurbiprofen, oxaprozin, indomethacin, sulindac, etodolac, diclofenac, piroxicam, meloxicam, tenoxicam, droxicam, lornoxicam, isoxicam, mefenamic acid, meclofenamic acid, flufenamic acid, tolfenamic acid, celecoxib rofecoxib valdecoxib parecoxib, lumiracoxib, and etoricoxib.

V. DFMO/SULINDAC COMBINATION THERAPY

Preclinical studies of chemoprevention drugs given in combination at low doses show remarkable efficacy in preventing adenomas with little additional toxicities, suggesting a strategy to improve risk-to-benefit ratios for preventing recurrent adenomas.

As noted above, the Min (multiple intestinal neoplasia) mouse, which shares a mutated APC/apc genotype with FAP, serves as a useful experimental animal model for human FAP patients (Lipkin, 1997). The Min mouse can develop greater than 100 gastrointestinal adenomas/adenocarcinomas throughout the gastrointestinal tract by 120 days of life leading to GI bleeding, obstruction, and death. A combination therapy of DFMO and sulindac was shown to be effective in reducing adenomas in these mice (U.S. Pat. No. 6,258,845; Gerner and Meyskens, 2004).

VI. POLYMORPHISM ANALYSIS

The genotype of ODC1 of a patient can determined using the methods provided below, including the specific methods described in the Examples section. These methods can be further modified and optimized using the principles and techniques of molecular biology as applied by a person skilled in the art. Such principles and techniques are taught, for example, in Small et al. (2002), which is incorporated herein by reference. General methods employed for the identification of single nucleotide polymorphisms (SNPs) are provided below. The reference of Kwok and Chen (2003) and Kwok (2001) provide overviews of some of these methods; both of these references are specifically incorporated by reference.

SNPs relating to ODC1 can be characterized by the use of any of these methods or suitable modification thereof. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or any other biochemical interpretation.

A. DNA Sequencing

A commonly used method of characterizing a polymorphism is direct DNA sequencing of the genetic locus that flanks and includes the polymorphism. Such analysis can be accomplished using either the "dideoxy-mediated chain termination method," also known as the "Sanger Method" (Sanger et al., 1975) or the "chemical degradation method," also known as the "Maxam-Gilbert method" (Maxam et al., 1977). Sequencing in combination with genomic sequence-specific amplification technologies, such as the polymerase chain reaction, may be used to facilitate the recovery of the desired genes (Mullis et al., 1986; European Patent Application 50,424; European Patent Application 84,796; European Patent Application 258,017; European Patent Application. 237,362; European Patent Application. 201,184; U.S. Pat. Nos. 4,683,202; 4,582,788; and 4,683,194), all of the above incorporated herein by reference.

B. Exonuclease Resistance

Other methods that can be employed to determine the identity of a nucleotide present at a polymorphic site use a specialized exonuclease-resistant nucleotide derivative (U.S. Pat. No. 4,656,127). A primer complementary to an allelic sequence immediately 3' to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known, one can determine the specific nucleotide present in the polymorphic site of the DNA.

C. Microsequencing Methods

Several other primer-guided nucleotide incorporation procedures for assaying polymorphic sites in DNA have been described (Komher et al., 1989; Sokolov, 1990; Syvanen 1990; Kuppuswamy et al., 1991; Prezant et al., 1992; Ugozzoll et al., 1992; Nyren et al., 1993). These methods rely on the incorporation of labeled deoxynucleotides to discriminate between bases at a polymorphic site. As the signal is proportional to the number of deoxynucleotides incorporated, polymorphisms that occur in runs of the same nucleotide result in a signal that is proportional to the length of the run (Syvanen et al., 1990).

D. Extension in Solution

French Patent 2,650,840 and PCT Application WO91/02087 discuss a solution-based method for determining the identity of the nucleotide of a polymorphic site. According to these methods, a primer complementary to allelic sequences immediately 3' to a polymorphic site is used. The identity of the nucleotide of that site is determined using labeled dideoxynucleotide derivatives that are incorporated at the end of the primer if complementary to the nucleotide of the polymorphic site.

E. Genetic Bit Analysis or Solid-Phase Extension

PCT Application WO92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here the primer or the target molecule is immobilized to a solid phase.

F. Oligonucleotide Ligation Assay (OLA)

This is another solid phase method that uses different methodology (Landegren et al., 1988). Two oligonucleotides, capable of hybridizing to abutting sequences of a single strand of a target DNA are used. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR, have also been described (Nickerson et al., 1990). Here PCR is used to achieve the exponential amplification of target DNA, which is then detected using the OLA.

G. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

H. Invasive Cleavage Reactions

Invasive cleavage reactions can be used to evaluate cellular DNA for a particular polymorphism. A technology called INVADER® employs such reactions (e.g., de Arruda et al., 2002; Stevens et al., 2003, which are incorporated by reference). Generally, there are three nucleic acid molecules: 1) an oligonucleotide upstream of the target site ("upstream oligo"), 2) a probe oligonucleotide covering the target site ("probe"), and 3) a single-stranded DNA with the target site ("target"). The upstream oligo and probe do not overlap but they contain contiguous sequences. The probe contains a donor fluorophore, such as fluoroscein, and an acceptor dye, such as Dabcyl. The nucleotide at the 3' terminal end of the upstream oligo overlaps ("invades") the first base pair of a probe-target duplex. Then the probe is cleaved by a structure-specific 5' nuclease causing separation of the fluorophore/quencher pair, which increases the amount of fluorescence that can be detected. See Lu et al., 2004. In some cases, the assay is conducted on a solid-surface or in an array format.

I. Other Methods to Detect SNPs

Several other specific methods for polymorphism detection and identification are presented below and may be used as such or with suitable modifications in conjunction with identifying polymorphisms of ODC1 in the present invention. Several other methods are also described on the SNP web site of the NCBI on the World Wide Web at ncbi.nlm.nih.gov/SNP, incorporated herein by reference.

In a particular embodiment, extended haplotypes may be determined at any given locus in a population, which allows one to identify exactly which SNPs will be redundant and which will be essential in association studies. The latter are referred to as 'haplotype tag SNPs (htSNPs)', markers that capture the haplotypes of a gene or a region of linkage disequilibrium. See Johnson et al. (2001) and Ke and Cardon (2003), each of which is incorporated herein by reference, for exemplary methods.

The VDA-assay utilizes PCR amplification of genomic segments by long PCR methods using TaKaRa LA Taq reagents and other standard reaction conditions. The long amplification can amplify DNA sizes of about 2,000-12,000 bp. Hybridization of products to a variant detector array (VDA) can be performed by an Affymetrix High Throughput Screening Center and analyzed with computerized software.

A method called Chip Assay uses PCR amplification of genomic segments by standard or long PCR protocols. Hybridization products are analyzed by VDA, Haluskha et al. (1999), incorporated herein by reference. SNPs are generally classified as "Certain" or "Likely" based on computer analysis of hybridization patterns. By comparison to alternative detection methods, such as nucleotide sequencing, "Certain" SNPs have been confirmed 100% of the time; and "Likely" SNPs have been confirmed 73% of the time by this method.

Other methods simply involve PCR amplification following digestion with the relevant restriction enzyme. Yet others involve sequencing of purified PCR products from known genomic regions.

In yet another method, individual exons or overlapping fragments of large exons are PCR-amplified. Primers are designed from published or database sequences and PCR-amplification of genomic DNA is performed using known conditions. Thermal cycling is performed and resulting PCR-products are analyzed by PCR-single strand conformation polymorphism (PCR-SSCP) analysis, under a variety of conditions, e.g., 5 or 10% polyacrylamide gel with 15% urea, with or without 5% glycerol. Electrophoresis is performed overnight. PCR-products that show mobility shifts are reamplified and sequenced to identify nucleotide variation.

VII. PHARMACEUTICAL FORMULATIONS AND ROUTES OF ADMINISTRATION

The therapeutic compounds of the present disclosure may be administered by a variety of methods, e.g., orally or by injection (e.g., subcutaneous, intravenous, intraperitoneal, etc.). Depending on the route of administration, the active compounds may be coated in a material to protect the compound from the action of acids and other natural conditions that may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

VIII. COMBINATION THERAPY

Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Various combinations may be employed, such as where "A" represents the first agent (e.g., DFMO) and "B" represents a secondary agent (e.g., sulindac), non-limiting examples of which are described below:

A/B/A  B/A/B  B/B/A  A/A/B   A/B/B  B/A/A  A/B/B/B  B/A/B/B
B/B/B/A  B/B/A/B  A/A/B/B  A/B/A/B  A/B/B/A  B/B/A/A
B/A/B/A  B/A/A/B  A/A/A/B  B/A/A/A  A/B/A/A  A/A/B/A

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Materials and Methods

Oligonucleotides.

DNA oligomers were purchased from Eurofins MWG Operon (Table 1). All oligomers were solubilized in double distilled water overnight at 4° C. to an approximate final concentration of 100 µM. Solvated DNA was dialyzed in double distilled water with 3500 Da molecular-weight cutoff membranes overnight at 4° C. to remove any short fragments. Oligomers were heated to 95° C. and the concentrations were measured spectrophotometrically using a Nanodrop 1000 Spectrophotometer by Thermo Fisher Scientific. The ε260 was calculated with the nearest neighbor method (Final concentrations=$(A_{260} \times 10^6)/\varepsilon_{260}$).

TABLE 1

Full oligonucleotide sequences within ODC1 SNP +263

| Name | Sequence | SEQ ID NO: |
|---|---|---|
| Full G | ggagggagggagcgagggcgggagccggggc Gggctgcgggccccgggccccgggcac | 1 |
| Full T | gaagggagggagcgagggcgggagccggggc Tggctgcgggccccgggccccgggcac | 2 |

Uppercase letters show the transition G to T at the ODC +263 location. Underlined bold letters are the guanine repetition that can participate in the formation of the G4.
Note the disruption of one guanine repetition by ODC SNP +263. Each sequence of 58 nucleotides is flanked by three nucleotides.

Circular Dichroism (CD) and Thermal Stability (Tm) Spectroscopy.

Single-stranded DNA samples (5 µM) were diluted in Tris-Acetate buffer (50 mM, pH 7.06), in the presence or absence of different concentrations of KCl or NaCl and/or NSC176327 (C14). Then the samples were heated to 95° C. and slowly cooled to room temperature. For double-stranded conditions, the G-rich and C-rich strands of DNA were annealed by heating the strands to 95° C., rapidly cooling to the strands $T_M$, holding at that temperature for 5 min, and cooling to room temperature at 1° C./min in a Qiagen PCR machine (RotorGene Q Series software). The sample was split to 0 or 100 mM KCl in the presence or absence of 530 ng recombinant human Sp1 protein (Promega, part number E639A) and heated again to the dsDNA annealing temperature, and then allowed to slowly cool again. CD spectra data were recorded on a Jasco-810 spectropolarmeter using a quartz cell with a 1-mm optical path length, with a response time of 1 s. Each sample was processed with three averaged scans within the range of 200 to 350 nm and results were baseline-corrected for signal contributions due to buffer and salts. Thermal melts ($T_{Ms}$) were determined on the Jasco CD instrument, at 263 nm from 4° C. to 90° C. (heating rate of 2° C./min).

EMSA (Electrophoretic Mobility Shift Assay).

DNA oligomers were incubated in Tris-Acetate buffer (50 mM, pH 7.06) containing different concentrations of KCl or NaCl for 1 h at room temperature. The secondary structures of the DNA oligomers were heated at 95° C. for 10 min, and then cooled to room temperature before loading the non-denaturing 12% polyacrylamide gel. Electrophoresis of the DNA was conducted at 217 V in TBE buffer. Following electrophoresis, the gels were stained with Gelstar Nucleic Acid Gel Stain and visualized on a UV-trans illuminator. Image J software (NIH, Bethesda, Md.) was used to semi-quantitate the band density, and those values were converted into percent of the total species.

Plasmids.

ODCJ promoter/intron 1 reporter constructs were prepared from previously published plasmids (Zell et al., 2009). Using site directed mutagenesis, ODC1 +263 was changed from G to T and re-cloned in the pGL3-Basic vector (Promega, Madison, Wis.). ODCJ reporter constructs contained 1.6 kb of ODC1, including all E-box elements. For c-MYC and Sp1 overexpression experiments, ODC1 pGL3-Basic plasmids were co-transfected with either pcDNA 3.0 (vector control) or pcDNA3-c-MYC expression vector (Ricci et al., 2004) (Addgene plasmid 16011) and pN3-empty vector control (Addgene plasmid 24544) or full-length Sp1FL (Addgene plasmid 24543) (Sapetschnig et al., 2004).

Transfection Experiments.

HCT116 cells were transfected in 24-well plates. Cells were seeded at $0.1 \times 10^6$ cells/well 24 h prior transfection. Each well was transfected with 0.25 μg of each plasmid and 0.025 μg of Renilla-TK plasmid using 2.5 μL Lipofectamine 2000 reagent (Invitrogen) according to the manufacturer's instructions. The Renilla-TK plasmid was purchased from Promega and used as a transfection efficiency control in all promoter-reporter transfection experiments. For the overexpression experiments, ODC1 pGL3-Basic or Enhancer plasmids were co-transfected with the corresponding plasmid: pcDNA 3.0 empty vector, pcDNA3-c-MYC expression vector (Ricci et al., 2004) (Addgene plasmid 16011), full-length pN3-Sp1FL (Sapetschnig et al., 2004) (Addgene plasmid 24543), pN3-empty control (Addgene plasmid 24544), N-terminal mutate pPac-Sp1 (Courey and Tjian, 1988) (Addgene plasmid 12095) and pPac0 empty vector (Courey and Tjian, 1988) (Addgene plasmid 12094). After 5 h of transfection, the medium was replaced with fresh normal medium in the absence of antibiotics. After 24 h, cells were lysed in Passive Lysis Buffer from the Dual Luciferase Assay kit (Promega). Dual luciferase activities were measured using a Turner Designs TD-20/20 luminometer, as described by the manufacturer, and presented as relative luciferase units. Experiments were performed in triplicate, repeated at least twice, and analyzed for statistical significance ($P<0.05$) using two-sample t-tests (Microsoft Excel).

Knock-Down Experiments.

Silencer selected siRNA was used to knock-down Sp1 protein (Life Technology Catalog Number 4392420) along with siRNA scramble negative control #1 (Life Technology Catalog Number 4390843) following the manufacturer's instructions.

Genotyping.

SNPs genotyping was performed using sequenom MassARRAY iPLEX as previously described (Gabriel et al., 2009). ODC1 +263 SNP genotyping was performed by EpigenDx using pyrosequencing. Haplotypes were constructed using PHASE software (Stephens et al., 2001; Stephens et al., 2003) and Haploview (Barrett, 2009; Barrett et al., 2005) using the default algorithm based on the confidence bound on D' (Gabriel et al., 2002).

Polyamine Measurements.

Cells were homogenized in 0.2 N $HClO_4$. Acid-soluble and acid-insoluble fractions were used to determine intracellular polyamines and protein content, respectively. The acid-soluble fraction containing polyamines were separated using reverse-phase ion pair HPLC as described previously (Simoneau et al., 2008). Polyamine values are expressed as nmol/mg protein.

Western Blot Analysis.

Ninety percent confluent cells in culture were harvested, lysed in RIPA buffer, and proteins were separated on a 12.5% SDS-PAGE gel. Proteins were electro-transferred into a Hybond-C membrane. The membrane was blocked with Blotto A (5% blocking grade dry milk in PBS-tween buffered saline solution) and probed using 1:500 dilutions of primary antibodies (Santa Cruz Biotechnology) in Blotto A. Primary antibodies were incubated at 4° C. overnight or two hours at room temperature, followed by incubation with an appropriate horseradish peroxidase-tagged secondary antibody (1:2,000 dilution) for one hour at room temperature. Chemiluminescent detection was conducted using ECL Western Detection reagent (Amersham Biosciences) and exposed on Biomax XAR film (Kodak).

Chromatin Inmunoprecipitation (ChIP) and Co-Inmuno-precipitation (Co-IP) Assays.

ChIP and co-IP assays were performed using the ChIP Assay Kit protocol (Millipore, catalog #17-295) as recommended by the manufacturer. Briefly, cells were treated with 1% formaldehyde to cross-link DNA and proteins, and DNA-protein complexes were disrupted by sonication to lengths between 200 and 1,000 bp. Lysates were diluted 10-fold with immunoprecipitation dilution buffer containing protease inhibitors. Antibodies for Sp1, c-MYC and control IgG (Santa Cruz Biotechnology) were used to precipitate chromatin, and an additional sample was left as a normal IgG control. Samples were immunoprecipitated overnight at 4° C. with rotation Immune complexes were obtained by adding 60 μL of salmon sperm DNA/protein A agarose slurry and incubating for 1 h at 4° C. with rotation followed by gentle centrifugation (1,000 rpm for 1 min). Protein A agarose pellets were washed with low-salt buffer, high-salt buffer, LiCl buffer, and TE buffer. Next, the complex samples were divided for co-IP or ChIP analysis. For co-IP analysis, 25 μL of 2× Laemmli buffer was added and boiled for 10 minutes. Then, 20 μL samples were loaded onto a 12.5% SDS-page gel for Western blotting, including the diluted input samples (1:10) and controls. For the ChIP analysis, samples were eluted by adding 250 μL elution buffer (0.1 M $NaHCO_3$, 1% SDS) twice, and DNA-protein cross-links were reversed with 0.2 M NaCl by heating at 65° C. for 4 h for all samples, including the input DNA and controls. DNA was resuspended in 30 μL of dd$H_2O$. For visualization of PCR products and their size, standard PCR reactions were conducted. The sequences of ODC1 primers used for PCR were 5'-CCTGGGCGCTCTGAGGT-3' (SEQ ID NO: 4) and 5'-AGGAAGCGGCGCCTCAA-3' (SEQ ID NO: 5).

Example 1—Functional Consequence of Genetic Variability in a G-Quadruplex Structure in the Ornithine Decarboxylase (ODC1) Gene The ODC1 promoter region contains multiple sequences that allow for transcriptional control in response to hormones, growth factors, and tumor promoters, such as enhancer (E)-boxes, cAMP response elements, CAAT and LSF motifs, AP-1 and AP-2 sites, GC-rich Sp1/Sp3 binding sites, WT1, and a TATA box (Pegg, 2006). ODC1 has three MYC-binding elements (E-boxes) in the region from −400 to +400 bp relative to the transcription start site (TSS). Polyamine-induced nuclear c-MYC interacts with MAX, and this complex binds to E-box sequence (CACGTG) to activate transcription of target genes, such as ODC1, thus accelerating polyamine biosynthesis (Kumar et al., 2009). The transcriptional repressor MAD1/MAX also binds to these elements to regulate the transcription level of ODC1 in proliferative cells (Pegg, 2006; Nilsson et al., 2004).

Although polyamine metabolism is a validated pathway for prevention of colorectal cancer and skin epithelial carcinogenesis (Meyskens et al., 2008; Bailey et al., 2010), with on-going clinical trials in neuroblastoma and FAP, the mechanisms by which polyamines elicit their tumorigenic effects are poorly understood (Paz et al., 2014). A single nucleotide polymorphism, rs2302615, in the human ODC gene with a G/A variation located 316 nucleotides downstream of the transcription start site (TSS) is flanked by two consensus E-boxes in the promoter/intron 1 region, only five nucleotides upstream from the third E-box (Guo et al., 2000; Zell et al., 2009; Martinez et al., 2003). A clinical association has been established between SNP+316 with the risk of colorectal adenoma (CRA) recurrence by different studies, especially in aspirin users (Pegg, 2006; Kumar et al., 2009; Nilsson et al., 2004; Meyskens et al., 2008), and with sporadic colorectal cancer (CRC) (Zell et al., 2009).

The ODC1 +263 SNP, which is 53 nucleotides upstream of the ODC1 +316 SNP, has a T/G transversion that computationally disrupts an Sp1 binding site and is located in a potential G-quadruplex (G4) forming sequence. Nucleic acid sequences rich in guanine can form a DNA secondary structure called G4 from four or more runs of three or more contiguous guanines. It has been proposed that G4 may be directly involved in gene regulation at the level of transcription. The promoter regions and first introns (−500 to +500 bases from TSS) of genes are significantly enriched in G4 motifs relative to the rest of the genome (Huppert and Balasubramanian, 2005; Eddy and Maizels, 2008). ODC1 intron 1 contains nine runs of three contiguous guanines separated by one or more bases making it a putative G4 forming sequence (Lam et al., 2013). The planar core of a G4 is a series of G-quartets, most commonly three, each of which consists of four guanine bases, arranged with a four-fold rotational symmetry such that they can form two hydrogen bonds along each edge. These structures then stack on each other in a helical fashion, forming a G4 structure with vast diversity in their folding patterns (uni-, bi- or tetra-molecular), loop lengths and directionality (parallel, antiparallel or mixed) (Huppert, 2008; Brooks, 1988), making them putatively amenable to specific drug targeting (Brooks et al., 2010; Balasubramanian et al., 2011). G4 regulates transcription of genes involved in cancer (Hanahan and Weinberg, 2011; Hanahan and Weinberg, 2000), such as c-Myc, c-Kit, and KRAS (self-sufficiency); p53 (insensitivity); Bcl-2 (evasion of apoptosis); VEGF-A (angiogenesis); hTERT (limitless replication); and PDGF-A (metastasis) (Brooks et al., 2010; Balasubramanian et al., 2011). The proposed function of these secondary structures is to alter gene transcription, either repressing it by polymerase stalling or blocking (by recruitment of repressors) or facilitating or stimulating transcription (Bochman et al., 2012). Recently, G4 formation has been addressed genome-wide in vivo to verify their existence in the genome (Lam et al., 2013). Genome-wide analysis revealed a regulatory role of G4 DNA in gene transcription and that single nucleotide polymorphisms (SNPs) located in the G4 forming sequence influence gene expression among individuals (Du et al., 2008; Baral et al., 2012). G4 forming promoters/introns harbor low numbers of polymorphic site and they are evolutionary devoid in the G4 core portion, which have the highest impact in the disruption of the G4 structure (Baral et al., 2012). Small molecules can stabilize G4 structures, viewed as transcriptional repression of oncogenes, which are emerging therapeutic targets in oncology and could be a novel anticancer strategy to reduce the expression of oncogenes (Balasubramanian et al., 2011), such us c-MYC (Qin and Hurley, 2008). c-MYC oncogene, which activates the transcription of ODC1, has been proposed as a comprehensive strategy to combat colorectal cancer (Gerner et al., 2005).

The Specificity Protein/Krüppel-like Factor (Sp/KLF) family of transcription factors (Sp1, Sp2, Sp3, and Sp4) is united by a particular combination of three conserved $Cys_2His_2$ zinc fingers, which form the DNA-binding domain of these factors (Li et al., 2004). Sp1 and Sp3 are ubiquitously expressed in mammalian cells and share more than 90% sequence homology in the DNA-binding domain, while Sp2 and Sp4 have restricted expression patterns (Davie et al., 2008). Sp1 and Sp3 bind to the same cognate DNA-element (GGGGCGGGG), but they have strikingly different functions especially in later developmental stages, but their function is redundant in early development (Li et al., 2004). Sp1 is an important transcription factor that binds to G4 forming elements (Todd and Neidle, 2008; Raiber et al., 2012), suggesting a possible mechanism of gene regulation. Both Sp1 and Sp3 can recruit and interact with a large number of proteins, including the transcription initiation complex, histone modifying enzymes and chromatin remodeling complexes, which strongly suggest that Sp1 and Sp3 are important transcription factors in remodeling chromatin and regulating gene expression (Davie et al., 2008).

A comprehensive investigation to understand the significance of other SNPs in ODC1 in colorectal carcinogenesis was conducted (Barry et al., 2011), to understand the molecular mechanisms that explain the chemoprevention clinical association. The polymorphisms at the ODC1 +263 and +316 SNPs might be related due to their close proximity. The frequencies of 49 SNPs in 196 patients participating in the DFMO/sulindac cancer prevention trial were confirmed (Meyskens et al., 2008), and 11 SNPs with minor allele frequencies around 10% and limited common haplotypes accounting for more than 90% of participants were identified. The ODC1 +263 SNP divided observed frequencies in two major groups of participants in the clinical trial. In addition, the ODC1 +263 SNP predicted statistically significant ODC rate-limiting product putrescine levels by genotype at baseline in normal tissues of participants in the DFMO/sulindac trials. Thus, the ODC1 +263 SNP may be involved in a novel molecular mechanism of gene transcriptional regulation that explains ODC1-related clinical outcome and the prediction of putrescine levels by ODC1 +263 genotype. Here, the role of the ODC1 +263 SNP in G4 formation and its stability, as well as how Sp1 transcription factor plays a role in the transcriptional regulation of ODC1, were examined.

ODC1 intron 1 forms a G-quadruplex secondary structure. To explain the potential mechanism for the transcriptional differences in ODC1 expression dependent on the +263 allele, higher order DNA structures were considered. Computational studies predicted that the ODC1 +263 SNP is located within a G4 forming sequence and also disrupts an Sp1 transcription factor binding site, using Quadparser (Huppert and Balasubramanian, 2005) and PROMO software (Messeguer et al., 2002; Farre et al., 2003), respectively. In order to examine potential effects on both putative G-quadruplex formation and Sp1 binding, oligonucleotides of the region of interest were studied (Table 1).

Figure 2A:
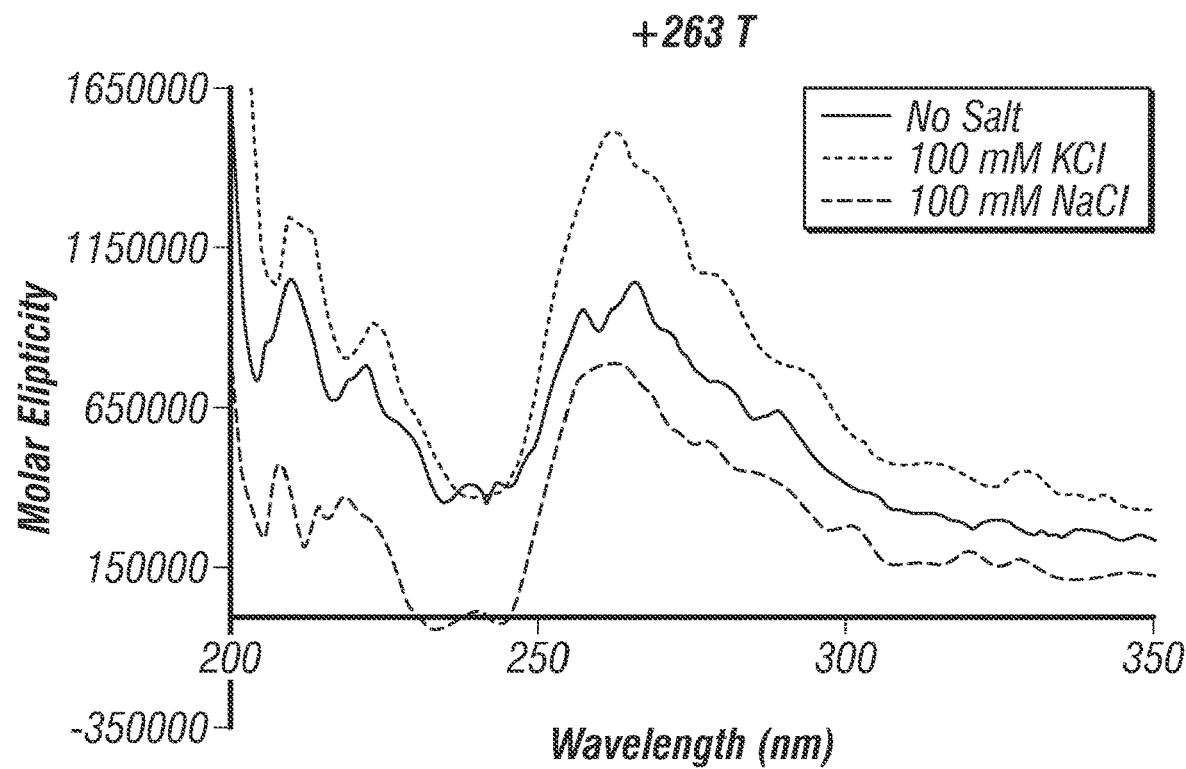
FIGS. 2A-B. CD spectra demonstrating G-quadruplex formation with ODC1 oligonucleotides. ODC1 SNP+263 T (A) and G (B) oligonucleotides (5 μM; SEQ ID NOs: 2 and 1, respectively) were heated to 95° C. and slowly cooled to room temperature in the absence (solid line) or presence of 100 mM KCl (short dash) or NaCl (long dash). All spectra were read at 25° C. from 200-350 nm. A positive CD peak at 260-265 nm indicates the presence of a parallel G-quadruplex.
Figure 2B:
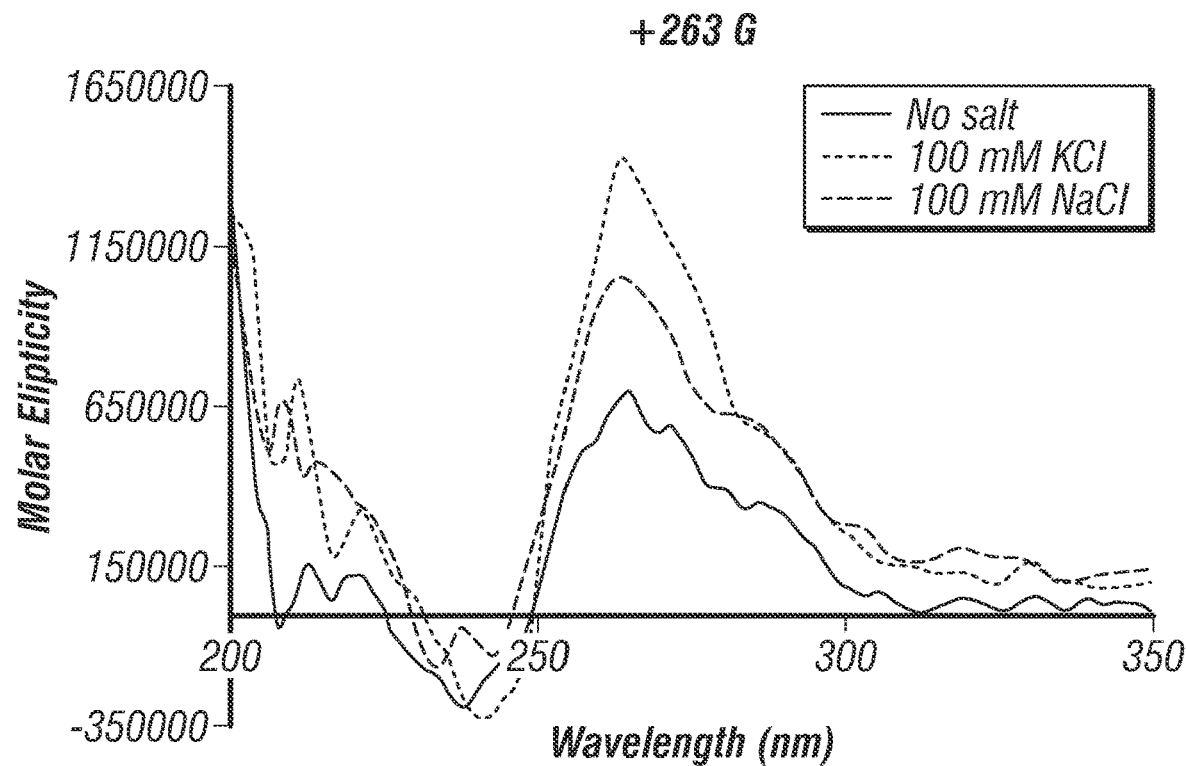

G-quadruplex formation can be determined using circular dichroism (CD) to measure spectra and thermal stability (Huppert, 2008; Kypr et al., 2009). Within the ODC1 intron, 58 nucleotides that encompass the G-rich region putatively capable of forming a non-B-DNA structure, which consisted of nine runs of guanines around the ODC1 +263 SNP (within the sixth run), were studied (Table 1). The oligomers with either the G or T allele at the SNP position of interest were able to form G-quadruplex structures, even in the absence of any monovalent cation, as seen by a positive spectral peaks around 260-265 nm, indicative of a parallel loop, and around 290-295 nm, indicative of an antiparallel loop (FIGS. 2A-B, black line). G-quadruplexes are stabilized by monovalent cations at the center of the tetrads, in particular potassium and sodium for inter- and intra-molecular structure, respectively (Sen and Gilbert, 1990). With the ODC1 +263 T sequence, ME was altered upon the addition of NaCl or KCl with a downward and an upward shift, respectively; however, the peak patterns were not changed (FIG. 2A). Overall thermal stability of this sequence was lower than the ODC1 +263 G, with a $T_M$ of 49° C., which was nominally changed by the addition of either NaCl (−2° C. $\Delta T_M$) or KCl (+1° C. $\Delta T_M$) (Table 2). The addition of 100 mM KCl or NaCl increased the molar ellipticity (ME) of the ODC1 +263 G oligonucleotide (FIG. 2B). In particular, NaCl more clearly delineated the parallel from the antiparallel peaks with a moderate increase in ME, while KCl more robustly increased ME and notably increased the amplitude of the parallel over the antiparallel peak. The addition of each of these cations corresponded with a change in thermal stability as well. In the absence of any cations, the $T_M$ of the ODC1 +263 G oligo was 61° C. The addition of NaCl induced a −11° C. $\Delta T_M$, while KCl led to a +4° C. $\Delta T_M$ (Table 2). Thus, both ODC1 +263 sequences demonstrated the signature peak characteristic of G-quadruplex formation, with above physiological thermal stability even in the absence of any monovalent cations. The addition of monovalent cations had a more notable effect on G-quadruplex formation and stability with the G vs. T+263 allele.

TABLE 2

Thermal stability of ODC1 +263 G or T oligonucleotide (5 μM) in salt-free conditions, or in presence of KCl (100 mM) or NaCl (100 mM).

| $T_M$ (° C.) | No salt control | KCl (100 mM) | NaCl (100 mM) |
| --- | --- | --- | --- |
| +263 T | 49.24 | 49.74 | 47.11 |
| +263 G | 60.65 | 64.26 | 50.15 |

ODC1 +263 SNP Influences G-Quadruplex Stability.

Figure 4:
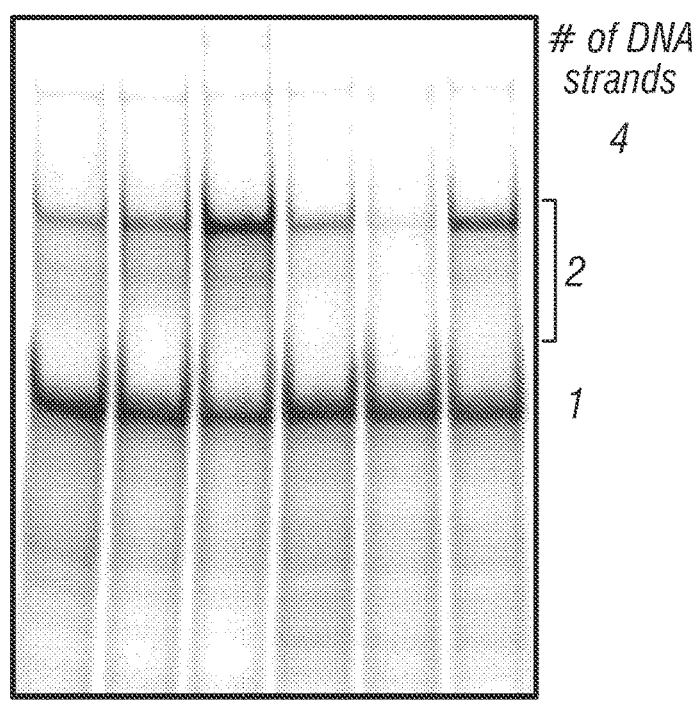
FIG. 4. Differential stabilization and migratory patterns of inter- and intra-molecular G-quadruplex forms in the ODC1 SNP+263 G and T oligonucleotides. EMSA experiments were performed with ODC1 SNP+263 G and T oligonucleotides in the absence (−) or presence (+) of 100 mM KCl or NaCl. The G oligonucleotide produced more intra-unimolecular G-quadruplex than the T oligonucleotide. KCl and NaCl treatment stabilized intra-molecular and inter-molecular G-quadruplex, respectively, in the G oligonucleotide, but no clear effect was evident with the T oligonucleotide.
Figure 6A:
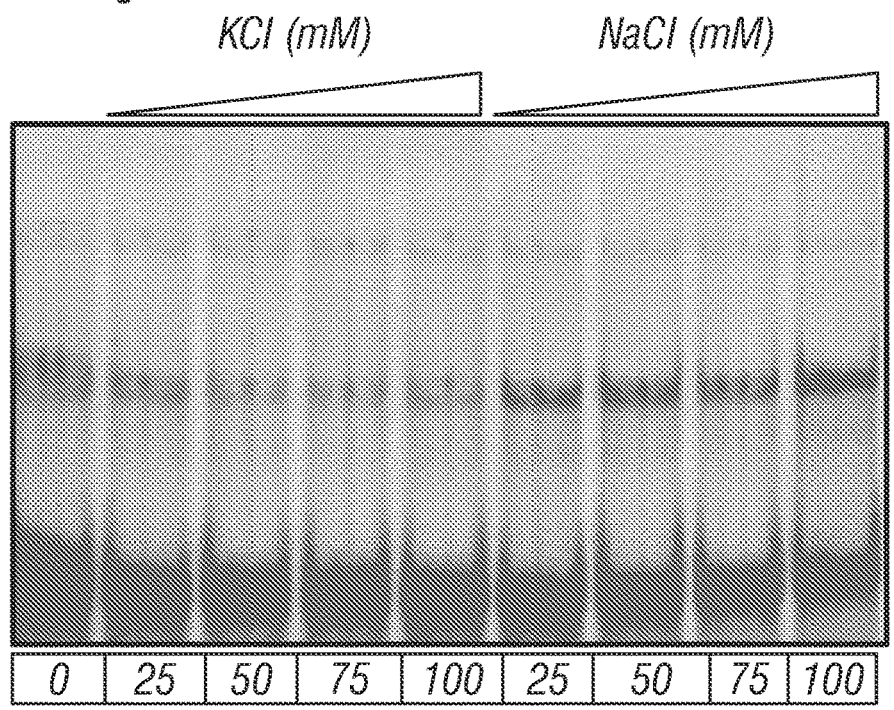
FIGS. 6A-B. Differential stabilization of inter- and intra-molecular G-quadruplexes in the ODC1 sequences. Intermolecular and intramolecular G-quadruplexes formed in the G oligonucleotide (A) and T oligonucleotide (B) sequences. Oligonucleotides were incubated in the absence (0) or presence of increasing concentrations of KCl or NaCl (25, 50, 75, 100 mM). NaCl, in both sequences, demonstrated enhanced stabilization of intermolecular structures, whereas KCl decreased their formation.
Figure 6B:
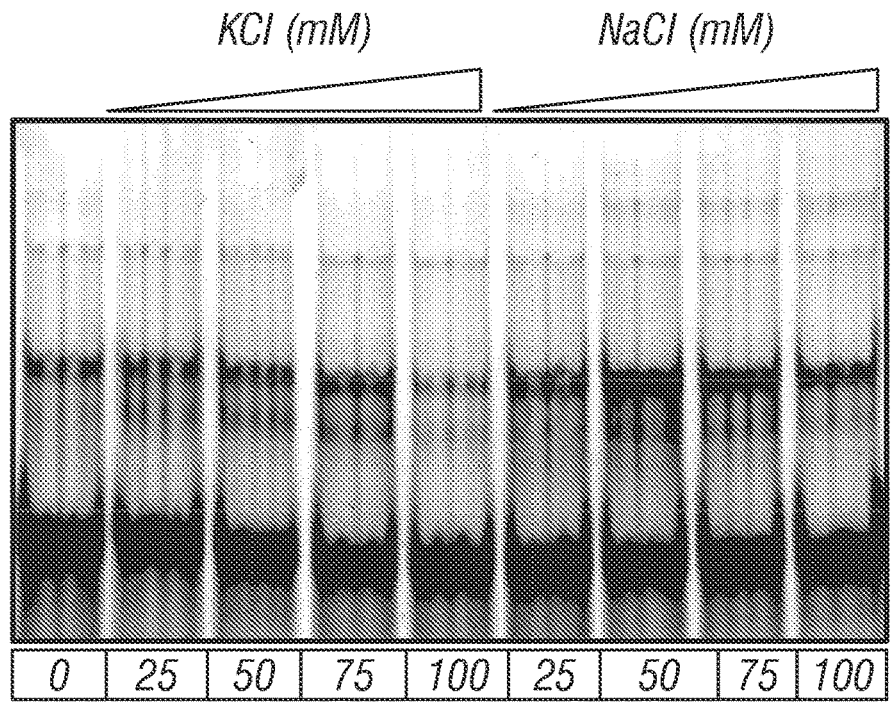

Single-stranded G-rich sequences have the potential to adopt multiple conformations, including forming from four separate DNA strands (inter-tetramolecular), two separate DNA strands (inter-bimolecular), or a single DNA strand (intra-unimolecular). The intra-unimolecular G4 is the biologically relevant composition or isoform. To determine whether the G4 formed by the ODC1 intron 1 are intra or intermolecular, the electrophoretic mobilities and thermal stabilities of different sequences in the absence and presence of KCl or NaCl were analyzed using electrophoretic mobility assay (EMSA). With either the +263 G or T oligonucleotide, even in the absence of a monovalent cation, and consistent with the CD data, there is evidence of both inter- and intra-molecular G-quadruplex formations (FIGS. 4 and 6A-B). Particularly, with the T allele only 2% of the species exist in linear form, while 81% are in intramolecular structures, and 17% and 1% are in di- and tetra-intermolecular formations, respectively. Similarly for the G allele, the linear formations are only 1%, while the intramolecular formations are 81% and the di- and tetra-intermolecular structures are 19% and 1%, respectively.

For the T allele, KCl and NaCl function to alter the distribution of intramolecular formations (both decreasing the frequency to 69% and 47%, respectively), while not altering the tetramolecular or linear distributions, but rather selectively increasing the inter-bimolecular species to 25% and 48%, respectively. For the G allele, the addition of NaCl yields similar results, primarily an increase in the inter-dimolecular species to 36% and a decrease in the intramolecular formations to 61%. There are much more marked changes with KCl where the inter-dimolecular formation decreases to 6% (a ~70% decrease); concomitantly, the intramolecular formations increase to 94% of the total band population. These data are in agreement with the above CD data, and with the tendency of KCl to support intramolecular structures, and for NaCl to facilitate intermolecular formations. Moreover, the CD and the differential equilibrium stabilization obtained by EMSA confirm a higher stability of the G-quadruplex structure with ODC1 +263 G-allele than the T-allele, and a higher propensity to form the more biologically relevant intermolecular species.

Stabilization of G-Quadruplex Formation with a Pan-Binding Compound, NSC176327.

Figure 5:
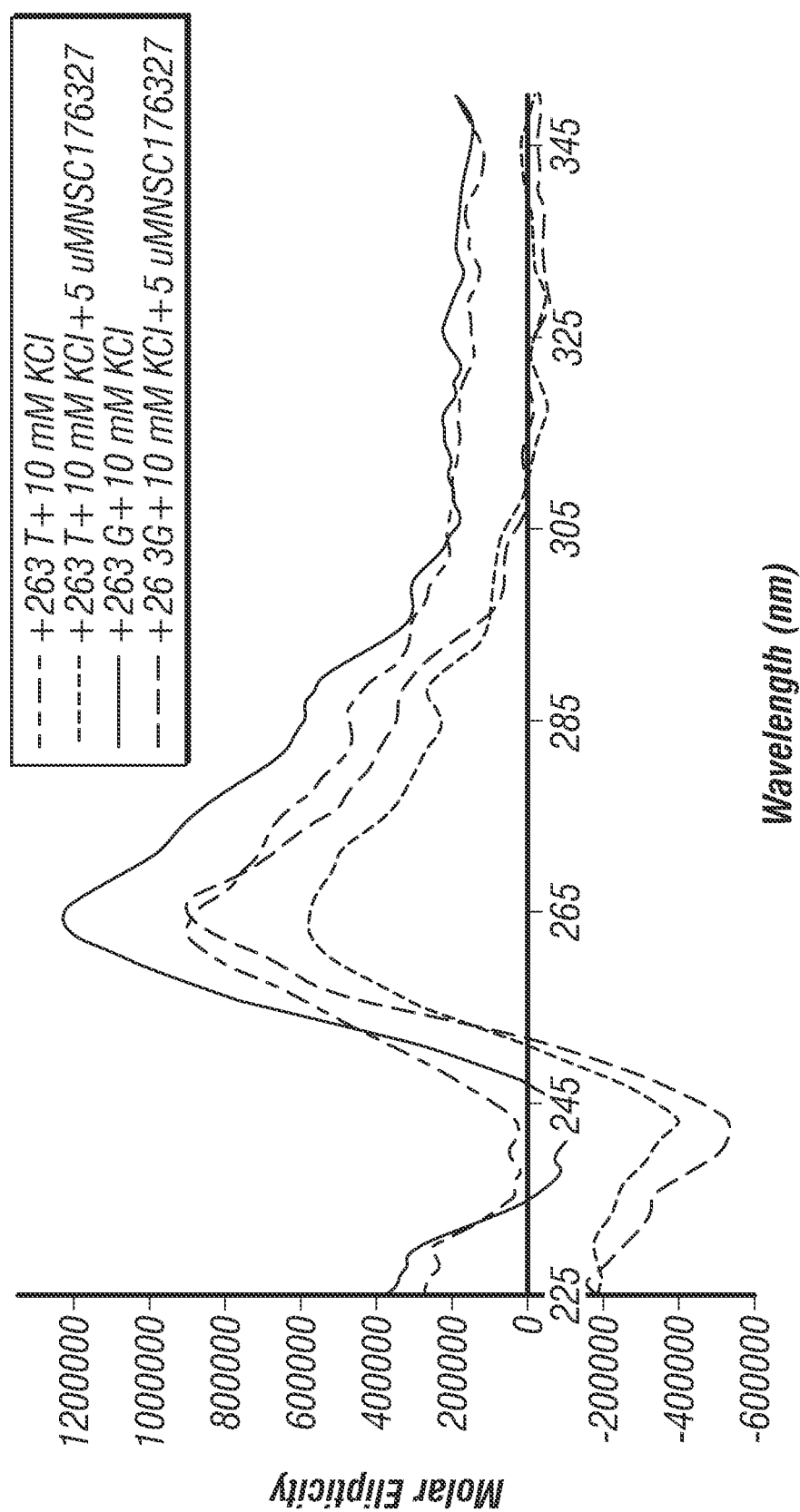
FIG. 5. CD Spectra demonstrating G-quadruplex formation with +263 T and G allele in presence and absence of NSC176327 in 10 mM KCl. ODC1 +263 T and G oligonucleotides (5 μm) were heated to 95° C. and slowly cooled to room temperature in the absence (black line) or presence of 10 mM KCl and in the presence or absence of NSC176327. All spectra were read at 25° C. from 200-350 nm. A positive CD peak at 260-265 nm indicates the presence of a parallel G-quadruplex, and one at 290 nm indicates an antiparallel G-quadruplex, differing in the 5'-3' directionality of the strands.

In order to strongly enhance any higher order DNA structures formed, NSC176327, a compound with pan-G-quadruplex stabilizing activity, was used to perform CD spectra and thermal stability experiments. Each of these experiments was done in the presence of 10 mM KCl to allow for equilibrating G-quadruplex formation. Well-defined CD spectra indicative of G-quadruplex peaks were observed in the absence and in the presence of 5 μM NSC176327 (FIG. 5). Although molar ellipticity of both the +263 T and G allele G-quadruplex peaks decreased by ~⅓ in the presence of 10 mM KCl and the compound, thermal stabilities increased to 75 and 68° C., which translate to nominal $\Delta T_M$ increases over the DMSO-matched experiment at +14 and +11° C., respectively (Table 3).

Figure 10:
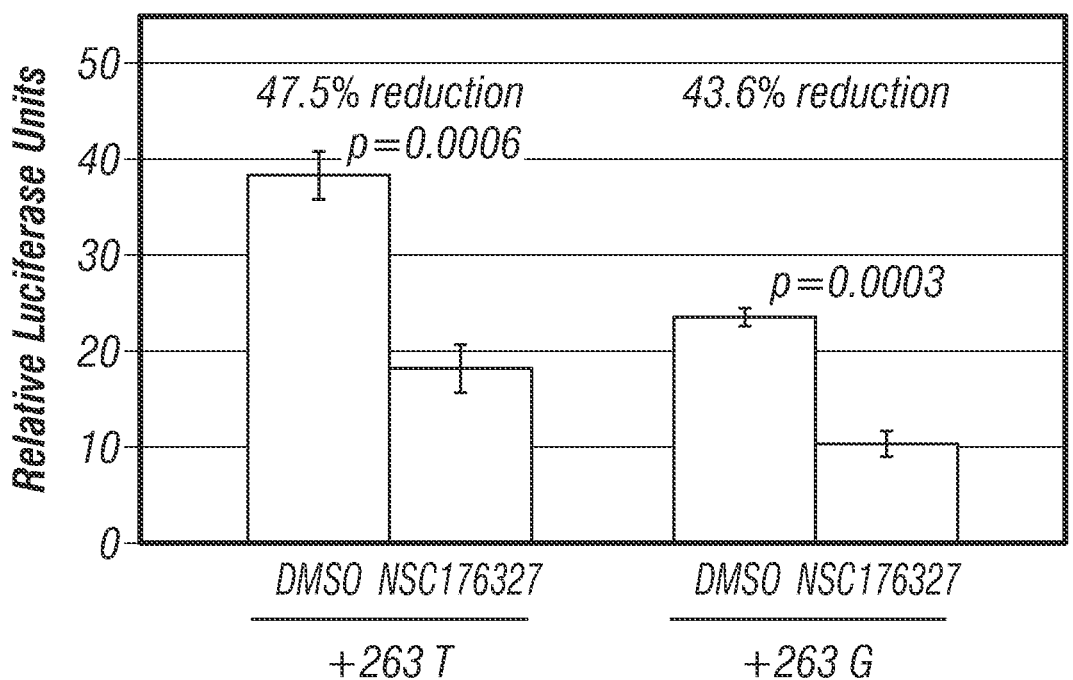
FIG. 10. Transfection experiments with the isogenic ODC1 +263 SNP plasmid in the presence of NSC176327. HCT116 cells were transfected with the 1.6 kb ODC1 promoter/intron 1 construct in the pGL3-Basic plasmid. Luciferase promoter activity was measured at 24 h with the respective time-matched DMSO control. A statistically significant reduction of luciferase activity was observed with the NSC176327 G-quadruplex stabilizing drug with either G or T at ODC1 +263. *Renilla* luciferase was used to normalize for differences in transfection efficiency.

The effect of NSC176327, and presumed stabilization of the G-quadruplex within the ODC1 gene, was then examined in vivo using the +263 T and G plasmids. HCT116 colorectal cancer cells were transfected with the ODC1 +263 SNP plasmids, and allowed to grow in presence of 2 µM NSC176327, which is the 24 h $IC_{50}$. Stabilization of the G-quadruplex structure with NSC176327 led to a statistically significant (P<0.01) decrease the ODC1-luciferase reporter expression at 24 h (FIG. 10). The effect of NSC176327 normalized to time-matched DMSO is 47.5% and 43.6% reduction for ODC1 +263 T and G, respectively. The same degree of stabilization are in agreement with the ex vivo findings. It is important to mention that the use of NSC176327 is associated with reduction of firefly and renilla luciferase reading, with no change in cell viability, but an apparent change in morphology was observed.

TABLE 3

Thermal stability ($T_M$) of ODC1 +263 T and G oligonucleotides (5 µm) were measured in the presence of 10 mM KCl and in presence and absence of NSC176327.

|  | +263 T 10 mM KCl | | +263 G 10 mM KCl | |
| --- | --- | --- | --- | --- |
|  | DMSO | 5 uM NSC176327 | DMSO | 5 uM NSC176327 |
| $T_M$ (° C.) | 60.52 | 74.69 | 57.21 | 68.45 |
| $\Delta T_M$ (° C.) |  | +14.17 |  | +11.24 |

The stability of the parallel G-quadruplex peak at 262-264 nm was measured, at a heating rate of 2° C./min (4° C. to 90° C.), with a response time of 1 s. All sequence demonstrated NSC176327 drug stabilization in relationship with their matched not drug treated condition.

ODC1 G-Quadruplex Structure is Formed in Double Stranded DNA (dsDNA) and Sp1 Transcription Factor Shifted the G-Quadruplex Structure to Classical B-Form DNA in an ODC1 +263 SNP Independent Fashion.

Figure 7A:
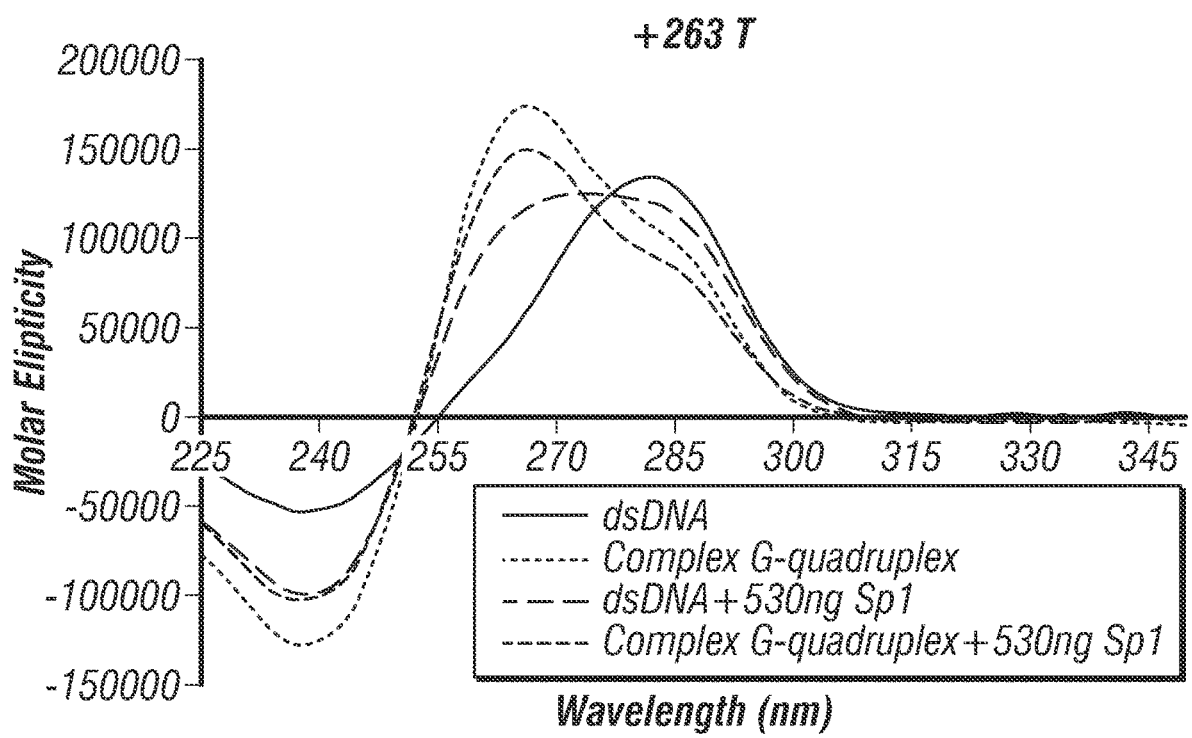
FIGS. 7A-B. CD spectra of different double-stranded DNA sequences in Tris-Acetate buffer (50 mM, pH 7.6) with 100 mM KCl were obtained between 200-350 nm. A positive CD peak at 260-265 nm indicates the presence of G-quadruplex and classical DNA B-form is represented by a peak at 280-285 nm. Double-stranded T (A) and G (B) are able to form a classical DNA B-form and switch to the G-quadruplex conformation in the presence of KCl with or without Sp1 protein. Each spectrum corresponds to three averaged scans taken at 25° C. and is baseline corrected for signal contributions due to the buffer and salts.
Figure 7B:
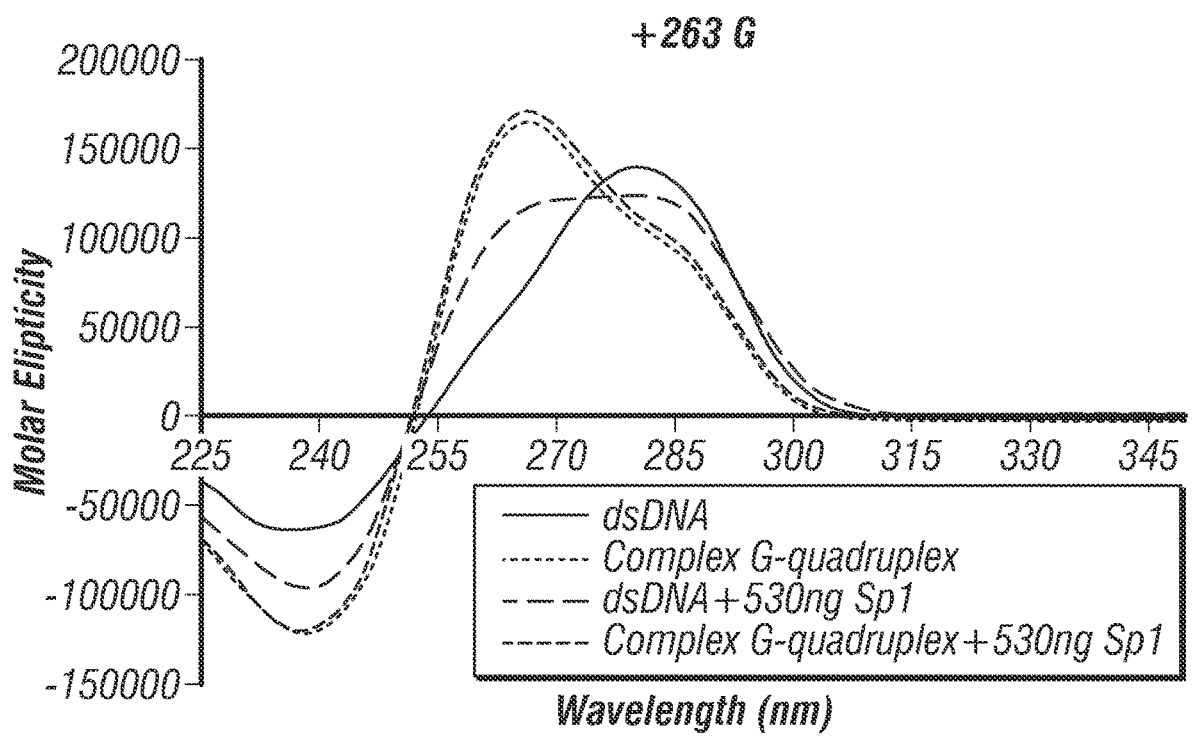
Figure 8A:
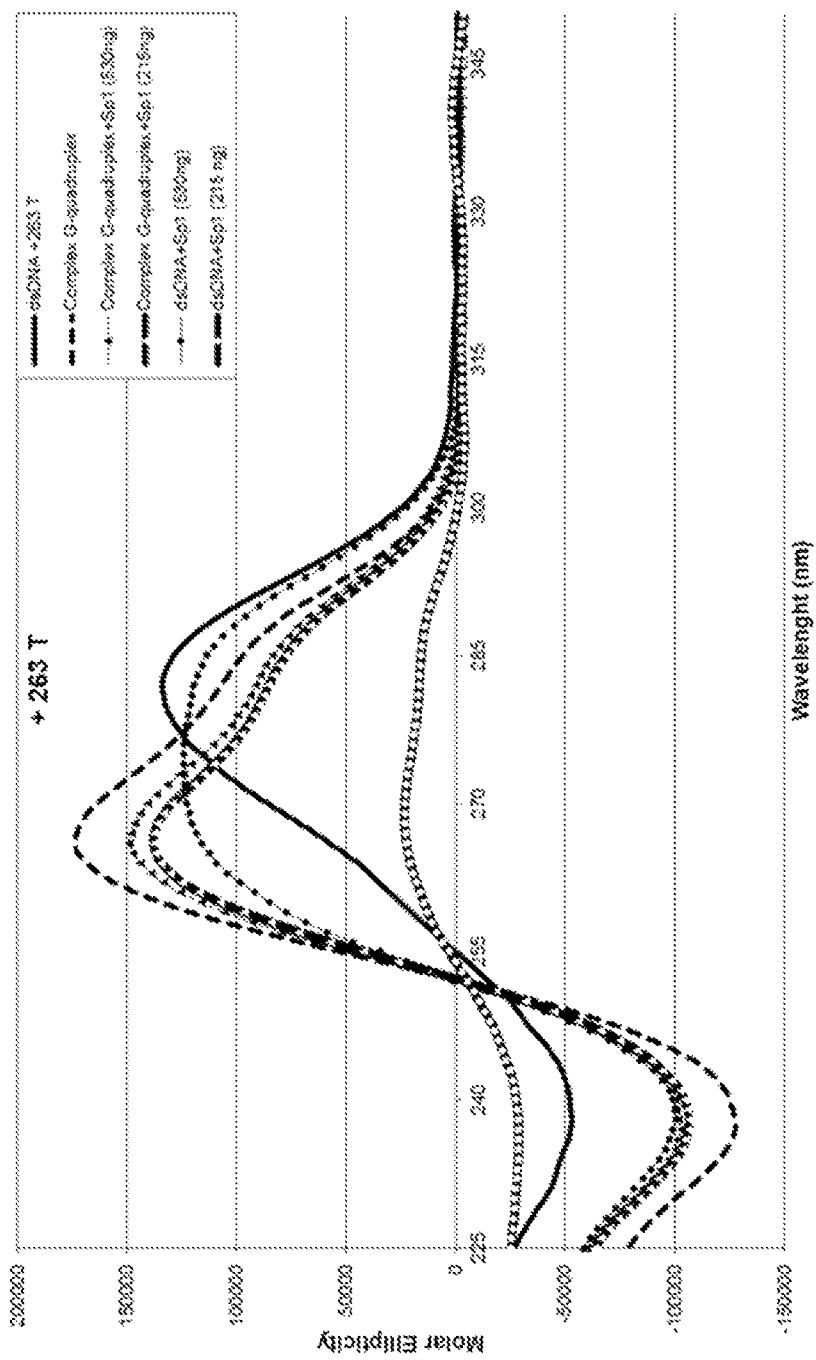
FIGS. 8A-B. CD spectra of different double-stranded DNA sequences in Tris-Acetate buffer (50 mM, pH 7.6) with 100 mM KCl were obtained between 200-350 nm. A positive CD peak at 260-265 nm indicates the presence of G-quadruplex and the classical DNA B-form was represented by a peak at 280-285 nm. Double-stranded T (A) and G (B) were able to form a classical DNA B-form and switch to the G-quadruplex conformation in the presence of KCl with or without Sp1 protein. Each spectrum corresponds to three averaged scans taken at 25° C. and is baseline corrected for signal contributions due to the buffer and salts.
Figure 8B:
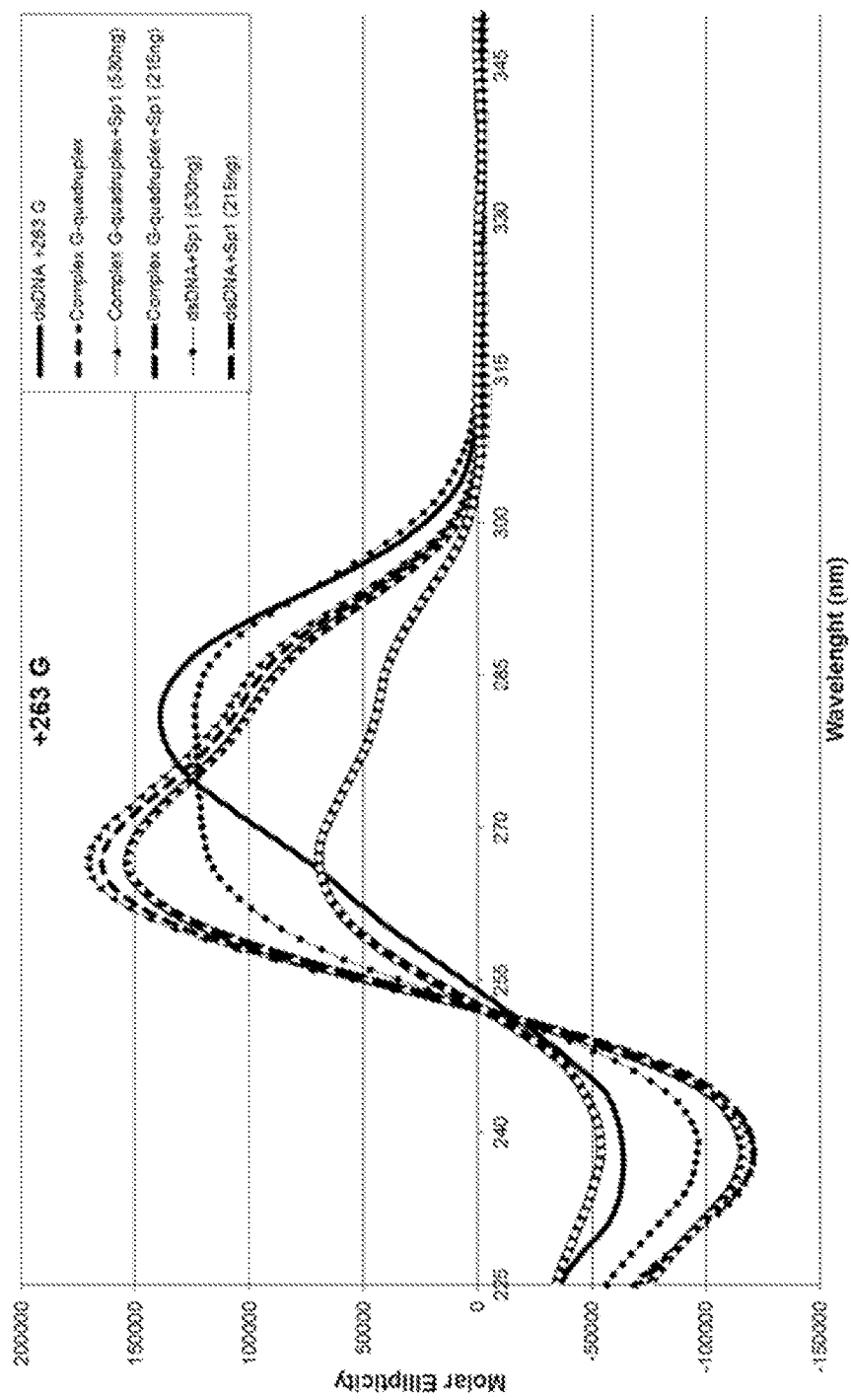
Figure 9:
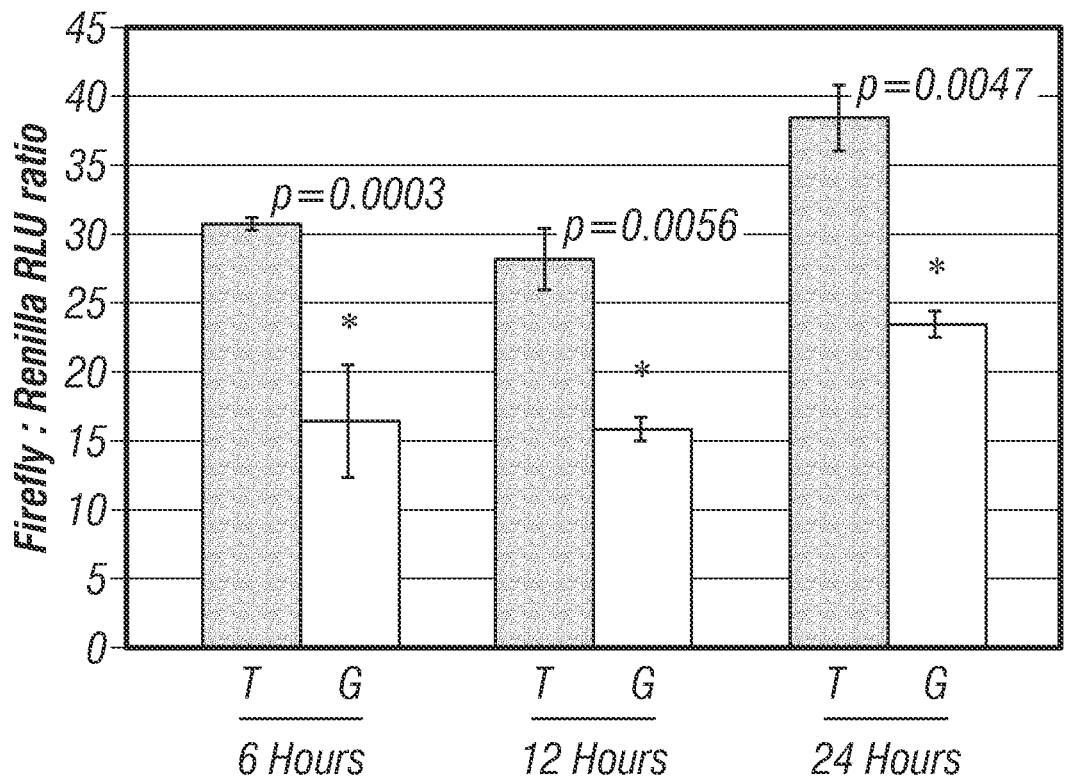
FIG. 9. Transfection experiments with the isogenic ODC1 +263 SNP plasmid. HCT116 cells were transfected with the 1.6 kb ODC1 promoter/intron 1 construct in the pGL3-Basic plasmid. Luciferase promoter activity was measured at 6, 12, and 24 h. A higher luciferase promoter activity was associated with the ODC1 +263 T-allele at all time points, in comparison with the ODC1 +263 G-allele. *Renilla* luciferase was used to normalize for differences in transfection efficiency. *P<0.01.

The potential mechanisms of transcriptional changes may be due to G-quadruplex formation involving the binding of Sp1 transcription factor. The effect of Sp1 protein on G-quadruplex formation was examined with the T and G allele at ODC1 +263 in double-stranded DNA (dsDNA) and complex G-quadruplex conditions, induced with 100 mM KCl. Both dsDNA sequences formed a classical B-form DNA CD spectrum with a positive molar ellipticity peak at 280 nm and a negative peak at about 250 nm (FIGS. 7A-B, solid line). In presence of 100 mM KCl (complex G-quadruplex), the unique classical dsDNA peak was shifted to a 260-265 nm peak, consistent with the formation of a G-quadruplex structure, as was observed in the CD single-stranded DNA (ssDNA) experiment (FIGS. 7A-B, dash line). To address the role of Sp1 transcription factor in the G-quadruplex-forming sequence, 530 or 215 ng of recombinant purified human Sp1 protein was added with the ODC1 +263 T and G allele-containing dsDNA sequences in the CD experiment in the presence or absence of 100 mM KCl. The addition of Sp1 in the induced G-quadruplex maintained the characteristic peaks of the G-quadruplex at both concentrations of Sp1 (FIGS. 7A-B, open and closed triangles). In the +263 T sequence both peaks were lower that the complex G-quadruplex peaks. Instead in the +263 G sequence the higher Sp1 concentration (530 ng) stabilized the G-quadruplex peak to a greater extent than using only 100 mM KCl. The dsDNA ODC1 +263 T or G containing samples have different degrees of stabilization dependent on Sp1 concentration. When 530 ng of Sp1 protein was added, both alleles showed peaks that reflex the classical B-form of DNA and the G-quadruplex conformation (FIGS. 7A-B, close circles). In contrast, when 215 ng of Sp1 protein was added to the ODC1 +263 T allele did not show a characteristic strong peak for either the dsDNA or G-quadruplex structure. In contrast, the +263 G allele formed an induced peak towards 263 nm indicating G-quadruplex formation, even though the molar ellipticity decreased by ⅔.

To understand if G4 formation, difference in stability, and disruption of the Sp1 binding site have a functional significance in the transcriptional regulation of ODC1 in vivo, transfection experiments were performed in colorectal cell lines. Two isogenic ODC1 promoter/intron 1 luciferase plasmids were created with either G or T at ODC1 +263, with an A-allele at the ODC1 +316 SNP. Previous studies showed clinical and functional relevance of the ODC1 +316 A-allele and its association with phenotypes (Guo et al., 2000; Zell et al., 2009; Zell et al., 2010).

Figure 3:
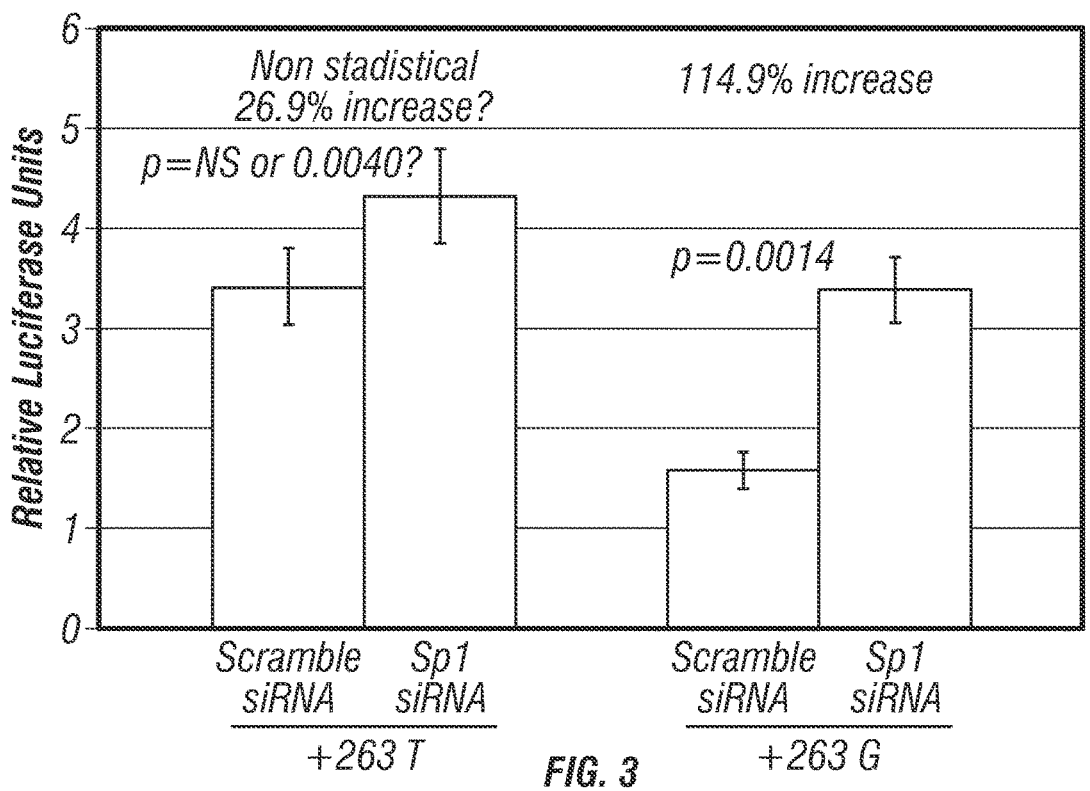
FIG. 3. Transfection experiment with isogenic ODC1 SNP+263 plasmid and genetic manipulation of Sp1 transcription factor. HCT116 cells were transfected with the 1.6 kb promoter/intron 1 ODC1 gene in the pGL3-Basic plasmid with genetically altered levels of Sp1 protein. In all conditions tested, the ODC1 +263 T-allele was associated with higher luciferase expression, as compared with the ODC1 SNP+263 G-allele. A slight reduction of luciferase was observed with the overexpression of Sp1 (pN3-Sp1) in comparison with the empty vector (pN3-Empty). In contrast, knock down of Sp1 protein expression using Sp1 siRNA resulted in a statistically significant increased in luciferase expression with both G and T ODC1 SNP+263 alleles, in comparison in the control scramble siRNA. *Renilla* luciferase was used to normalize for differences in transfection efficiency.
Figure 11:
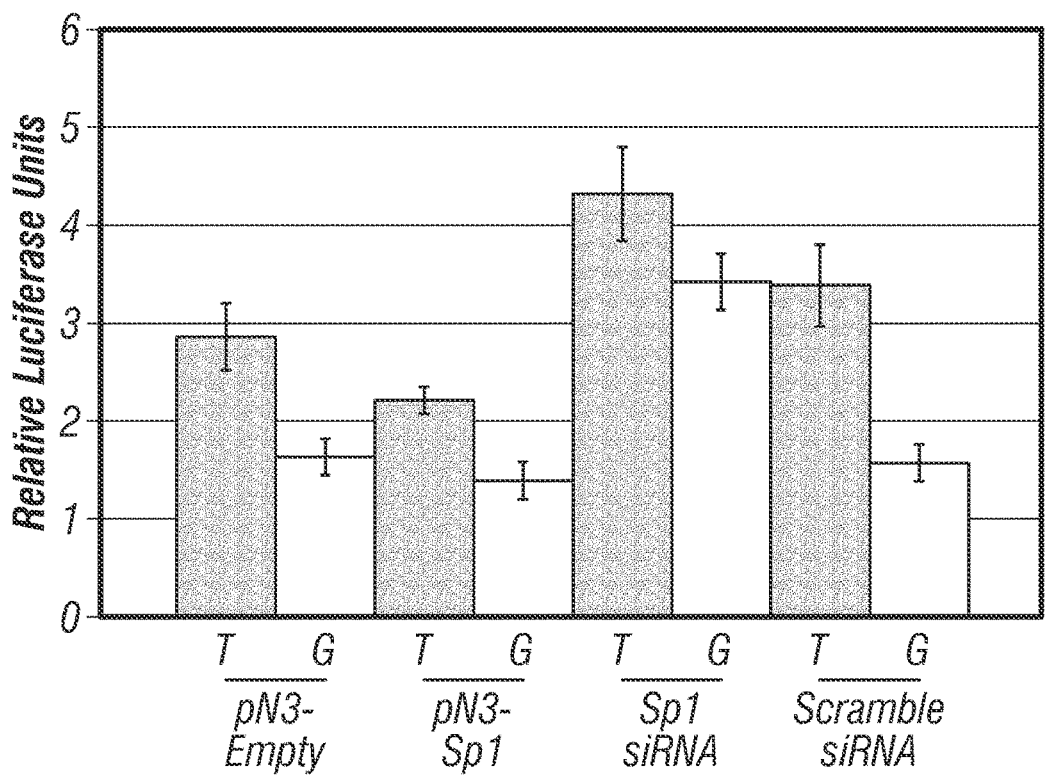
FIG. 11. Transfection experiments with the isogenic ODC1 +263 SNP plasmid and genetic manipulation of Sp1 transcription factor. HCT116 cells were transfected with the 1.6 kb ODC1 promoter/intron 1 construct in the pGL3-Basic plasmid with genetically altered levels of Sp1 protein. In all conditions tested, the ODC1 +263 T-allele was associated with more luciferase activity, as compared to the ODC1 +263 G-allele. A slight reduction of luciferase was observed with the overexpression of Sp1 (pN3-Sp1), in comparison with the empty vector (pN3-Empty). In contrast, knockdown of Sp1 protein expression using Sp1 siRNA resulted in a statistically significant increase in luciferase expression with both G and T ODC1 +263 alleles, in comparison to the control scramble siRNA. *Renilla* luciferase was used to normalize for differences in transfection efficiency.
Figure 12:
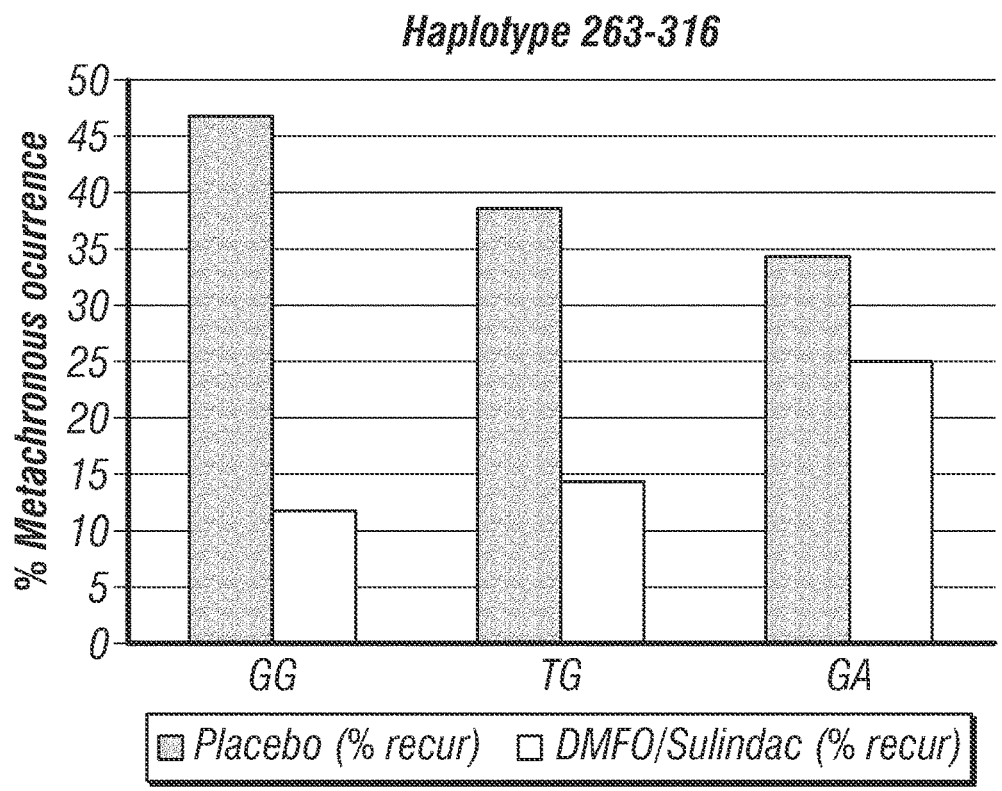
FIG. 12. Metachronous adenoma occurrence by ODC1 +263 and +316 SNP haplotype. Placebo and treatment groups are shown.

The effects of G-quadruplex stabilization by Sp1 alone was further studied in HCT116 cells. Using genetic manipulation to down regulate Sp1 expression, changes in luciferase expression from the ODC1 +263 G and T allele plasmids were examined. Down regulation of Sp1 led to differences in luciferase activity in the ODC1 plasmids (FIGS. 3 and 11). With the +263 T allele a non-statistically significant increase in (P>0.001) luciferase was observed as compared with the scramble siRNA. In contrast, with the +263 G a statistically significant increased (P=0.001) was observed as compared with the scramble siRNA, representing a 115% increase in luciferase activity. The down regulation was confirmed by western blot, where a 60% reduction in the Sp1 expression was observed, as compared with two random scramble siRNA or non-treated cells. In addition, full-length Sp1 protein was over-expressed using a mammalian expression vector (pN3). Sp1 protein had no effect or did not significantly down-regulate ODC1 expression (FIG. 11). In the control experiment, the T-allele-driven reporter produced more luciferase than the G-allele-driven reporter either with validated scramble siRNA or the empty expression vectors. Taken together with the in vitro data, in which the equilibrium between G-quadruplex and dsDNA was dependent on the concentration of the Sp1 protein, the overexpression of Sp1 protein maintained the ODC1 promoter-driven plasmid in a state of dsDNA, which is not responsive to higher concentrations of Sp1 protein. In contrast, knockdown of Sp1 expression favored the G-quadruplex conformation over dsDNA. The G-quadruplex conformation appears to repress the expression of ODC1-driven luciferase depending on the ODC1 +263 T or G allele G-quadruplex stability.

These results suggest a role of the G-quadruplex in the transcriptional regulation of ODC1. If a correlation exists between guanine or thymine at ODC1 +263 and a functional or biological outcome in colorectal cancer patients, an opportunity exists for the development of an ODC1-specific G-quadruplex stabilizing agent to decrease ODC1 expression in patients.

Example 2—Intron 1 Polymorphisms Cooperate to Modulate ODC1 Transcriptional Promoter Activity and Risk of Colorectal Adenomas Herein, the genetic variability of the ODC1 +263 SNP is functionally analyzed. The G-to-T transversion at this position is able to modulate both the stability of a G-quadruplex DNA secondary structure and an Sp1 binding site to functionally modulate the transcription of ODC1 (see Example 1). The functional contribution of this SNP, both individually and with the previously studied ODC1 +316 SNP, is studied, as well as its relationship with phenotype. Both SNPs determined limited common haplotypes, which are the most frequent among participants of the colorectal chemoprevention trial. The ODC1 +263 SNP, but not ODC1 +316 SNP or any diplotype, is able to predict putrescine levels in participants of the DFMO/sulindac clinical trial, which further validates its functionality. The ODC1 +263 TT genotype is associated with higher polyamine levels and better response to DFMO/sulindac treatment. In addition, evidence is presented showing both SNPs cooperating to modulate ODC1 transcriptional activity by Sp1 and c-MYC protein-protein interaction, involving an Sp1 binding site at rs2302616 and c-MYC binding sites around rs2302615 flanked E-boxes.

ODC1 Common Haplotypes are Determined Primarily by ODC1 +263 SNP (rs2302616).

A comprehensive investigation of ODC1 genetic variability was conducted in 196 participants of the colorectal cancer chemoprevention DFMO/sulindac clinical trial. Using the sequenom multiplex MassARRAY platform, the frequencies of 49 SNPs were confirmed. In addition, using allele-specific probe discrimination, the genotype at the ODC1 +263 SNP was determined, which failed with the previous genotyping platform. The high GC context in which it is located contributed to difficulty in its genotyping, as previously reported (Barry et al., 2011). Twelve SNPs were identified with minor allele frequencies (MAF) near 10% or more (Table 4). Using PHASE software, haplotypes were constructed using the clinical genotyping data and dbSNP CEPH database (Table 5). The same common limited haplotype structure in ODC1 was determined using both data sources and accounts for more than 90% of individuals. Only the ODC1 +263 SNP was able to subdivide the haplotype construction in two larger groups that do not further split ODC1 intron 1. Specifically, the ODC1 +263 SNP divided the haplotype structure into two groups that accounted for 25.5% and 30.1% of all participants in the clinical trial of polyp formers and 40.9% and 13.6% in the normal CEPH referent population. These two haplotypes together account for more than half of the study population and share a G-allele at the well-characterized ODC1 +316 SNP (Table 5, compare haplotype A and B). A third SNP, rs7559979, in intron 9 further sub-divided the larger of these two haplotypes (haplotype B, Table 5) into a C haplotype sharing a G-allele at ODC1 +263 SNP (rs2302616) and occurring at a frequency of 18.4% in trial participants and 22.7% in the CEPH database (Table 5, compare haplotype B and C). Linkage disequilibrium block structures constructed using Haploview software grouped all SNPs into the same block, with the exception of ODC1 +263 SNP (rs2302616) suggestive of selective pressure in ODC1 allelic structure to maintain a non-random association of alleles at different loci.

TABLE 4

SNPs producing "aggressive call" with a minor allele frequency (MAF) around ten percent or greater.
ODC1 SNPs Aggressive Calls

|   | SNPs | Base Change | MAF | Location |
|---|---|---|---|---|
| 1 | rs2302616* | G → T | 0.260 | Intron 1 |
| 2 | rs2302615 | G → A | 0.291 | Intron 1 |
| 3 | rs7558559 | A → T | 0.128 | Intron 1 |
| 4 | rs7608353 | T → C | 0.122 | Intron 1 |

TABLE 4-continued

SNPs producing "aggressive call" with a minor allele frequency (MAF) around ten percent or greater.
ODC1 SNPs Aggressive Calls

|   | SNPs | Base Change | MAF | Location |
|---|---|---|---|---|
| 5 | rs12616336 | T → C | 0.102 | Intron 1 |
| 6 | rs2302614 | T → G | 0.097 | Exon 2 |
| 7 | rs2302613 | A → G | 0.128 | Exon 2 |
| 8 | rs3752661 | A → G | 0.092 | Intron 6 |
| 9 | rs1405948 | G → A | 0.148 | Intron 9 |
| 10 | rs2357550 | A → G | 0.122 | Intron 9 |
| 11 | rs7559979 | T → C | 0.408 | Intron 9 |
| 12 | rs1049500 | G → A | 0.097 | Exon 13 |

*Failed on Sequenom multiplex MassARRAY platform. Re-genotyped with PCR/pyro-sequencing.
SNPs genotyping was performed using sequenom MassARRAY iPLEX.
ODC1 SNP +263 genotyping was performed by EpigenDx using pyrosequencing.

TABLE 5

Limited common ODC1 haplotypes are present in the population. SNPs are numbered 1 to 12 as in Table 4.
Common ODC1 Haplotypes

| | | | | | | | | | | | | Haplotype (N = 196) | |
|---|---|---|---|---|---|---|---|---|---|---|---|---|---|
| 1* | 2 | 3 | 4 | 5 | 6 | 7 | 8 | 9 | 10 | 11 | 12 | Percent (%) | Name |
| DFMO/Sulindac Trial | | | | | | | | | | | | | |
| T | G | A | T | T | T | A | A | G | A | T | G | 25.5 | (A) |
| G | G | A | T | T | T | A | A | G | A | T | G | 30.1 | (B) |
| G | A | A | T | T | T | A | A | G | A | C | G | 18.4 | (C) |
| G | G | T | C | C | T | G | A | A | G | C | G | 9.69 | (D) |
| G | A | A | T | T | G | A | G | G | A | C | A | 9.18 | (E) |
| dbSNP CEPH Data | | | | | | | | | | | | | |
| T | G | A | T | T | T | A | A | G | A | T | G | 40.9 | (A) |
| G | G | A | T | T | T | A | A | G | A | T | G | 13.6 | (B) |
| G | A | A | T | T | T | A | A | G | A | C | G | 22.7 | (C) |
| G | G | T | C | C | T | G | A | A | G | C | G | 11.4 | (D) |
| G | A | A | T | T | G | A | G | G | A | C | A | 9.10 | (E) |

Number 1 is ODC1 SNP +263 and number 2 is ODC1 SNP +316. The "aggressive call" SNPs from DFMO/sulindac clinical trial (top) and public data base CEPH (bottom) were phased using PHASE and Haploview software to predict the most common haplotypes.
*Failed on Sequenom multiplex MassARRAY platform and was re-genotyped with PCR-pyrosequencing.

ODC1 Haplotypes and Diplotypes in Relation to Metachronous Adenoma, Response to Treatment with DFMO/Sulindac, and Polyamine Levels.

Figure 13A:
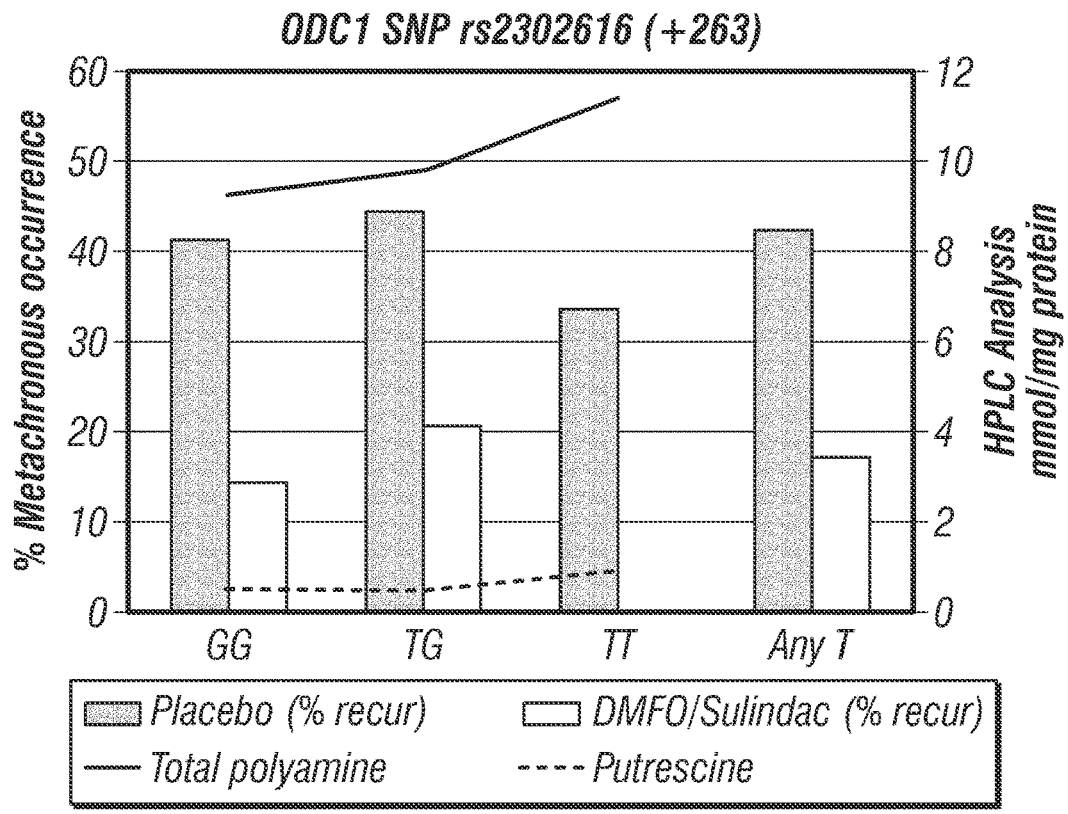
FIGS. 13A-B. Percentage metachronous adenoma, treatment response, and polyamine levels by ODC1 +263 (A) and +316 (B) SNPs. Black bars show the placebo group; white bars show the DFMO/sulindac treatment group. Total polyamine (black line) and putrescine pools (gray line) are also shown by genotype. N=307.
Figure 13B:
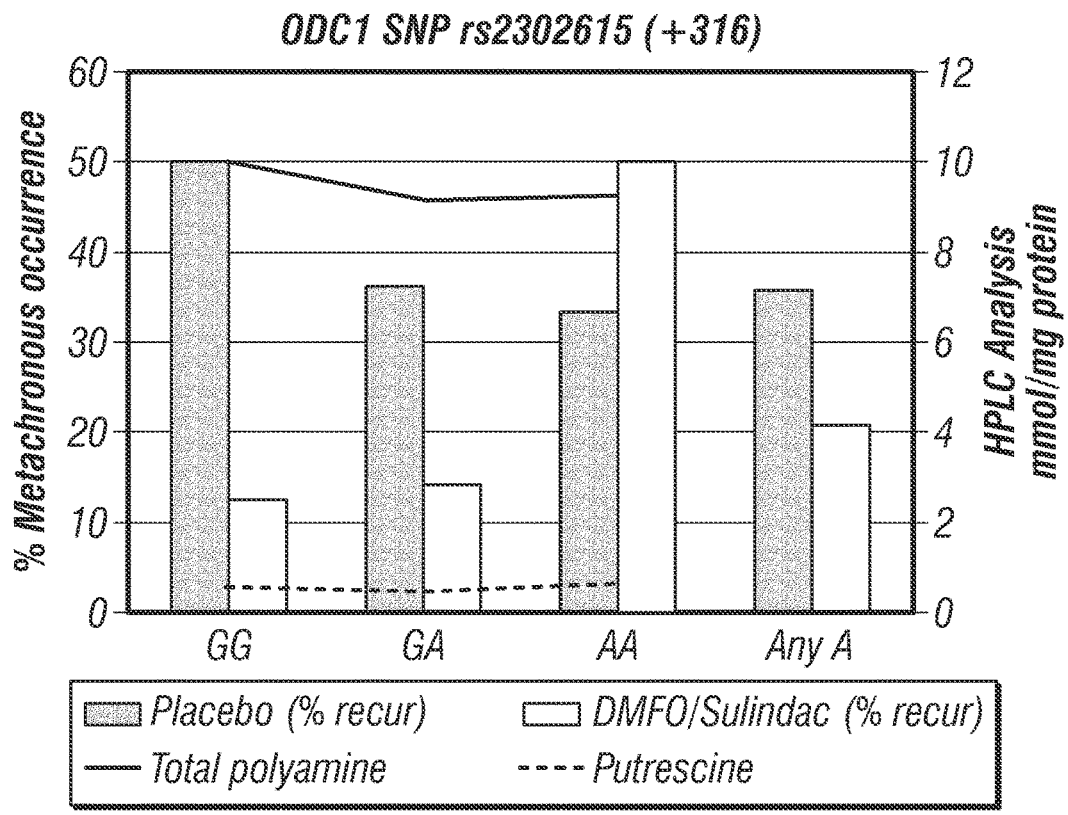

Haplotype construction using either clinical trial participants or CEPH genotypes failed to identify the co-occurrence of a T-allele in ODC1 at the +263 with an A-allele at ODC1 +316; results suggest that if this combination occurs it is present in >0.5% (Divide 1/total of CEPH plus Clinical Trial). The ODC1 +316 genotype distribution in DFMO/sulindac clinical trial participants was previously reported as 130 GG (55.8%), 88 GA (37.8%), and 15 AA (6.4%) (Zell et al., 2010). Here, the ODC1 +263 genotype distribution was 122 GG (52.1%), 90 TG (38.5%), and 22 TT (9.4%). Data from 463 participants of the DFMO/sulindac clinical trial showed ODC1 SNP 263-316 haplotypes of GG (N=217, 46.9%), TG (N=129, 27.9%), and GA (N=117, 25.2%). Using a dominant model for ODC1 SNP+316 (GG versus GA/AA), a statistically significant interaction between genotype and DFMO/sulindac treatment on metachronous adenoma was previously shown (Zell et al., 2010). Individuals homozygous for the G-allele had lower risk of adenoma recurrence after treatment than those homozygous or heterozygous for the A-allele (p<0.0001; FIG. 13B and Table 7, bottom). When the same analysis was conducted for ODC1 SNP+263, similar associations were observed (FIG. 13A and Table 7, top). Stratification by genotype demonstrated a statistically significant benefit for treatment using a dominant model.

Figure 14:
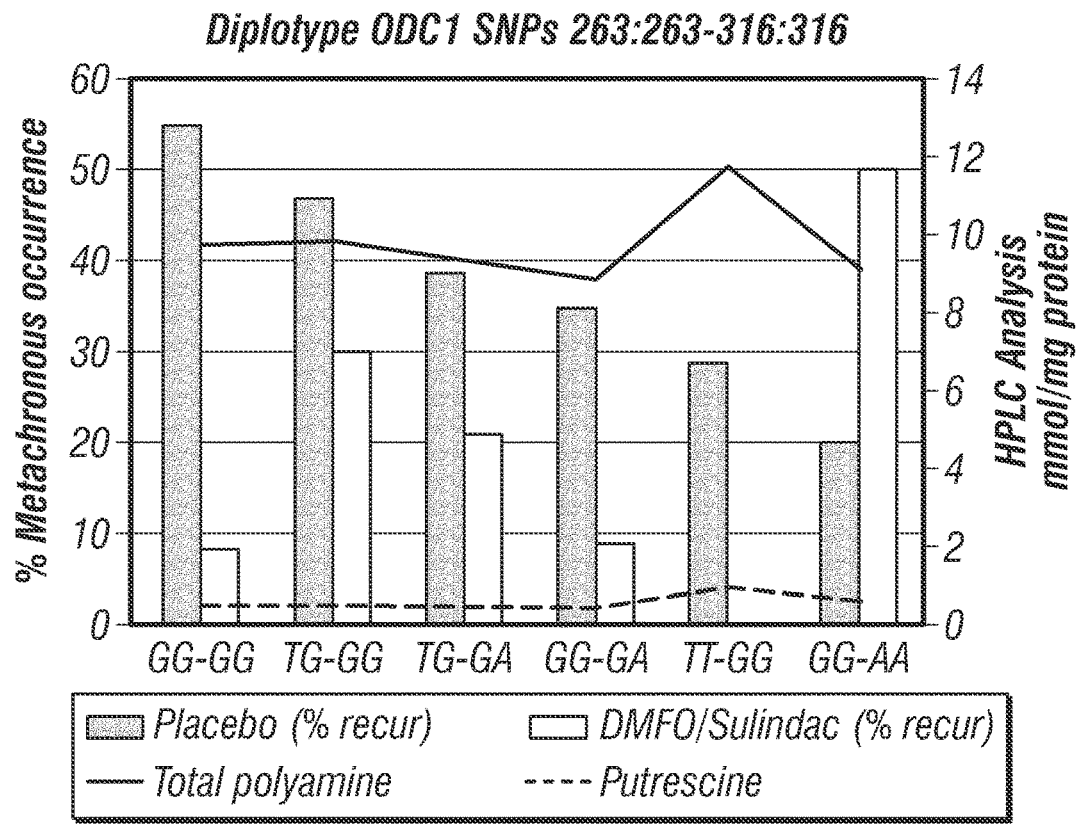
FIG. 14. Percentage metachronous adenoma, treatment response, and polyamine levels by ODC1 +263 and +316 SNP diplotype. Black bars show the placebo group; white bars show the DFMO/sulindac treatment group. Total polyamine (black line) and putrescine pools (gray line) are also shown by genotype. N=217.
Figure 15A:
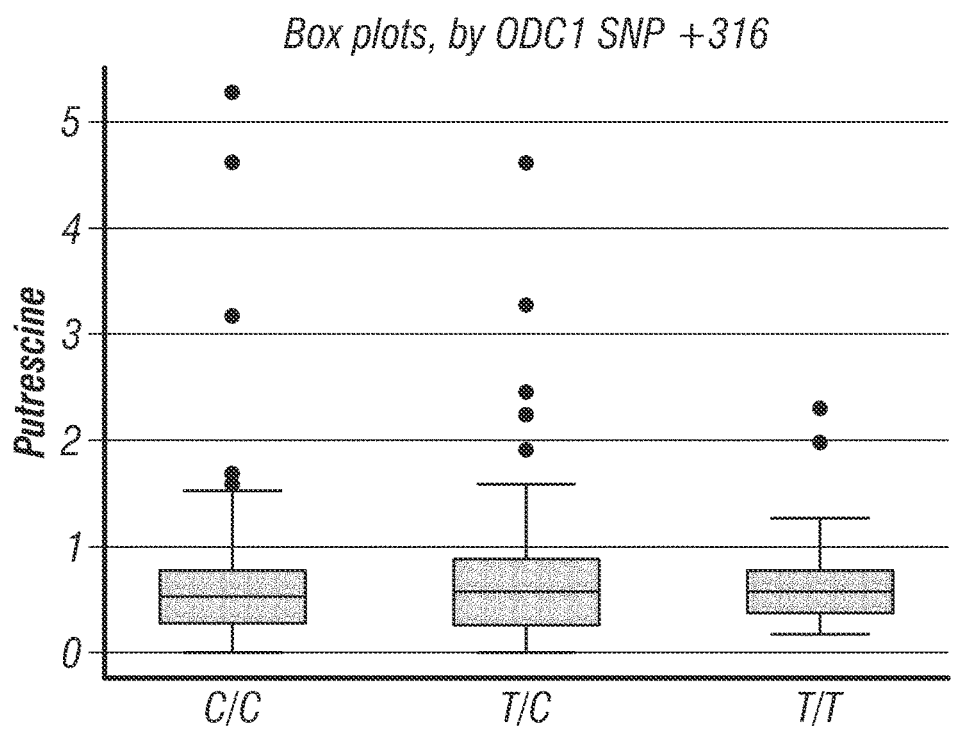
FIGS. 15A-B. Polyamine measurements by ODC1 +263 (B) and +316 (A) SNPs by genotype presented as box plots. Note that the sequence of the opposite strand is reported.
Figure 15A:
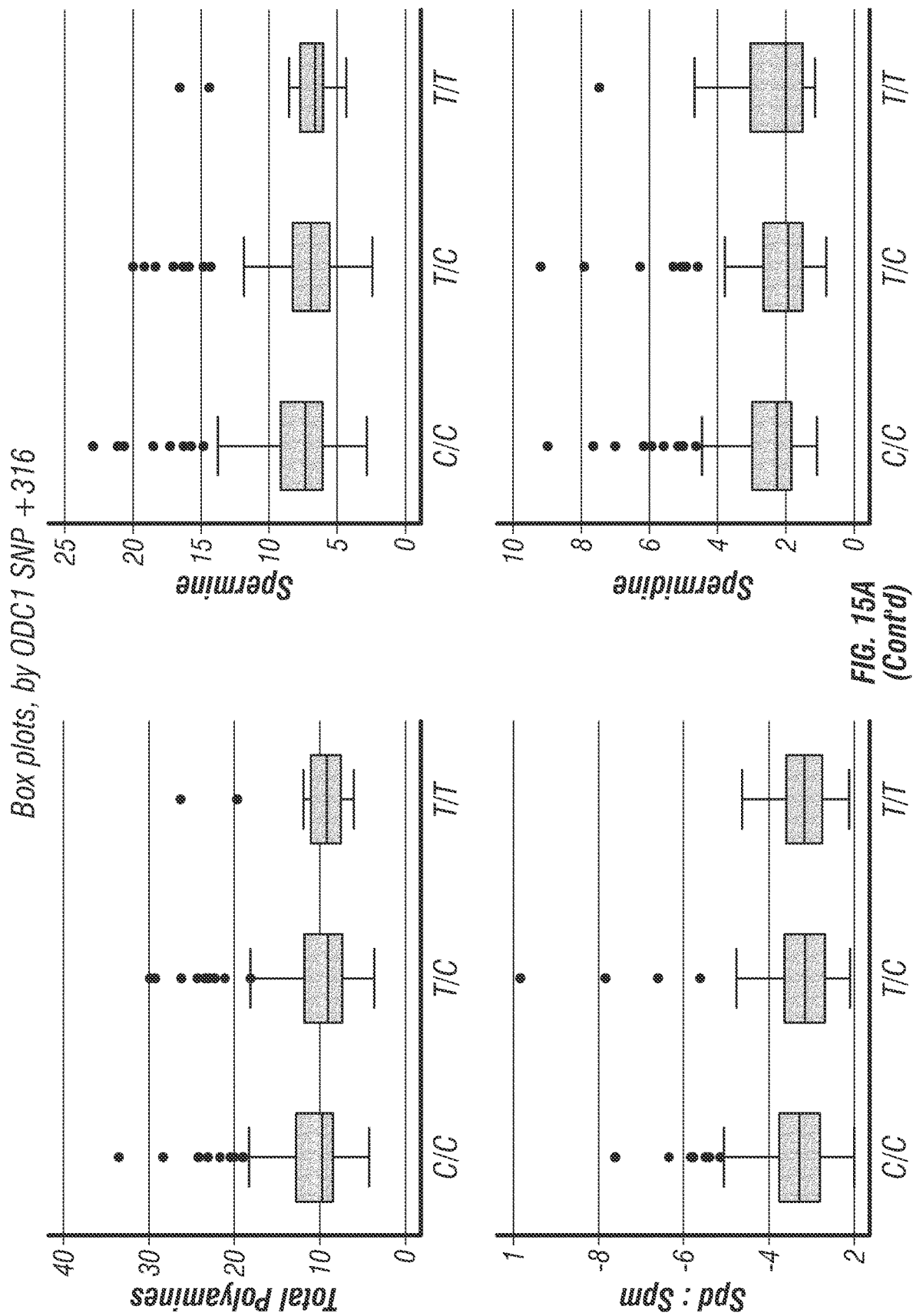
Figure 15B:
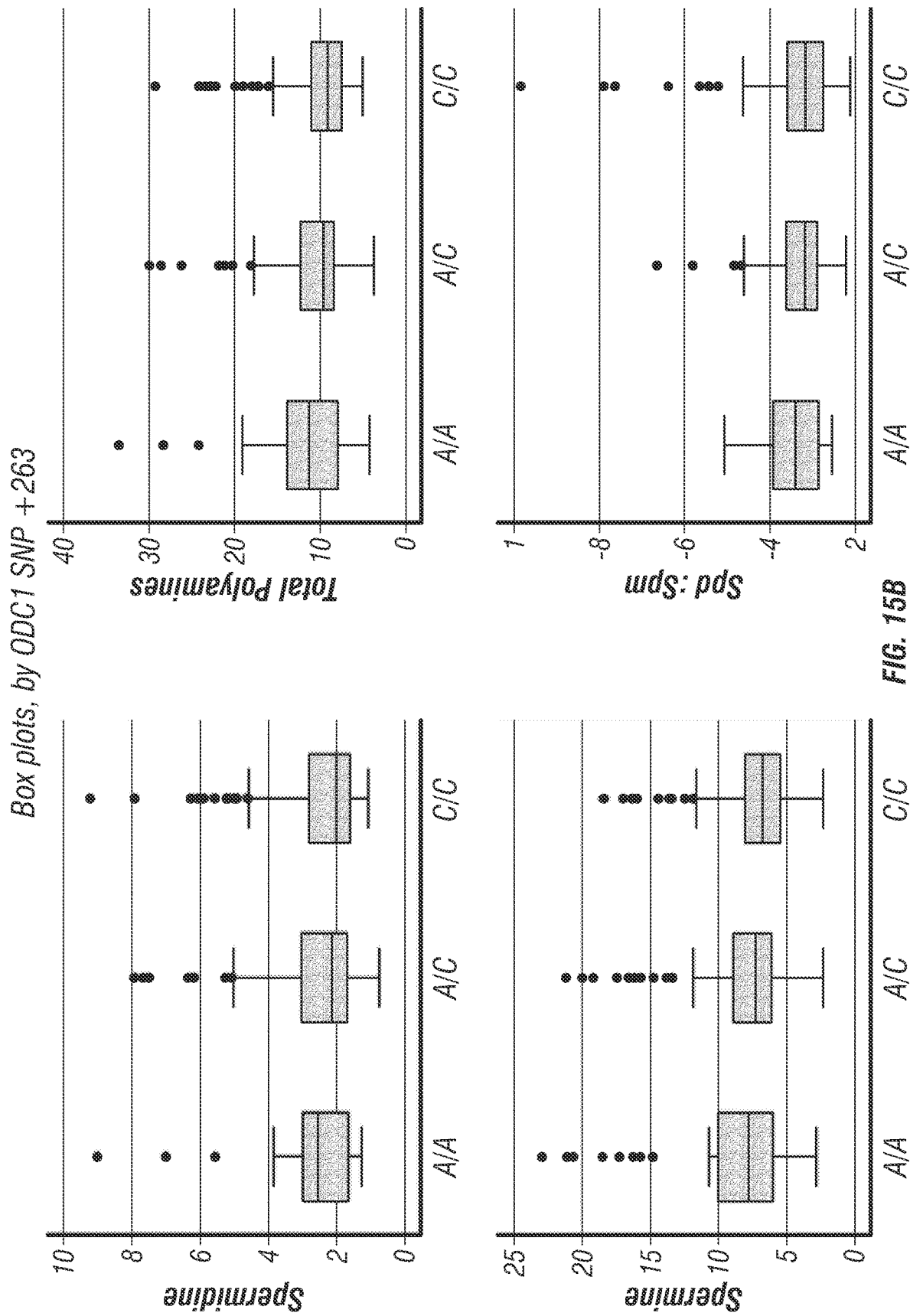
Figure 15B:
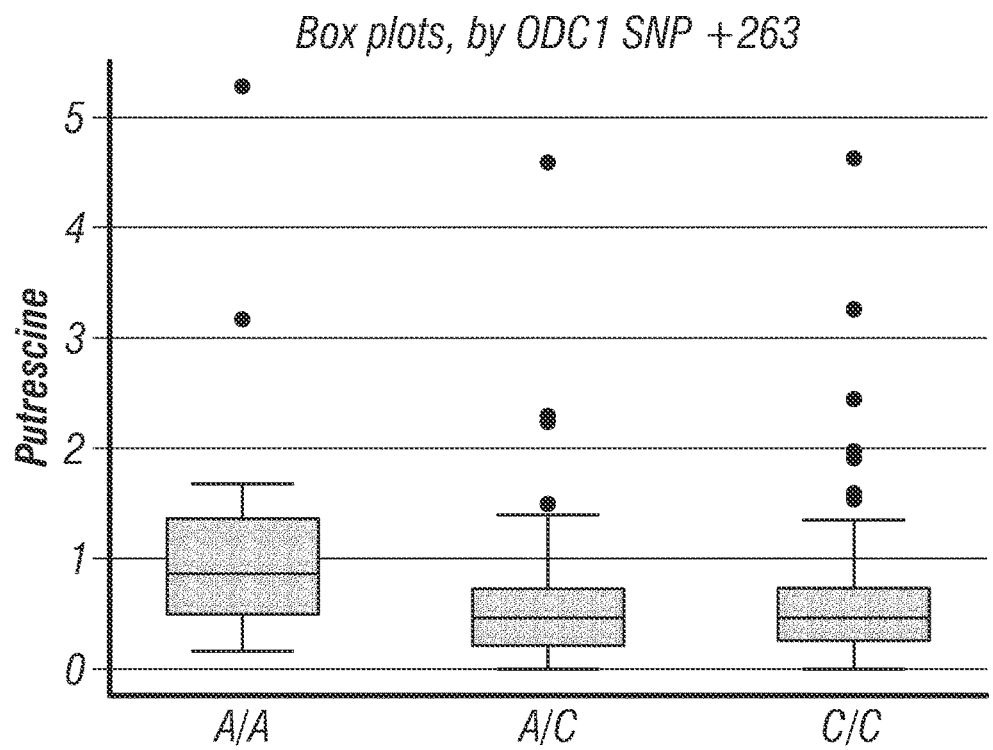

Using a recessive model, stratification by genotype demonstrated a statistically significant benefit of treatment in individuals who carried two TT alleles at +263 when compared to carriers of any T (P=0.0001). To determine whether or not the modification of treatment response observed for +316 and +263 were acting jointly, haplotypes were assessed based on +263 and +316 and treatment response. The distribution of ODC1 +263 and +316 diplotypes (263:263-316:316) was 53 GG-GG (22.8%), 56 TG-GG (24.1%), 33 TG-GA (14.2%), 55 GG-GA (23.7%), 20 TT-GG (8.6%), and 14 GG-AA (6.0%). Only one participant was found to have the diplotype TG-AA, which was excluded from the analysis, and no participant was found with TT-AA or TT-GA. Some diplotypes are expected to be lower in frequency since they do not have the ancestral allele at ODC1 +263 or +316. In addition, a better resolution of the risk/benefit ratio for both ODC1 +263 and +316 SNPs was found (FIG. 14 and Table 8), which allows for a better decision of chemoprevention with DFMO/sulindac. Due to the small sample size of each diplotype group, there was not enough power to conclude with statistical significance. A gradual effect of the diplotype itself was observed in the placebo and treatment group, which is associated with decreased and increased risk of the metachronous adenoma, respectively. Taken together with the benefit/risk ratio of each group, a better decision regarding treatment can be made for the use of DFMO/sulindac chemoprevention.

Figure 16:
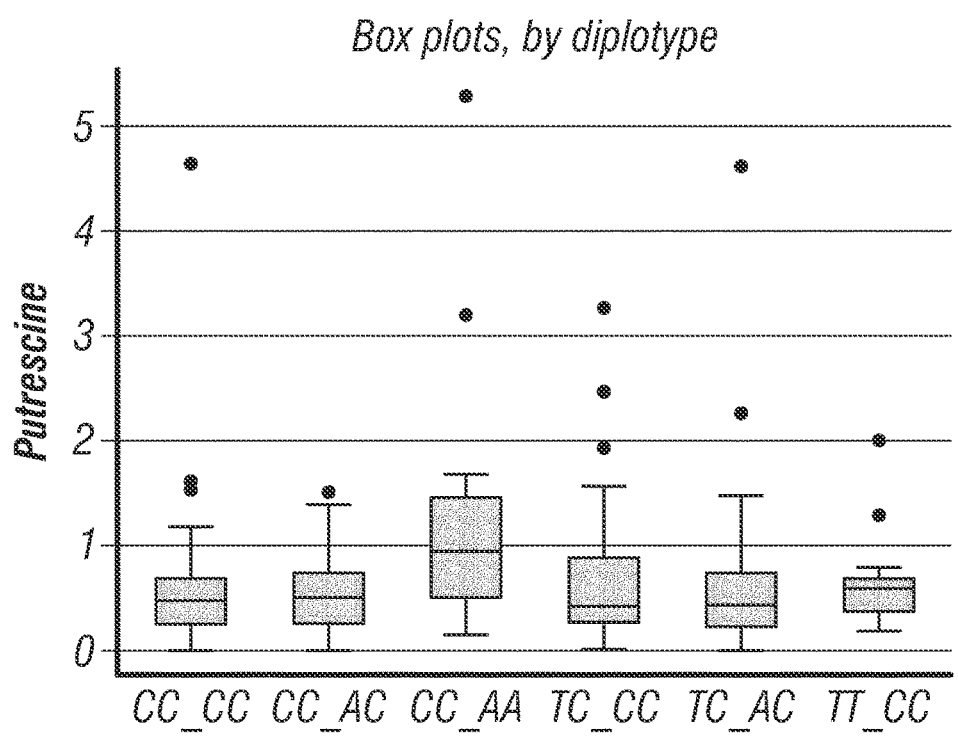
FIG. 16. Polyamine measurements by diplotype 316/316-263/263 presented as box plots. Note that the sequence of the opposite strand is reported.
Figure 16:
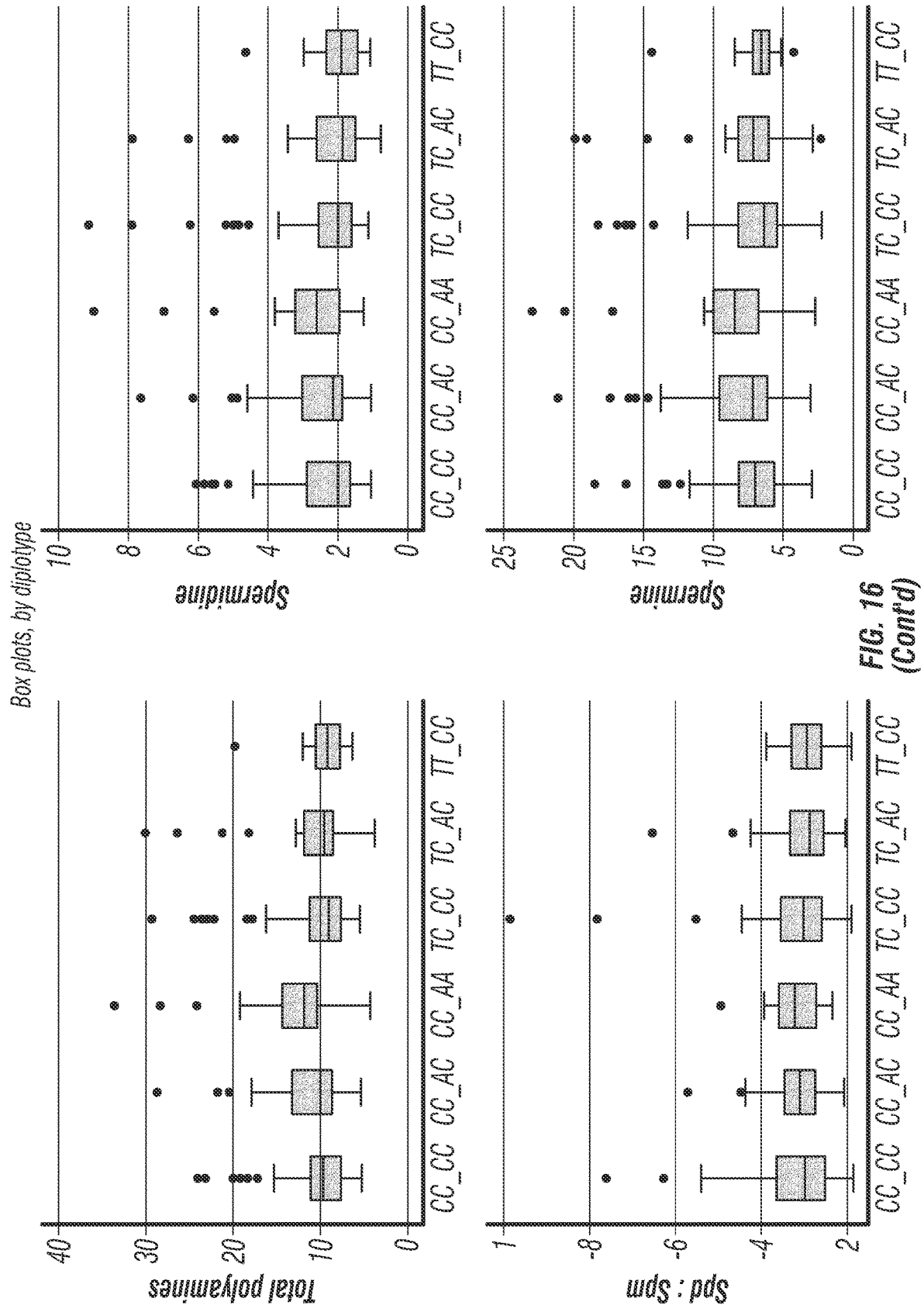

Next, whether genetic variation at ODC1 +263 and/or +316 was associated with polyamine levels in normal tissue biopsies of trial participants was assessed. If genetic variation in ODC1 +263 and/or +316 play a critical role in the transcriptional regulation of ODC1, then steady tissue polyamine content would be dependent on the allelic structure of ODC1 at +263 or +316, or dependent on the sequence at both, given the evidence for relatively strong linkage between the two SNPs. ODC1 +316 genotype was not significantly associated with either tissue putrescine concentrations or the spermidine-to-spermine ratio (Zell et al., 2009). In contrast, when ODC1 +263 was assessed, a statistically significant association was found between baseline tissue putrescine level and +263 genotype. In a recessive model, the ODC1 +263 TT genotype carriers had higher polyamine levels than carriers of GG/GT (P<0.015) (FIGS. 13A-B, 15A-B, and 22; Tables 9 and 10, top). In addition, little evidence was found for a joint effect of ODC1 +263 and +316 diplotype and tissue polyamine levels where only the TT-GG diplotype carriers had non-significantly higher baseline tissue putrescine content compared to the common diplotype TG-GG (P=0.085) (FIGS. 14 and 16; Table 9). These results suggest that the ODC1 +263 SNP, as opposed to the previously implicated +316 SNP, is important in determining the putrescine pool in normal tissues.

TABLE 6

Metachronous adenoma occurrence by ODC1 +263 and +316 haplotype.

| rs2302606/ rs2302615 | Placebo | | | DFMO/sulindac | | | RR | M-H |
|---|---|---|---|---|---|---|---|---|
| +263/+316 | N | Total | % | N | Total | % | (95%) | test P |
| GG | 49 | 90 | 46.7 | 12 | 90 | 11.8 | | |
| TG | 19 | 49 | 38.8 | 9 | 62 | 14.5 | | |
| GA | 20 | 58 | 34.5 | 13 | 52 | 25 | | |

Placebo and treatment groups are shown.

TABLE 7

DFMO/sulindac efficacy, stratified by ODC1 +263 (top) and +316 (bottom) genotype.

| | Placebo | | | DFMO/sulindac | | | RR | M-H |
|---|---|---|---|---|---|---|---|---|
| | N | Total | % | N | Total | % | (95% CI) | test P |
| rs2302616 +263 | | | | | | | | |
| GG | 23 | 56 | 41.1 | 8 | 55 | 14.6 | | |
| TG | 16 | 36 | 44.4 | 9 | 44 | 20.4 | | |
| TT | 3 | 9 | 33.3 | 0 | 9 | 0 | | |
| Any T | 19 | 45 | 42.2 | 9 | 53 | 17 | | |
| rs2302615 +316 | | | | | | | | |
| GG | 23 | 47 | 50 | 8 | 64 | 12.5 | | |
| GA | 17 | 47 | 36.2 | 5 | 36 | 13.9 | | |
| AA | 2 | 6 | 33.3 | 4 | 8 | 50 | | |
| Any A | 19 | 53 | 36.5 | 9 | 44 | 20.5 | | |

TABLE 8

DFMO/sulindac efficacy, stratified by ODC1 diplotype (N = 191).

| | Placebo | | | DFMO/sulindac | | | RR | M-H |
|---|---|---|---|---|---|---|---|---|
| Diplotype | N | Total | % | N | Total | % | (95% CI) | testP |
| GG-GG | 12 | 22 | 54.6 | 2 | 25 | 8. | 0.09 (0.01-0.61) | 0.258 |
| TG-GG | 8 | 18 | 44.4 | 6 | 30 | 20 | 0.38 (0.15-0.97) | |
| TT-GG | 2 | 17 | 28.6 | 0 | 9 | 0 | n/a | |
| GG-AG | 10 | 29 | 34.5 | 2 | 22 | 9.1 | 0.28 (0.07-1.13) | |
| TG-AG | 7 | 17 | 41.2 | 3 | 14 | 21.4 | 0.61 (0.20-1.88) | |
| GG-AA | 1 | 5 | 20 | 4 | 8 | 50 | 2.00 (0.31/13.1) | |

TABLE 9

Baseline putrescine levels are statistically associated with ODC1 +263 (rs2302616) genotype.

| 316_263 Diplotype | GG_GG N = 53 | GG_GT N = 55 | GG_TT N = 20 | GA_GG N = 54 | GA_GT N = 33 | AA_GG N = 14 | P* |
|---|---|---|---|---|---|---|---|
| Spermidine | 2.47 ± 1.3 (2.01) | 2.58 ± 1.2 (2.11) | 3.11 ± 2.0 (2.59) | 2.54 ± 1.6 (2.00) | 2.44 ± 1.6 (1.85) | 2.09 ± 0.9 (1.91) | 0.169 |
| Spermine | 7.58 ± 3.1 (7.03) | 8.11 ± 3.6 (7.12) | 9.54 ± 5.1 (8.44) | 7.73 ± 3.6 (6.41) | 7.81 ± 3.8 (7.07) | 6.97 ± 2.4 (6.43) | 0.239 |
| Spd:Spm | 0.33 ± 0.1 (0.30) | 0.32 ± 0.1 (0.31) | 0.32 ± 0.1 (0.32) | 0.33 ± 0.1 (0.30) | 0.31 ± 0.1 (0.29) | 0.29 ± 0.1 (0.29) | 0.618 |
| Putrescine | 0.61 ± 0.7 (0.48) | 0.53 ± 0.4 (0.50) | 1.20 ± 1.2 (0.94) | 0.70 ± 0.7 (0.42) | 0.68 ± 0.9 (0.43) | 0.67 ± 0.5 (0.60) | 0.085 |
| Total | 10.7 ± 4.3 (9.79) | 11.2 ± 4.8 (9.88) | 13.9 ± 7.3 (11.8) | 11.0 ± 5.6 (8.91) | 10.9 ± 5.6 (9.34) | 9.73 ± 3.3 (9.14) | 0.133 |

Normal (tumor-free) rectal mucosal biopsies were obtained at baseline to measure polyamine content. The tissue were homogenized in 0.2N perchloric acid. The acid-soluble fraction containing polyamines were separated using reverse-phase ion pair HPLC, and normalized to acid insoluble protein content.
*P-values calculated from non-parametric Kruskal-Wallis tests of mean ± SD (comparison of medians).

TABLE 10

Baseline putrescine levels are statistically associated with the ODC1 +263 (rs2302616) and not with the ODC1 +316 (rs2302615) genotype. Box-plot of the ODC1 +263 SNP data are provided in FIG. 22.
Baseline polyamine levels in DFMO/sulindac (mean ± SD (median))

| rs2302616 (+263) | GG N = 121 | GT N = 89 | TT N = 22 | P* |
|---|---|---|---|---|
| Spermidine | 2.46 ± 1.4 (1.99) | 2.58 ± 1.5 (2.08) | 2.97 ± 1.9 (2.51) | 0.240 |
| Spermine | 7.57 ± 3.3 (6.69) | 8.09 ± 3.7 (7.12) | 9.11 ± 5.1 (7.82) | 0.119 |
| Spd:Spm | 0.32 ± 0.1 (0.30) | 0.32 ± 0.1 (0.30) | 0.32 ± 0.1 (0.32) | 0.668 |
| Putrescine | 0.66 ± 0.7 (0.48) | 0.61 ± 0.6 (0.48) | 1.14 ± 1.2 (0.88) | 0.015 |
| Total | 10.7 ± 4.8 (9.25) | 11.3 ± 5.3 (9.80) | 13.2 ± 7.2 (11.4) | 0.081 |
| rs2302615 (+316) | GG N = 129 | GA N = 87 | AA N = 15 | P* |
| Spermidine | 2.61 ± 1.4 (2.17) | 2.51 ± 1.6 (1.97) | 2.45 ± 1.7 (1.97) | 0.181 |
| Spermine | 8.10 ± 3.7 (7.22) | 7.76 ± 3.6 (6.82) | 7.61 ± 3.33 (6.51) | 0.420 |
| Spd:Spm | 0.32 ± 0.1 (0.31) | 0.32 ± 0.1 (0.30) | 0.30 ± 0.1 (0.30) | 0.501 |
| Putrescine | 0.67 ± 0.7 (0.54) | 0.70 ± 0.7 (0.42) | 0.78 ± 0.6 (0.61) | 0.489 |
| Total | 11.4 ± 5.1 (9.91) | 11.0 ± 5.6 (9.15) | 10.8 ± 5.3 (9.25) | 0.271 |

Normal (tumor-free) rectal mucosal biopsies were obtained at baseline to measure polyamine content. The tissue were homogenized in 0.2N perchloric acid. The acid-soluble fraction containing polyamines were separated using reverse-phase ion pair HPLC, and normalized to acid insoluble protein content.
*P-values calculated from non-parametric Kruskal-Wallis tests of mean ± SD (comparison of medians).

ODC1 Allele-Specific Promoter Activity Validates the Importance of Both ODC1 +263 and +316 SNPs.

Figure 17:
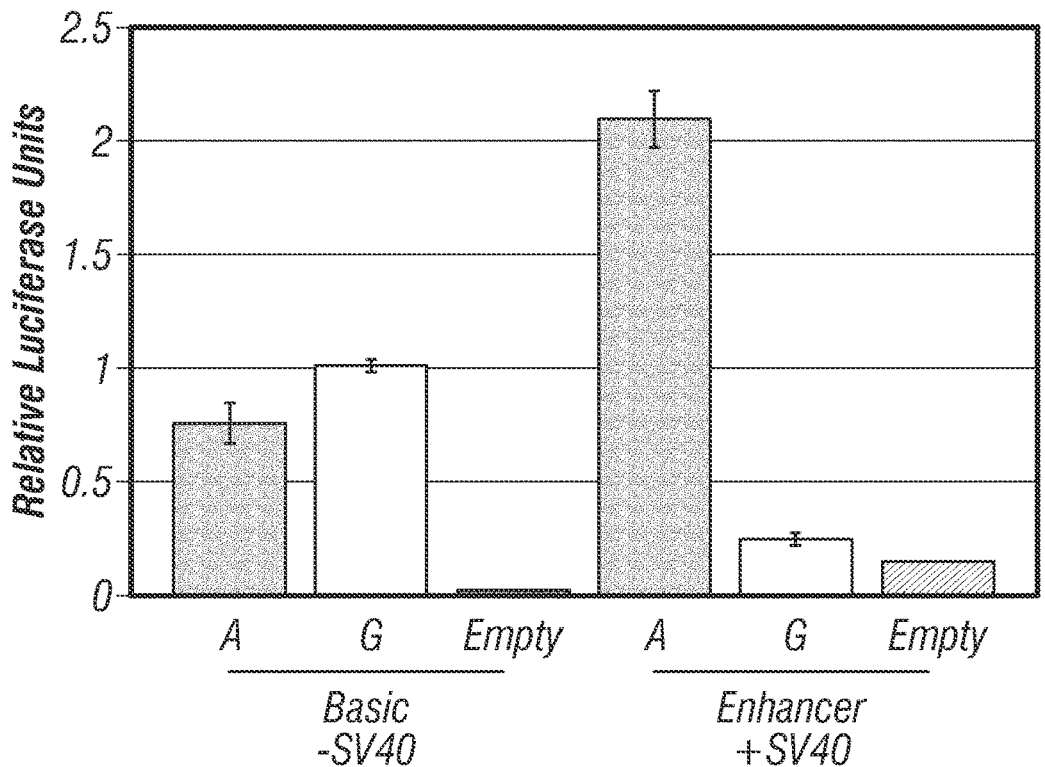
FIG. 17. Transfection experiments with isogenic ODC1 +263 and +316 SNPs. HCT116 cells were transfected with the 1.6 kb ODC1 promoter/intron 1 construct in the pGL3-Basic plasmid. c-MYC co-transfection (pcDNA3-c-MYC) showed increased luciferase activity, as compared with the empty vector (pcDNA3-Empty). *Renilla* luciferase was used to normalize for differences in transfection efficiency.

The ODC1 +263 SNP is able to modulate the stability of a G-quadruplex structure and is associated with functional consequences for transcription using isogenic luciferase reporter plasmids using the reported functional A-allele at ODC1 +316 (see Example 1). In addition, the ODC1 +263 SNP is able to predict the rate-limiting product putrescine by genotype in the DFMO/sulindac trial. Several association studies correlate the ODC1 +316 SNP with different colorectal cancer outcomes and phenotypes, but not with putrescine levels. Since the ODC1 +316 SNP has been shown to be functional at the level of transcription, the molecular mechanism proposed for ODC1 +316 SNP was reevaluated. It was unexpected that both SNPs have different abilities in predicting putrescine levels being that they are in linkage. Genetic variation at the +316 site of intron 1 in ODC1 was previously reported to alter transcriptional activity using isogenic plasmids with the ODC1 +263 G-allele in an SV40 enhancer background (pGL3-Enhancer Promega). In contrast, the isogenic plasmids used here to study the role of the ODC1 +263 SNP were in an SV40 enhancer-less background (pGL3-Basic, Promega). This led to the possibility that the SV40 enhancer element may affect the ODC1-driven luciferase plasmid. Experiments were performed in the presence and absence of the SV40 enhancer to test this hypothesis in HCT116 (FIG. 17) and HT29 colon cancer cell lines. The SV40 enhancer element was responsible for statistically significant transcriptional activation of the ODC1 +316 A-allele in comparison to the ODC1 +316 G-allele. In addition, the pGL3-Basic plasmid ODC1 +316 G-allele drove slightly more luciferase activity than the ODC1 +316 A-allele. The ODC1 +263 G-allele was used, as it was in previous studies, because the presence of the ODC1 +263 T-allele with the ODC1 +316 A-allele diplotype was previously unknown.

Figure 21:
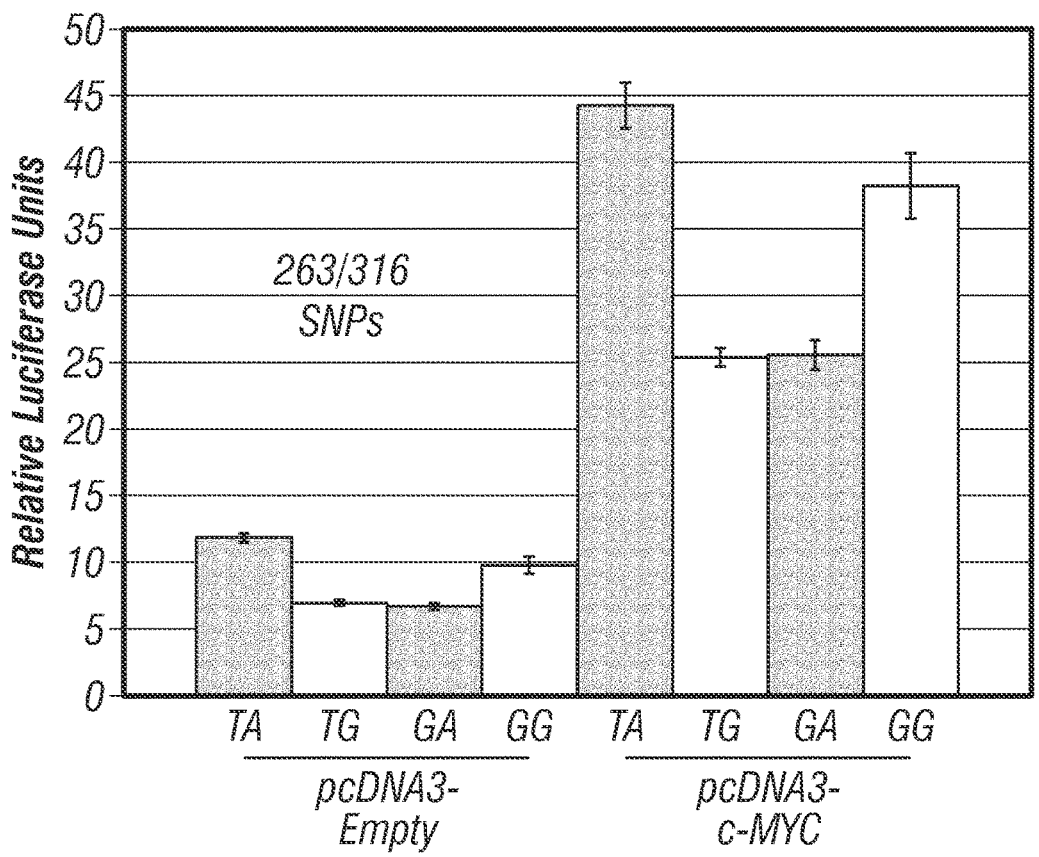
FIG. 21. Transfection experiment with isogenic ODC1 SNP+263 and +316. HCT116 cells were transfected with the 1.6 kb ODC1 promoter/intron 1 constructs in the pGL3-Basic plasmid. c-MYC co-transfection (pcDNA3-c-MYC) showed increased luciferase activity, as compared with the empty vector (pcDNA3-Empty). *Renilla* luciferase was used to normalize for differences in transfection efficiency.
Figure 22:
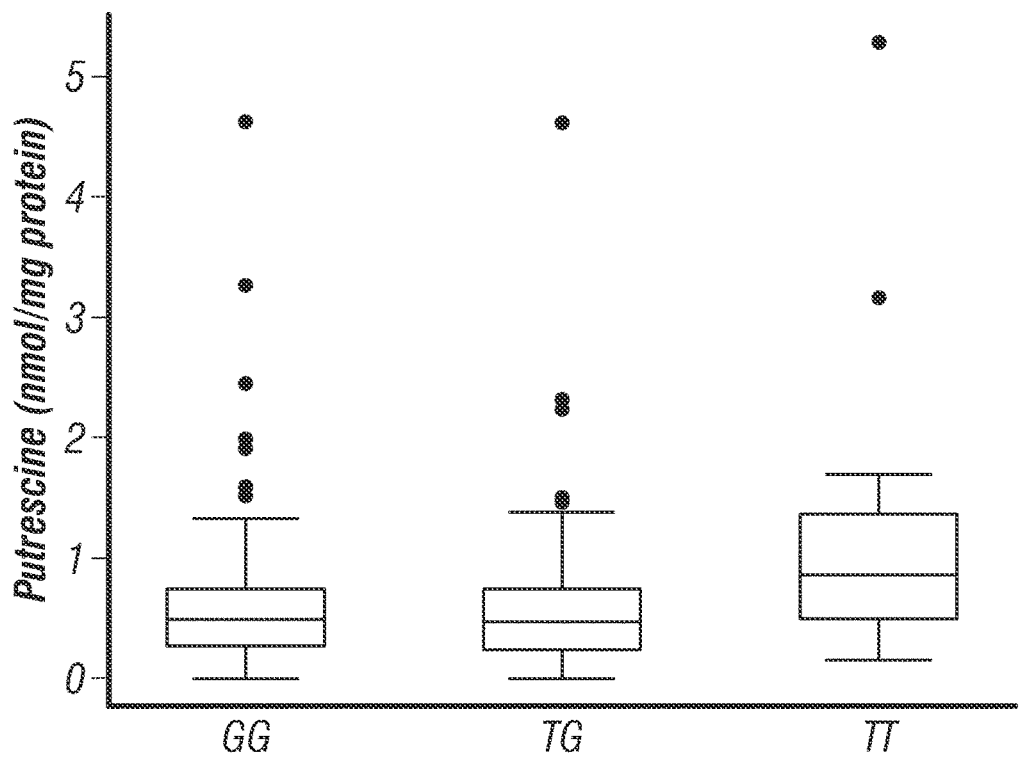
FIG. 22. Baseline putrescine levels are associated with ODC1 SNP+263 (rs2302616) genotype. *P-values calculated from non-parametric Kruskal-Wallis tests (comparison of medians). Data correspond to those presented in Table 10, top.

Site-directed mutagenesis was used to create all combinations of the ODC1 +263 and +316 SNPs in the absence of the SV40 enhancer (pGL3-Basic). Co-transfection experiments were performed in HCT116 cells with all four ODC1- driven luciferase reporter plasmids (haplotypes TA, TG, GA, and GG in ODC1 +263 and +316 SNPs, respectively) along with c-MYC, a known ODC1 transcriptional activator (Bello-Fernandez et al., 1993) (FIG. 21). The TA promoter reporter drove the highest luciferase activity, followed by GG with TG and GA exhibiting similar luciferase activities at lower levels than other genetic backgrounds. The addition of c-MYC resulted in activation of all versions of the plasmid at largely equal levels of luciferase activity. These observations contrast with the previously publish mechanisms of action for the ODC1 +316 SNP, in which the A-allele was associated with higher transcriptional activation and the ODC1 +316 A-allele specificity in co-transfection experiments in the presence of c-MYC.

Figures 19A, 19B:
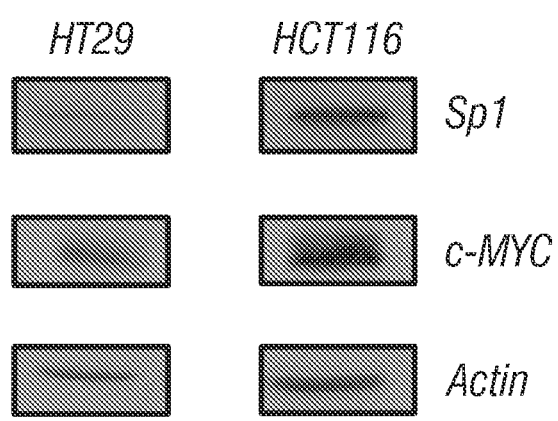
FIGS. 19A-D. Protein expression, cell line genotype, ChIP and co-IP in colon-derived cell lines. (A) HT29 and HCT116 cell line genotyping. DNA was obtained from both cell lines, and the region surrounding the ODC1 +263 and +316 SNPs was sequenced by direct DNA sequencing. A PstI restriction enzyme site created by the ODC1 +316 A-allele was also used. (B) Protein expression in HT29 and HCT116 cell lines by Western blot analysis. Total extracts of both cell lines were evaluated for the expression of Sp1 and c-MYC transcription factors. Actin was used as a loading control. (C) Documentation of allele-specific transcription factor binding by chromatin immunoprecipitation (ChIP) analysis. ChIP assays were performed using Upstate Biotech commercial kits, as recommended by the manufacturer. The sequences of the ODC1 primers used for PCR were 5'-CCTGGGCGCTCTGAGGT-3' (17mer; SEQ ID NO: 4) and 5'-AGGAAGCGGCGCCTCAA-3' (17mer; SEQ ID NO: 5). Visible ODC1 promoter-specific PCR products were obtained from HT29 DNA, but not HCT116 DNA, after immunoprecipitation of chromatin with antibodies directed against Sp1 and c-MYC transcription factor proteins. Input was used as a positive control and normal IgG as a negative control. (D) Documentation of allele-specific transcription factor interaction by co-immunoprecipitation (co-IP) analysis. Co-IP assays were performed using Upstate Biotech commercial kits, as recommended by the manufacturer. HT29 and HCT116 nuclear extracts were immunoprecipitated with antibodies directed against Sp1 and c-MYC. Membranes were blotted for c-MYC protein. Normal IgG was used a negative control in the immunoprecipitation assay.
Figure 19C:
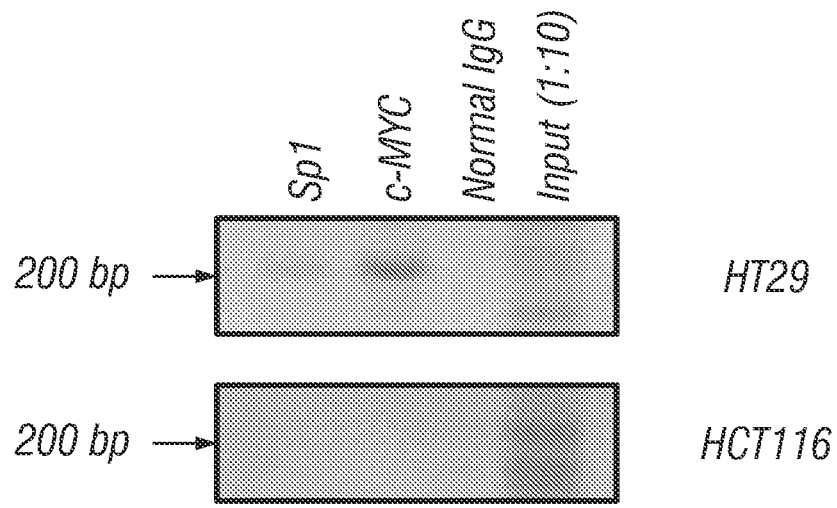
Figure 19D:
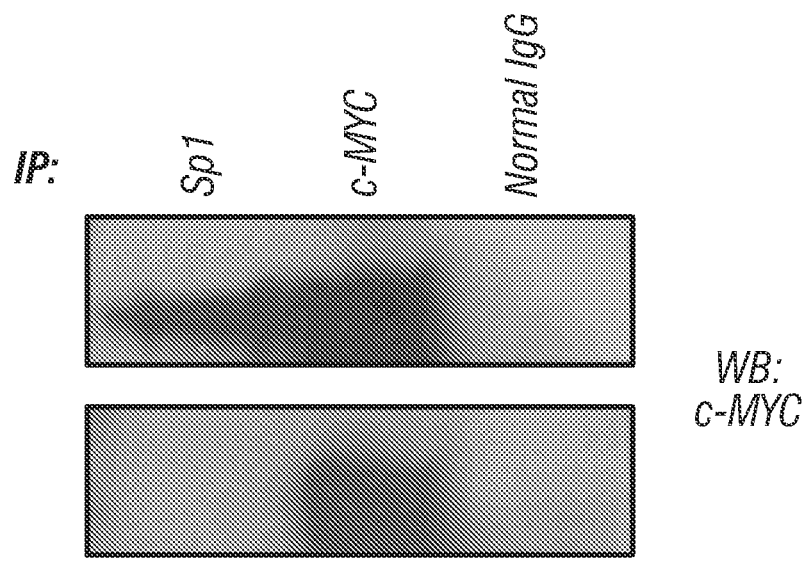

To address the molecular mechanism that might explain these observations, HT29 and HCT116 cell lines were compared, acknowledging the complicated interpretation considering different genetic backgrounds. As previously reported, both cell lines have convenient variation at ODC1 +263 and +316 SNPs (FIG. 19A) (Zell et al., 2009). Thus, the disruption of an Sp1 binding site at the ODC1 +263 SNP has functional consequences and mediates interactions with other transcription factors to activate ODC1 gene transcription. Previous evidence supports this hypothesis, since the Sp1 transcription factor has been shown to transactivate the rat odc gene (Kumar et al., 1995). To address this possibility, Sp1 and c-MYC protein expression was tested in both cell lines (FIG. 19B). Both cell lines expressed these transcription factors as expected. ChIP experiments were performed to study if both Sp1 and c-MYC transcription factors bind to ODC1 intron 1 in vivo. Both proteins bound ODC1 intron 1 in the HT29 cell line, as evidenced by a 200 bp ODC1-specific PCR product (FIG. 19C). In contrast, HCT116 cells showed much less binding of Sp1 and c-MYC, as previously shown (FIG. 19C) (Zell et al., 2009). These results are consistent with the hypothesis that the presence of both G-alleles at ODC1 +263 increases binding of Sp1 protein compared to only one G-allele at ODC1 +263. Having an A-allele at ODC1 +316 increased the binding of c-MYC protein, as previously demonstrated by isogenic ODC1 +316 in a pGL3-Enhancer background. In addition, co-immunoprecipitation experiments were performed to determine if both transcription factors are part of the same complex. Sp1 interacted with c-MYC in the HT29 cell line, but not in the HCT116 cell line (FIG. 19D). Thus, the HCT116 cell line was used to validate previous observations in the presence and absence of the SV40 enhancer using the isogenic plasmid ODC1 +263 G-allele and both ODC1 +316 SNP alleles.

Figure 20:
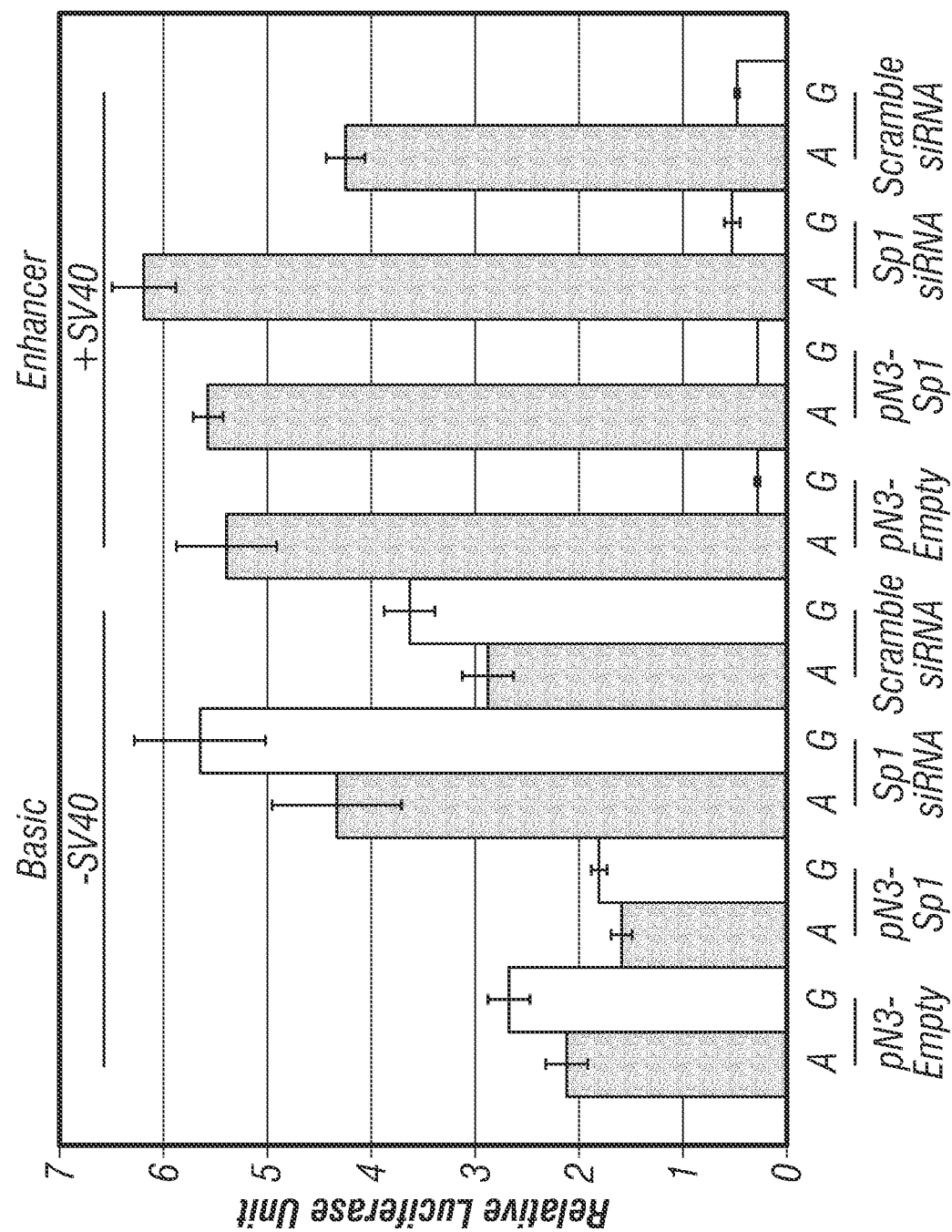
FIG. 20. Transfection experiment with isogenic ODC1 +263 and +316 SNPs in the pGL3-Basic and Enhancer plasmids. Overexpression of Sp1 full-length protein (pN3-Sp1) and the empty vector (pN3-Empty) was performed. Additionally, knockdown of Sp1 protein expression using Sp1 siRNA was performed and scramble siRNA was used as a control. *Renilla* luciferase was used to normalize for differences in transfection efficiency.

Even though the ChIP and co-IP experiments showed relatively low Sp1 and c-MYC promoter occupancy and no interactions by co-IP, whether Sp1 protein overexpression and down-regulation was able to modulate ODC1 transcription was further studied. Overexpression of Sp1 protein was associated with a slight repression in the basic plasmid, and that repression was lost in the presence of the SV40 enhancer (FIG. 20). In addition, Sp1 protein was down-regulated to validate previous observations. Consistently, increased luciferase activity was observed upon knockdown of Sp1 protein in the absence of the SV40 enhancer (FIG. 20). In presence of the SV40 enhancer, down regulation of Sp1 protein was associated with increased luciferase activity, especially with the A-allele at ODC1 +316. This confirmed the previous findings, in which the presence of a SV40 enhancer was affecting the interpretation of the isogenic plasmid, in which the presence of the SV40 enhancer created the allele specificity.

The N-Terminal Domain of the Sp1 Transcription Factor Interacts with c-MYC to Regulate ODC1 Transcriptional Activation.

Figure 18:
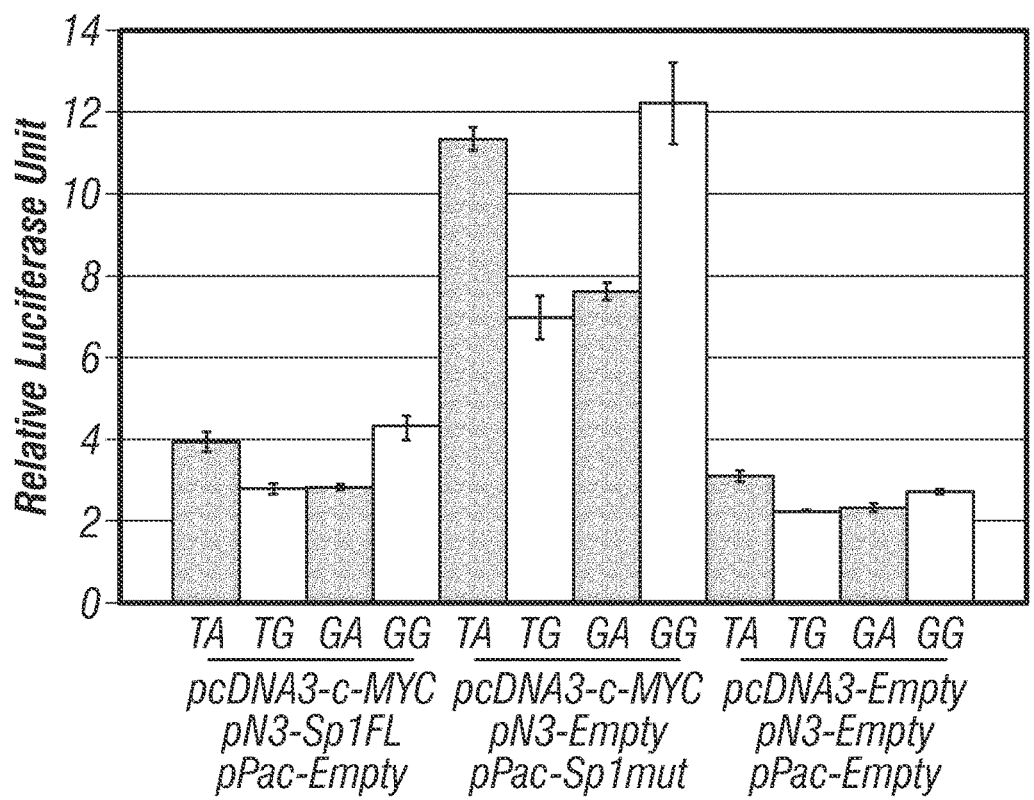
FIG. 18. Transfection experiments with isogenic ODC1 +263 and +316 SNPs in pGL3-Basic with overexpression of c-MYC (pcDNA3-c-MYC), Sp1 full-length protein (pN3-Sp1), and Sp1 N-terminal mutant (pPac-Sp1mut). Control experiment with corresponding empty vector is shown. *Renilla* luciferase was used to normalize for differences in transfection efficiency.

To study the interaction of Sp1 and c-MYC protein, their effect was directly tested in the transcription of ODC1 by transfection. Full-length Sp1 protein and a mutated version, which lacks the inhibitory domain in the N-terminal domain, was used in the presence of the isogenic basic plasmid (FIG. 18). Overexpression of c-MYC in the presence of full-length Sp1 down-regulated the expression of luciferase from the ODCJ-driven plasmid. In contrast, using the N-terminal mutated form of Sp1 in presence of c-MYC was associated with an up-regulation of luciferase expression. Thus, it is likely that an interaction between the N-terminal domain of Sp1 and c-MYC is responsible for the different transcriptional outcomes of ODC1. Even though no allele specificity was observed for activation in the isogenic plasmid, a preference for the ODC1 +263 and +316 TA and GG plasmids over the TG and GA plasmids was consistently observed.

The data presented here explain the different clinical associations observed across different clinical trials with regard to the predictive effect of the ODC1 +316 A-allele and metachronous adenoma, especially in aspirin users. It is possible that in the Barry et al. clinical trial (Barry et al., 2006) the majority of the population enrolled in the study was heterozygous for the T-allele at ODC1 +263, which gives a benefit of the DFMO/sulindac treatment, but not as good as having GG-alleles. Contrary, the population enrolled in the other two clinical trials may contain a higher representation of GG homozygotes at ODC1 +263 (Martinez et al., 2003; Hubner et al., 2008).

The present findings are in agreement with the oncogene addiction idea, in which a given oncogene in cancer cells may play a more essential and qualitatively different role in a given pathway or "module" compared with its role in normal cells (Weinstein and Joe, 2008). Statistically higher putrescine levels were found to be associated with the ODC1 +263 TT genotype, and when a treatment that targets the polyamine pathways was used, the best response was observed for this genotype. In summary, both ODC1 +263 and +316 SNPs affect the transcriptional regulation of ODC1, provide better resolution of the risk/benefit associated with treatment, and show that colorectal tumors likely depend on the overall polyamine content to be responsive to polyamine-targeted precision therapy.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Alberts et al., *J. Cell. Biochem. Supp.*, (22):18-23, 1995.
Babbar et al., Cyclooxygenase-independent induction of apoptosis by sulindac sulfone is mediated by polyamines in colon cancer. *J. Biol. Chem.*, 278(48):47762-47775, 2003.
Babbar et al., Induction of spermidine/spermine N1-acetyltransferase (SSAT) by aspirin in Caco-2 colon cancer cells. *Biochemical Journal*, 394(Pt. 1):317-324, 2006.
Bailey et al., A randomized, double-blind, placebo-controlled phase 3 skin cancer prevention study of {alpha}-difluoromethylornithine in subjects with previous history of skin cancer. *Cancer Prev. Res. (Phila.)*, 3:35-47, 2010.
Balasubramanian et al., Targeting G-quadruplexes in gene promoters: a novel anticancer strategy? *Nat. Rev. Drug Discov.*, 10:261-275, 2011.
Balasundaram et al., Spermidine or spermine is essential for the aerobic growth of *Saccharomyces cerevisiae*. *Proc. Natl. Acad. Sci. USA*, 88:5872-5876, 1991.
Baral et al., Quadruplex-single nucleotide polymorphisms (Quad-SNP) influence gene expression difference among individuals. *Nucleic Acids Res.*, 40:3800-3811, 2012.
Baron et al., Calcium supplements for the prevention of colorectal adenomas. *The New England Journal of Medicine*, 340(2):101, 1999.
Barrett et al., Haploview: analysis and visualization of LD and haplotype maps. *Bioinformatics*, 21:263-265, 2005.
Barrett, Haploview: Visualization and analysis of SNP genotype data. *Cold Spring Harb. Protoc.*, 2009:pdb.ip71, 2009.
Barry et al., Variants downstream of the ornithine decarboxylase gene influence risk of colorectal adenoma and aspirin chemoprevention. *Cancer Prev. Res. (Phila.)*, 4:2072-2082, 2011.
Barry et al., Ornithine decarboxylase polymorphism modification of response to aspirin treatment for colorectal adenoma prevention. *J. Natl. Cancer Inst.*, 98(20):1494-1500, 2006.
Basuroy and Gerner, Emerging concepts in targeting the polyamine metabolic pathway in epithelial cancer chemoprevention and chemotherapy. *Journal of Biochemistry*, 139:27-33, 2006.
Bedi et al., *Cancer Res.*, 55(9):1811-1816, 1995.
Bello-Fernandez et al., The ornithine decarboxylase gene is a transcriptional target of c-Myc. *Proc. Natl. Acad. Sci. USA*, 90:7804, 1993.
Blackburn et al., Unprecedented opportunities and promise for cancer prevention research. *Cancer Prev. Res. (Phila.)*, 3(4):394-402, 2010.
Bochman et al., DNA secondary structures: stability and function of G-quadruplex structures. *Nat. Rev. Genet.*, 13:770-780, 2012.
Boland and Goel, Microsatellite instability in colorectal cancer. *Gastroenterology*, 138(6):2073-2087.e3, 2010.
Boland et al., Promoter methylation in the genesis of gastrointestinal cancer. *Yonsei Med. J.*, 50(3):309-321, 2009.
Boyd and Farnham, Identification of target genes of oncogenic transcription factors. *Proc. Soc. Exp. Biol. Med.*, 222(1):9-28, 1999.
Brooks, Side-effects of non-steroidal anti-inflammatory drugs. *Medical Journal of Australia*, 148:248-251, 1988.
Brooks et al., Making sense of G-quadruplex and i-motif functions in oncogene promoters. *FEBS J.*, 277:3459-3469, 2010.
Campello et al., Detection of SV40 in colon cancer: a molecular case-control study from northeast Italy. *J. Med. Virol.*, 82(7):1197-1200, 2010.
Casero and Marton, Targeting polyamine metabolism and function in cancer and other hyperproliferative diseases. *Nat. Rev. Drug Discov.*, 6:373-390, 2007.
Chan and Giovannucci, Primary prevention of colorectal cancer. *Gastroenterology*, 138(6):2029-2043.e10, 2010.
Cheng et al., CpG island methylator phenotype associates with low-degree chromosomal abnormalities in colorectal cancer. *Clin. Cancer Res.*, 14(19):6005-6013, 2008.
Childs et al., Polyamine-dependent gene expression. *Cell. Mol. Life Sci.*, 60:1394-1406, 2003.
Courey and Tjian, Analysis of Sp1 in vivo reveals multiple transcriptional domains, including a novel glutamine-rich activation motif. *Cell*, 55(5):887-898, 1988.
Davie et al., Nuclear organization and chromatin dynamics—Sp1, Sp3 and histone deacetylases. *Adv. Enzyme Regul.*, 48:189-208, 2008.
Dhakal et al., Intramolecular folding in human ILPR fragment with three C-rich repeats. *PLoS ONE*, 7(6):e39271, 2012.
Du et al., Genome-wide analysis reveals regulatory role of G4 DNA in gene transcription. *Genome Res.*, 18:233-241, 2008.
DuBois et al., *Cancer Res.*, 56:733-737, 1996.
Eddy and Maizels, Conserved elements with potential to form polymorphic G-quadruplex structures in the first intron of human genes. *Nucleic Acids Res.*, 36:1321-1333, 2008.
Erdman et al., APC-dependent changes in expression of genes influencing polyamine metabolism, and consequences for gastrointestinal carcinogenesis, in the Min mouse. *Carcinogenesis*, 20(9):1709, 1999.
Farre et al., Identification of patterns in biological sequences at the ALGGEN server: PROMO and MALGEN. *Nucleic Acids Res.*, 31:3651-3653, 2003.
Fearon, Molecular genetics of colorectal cancer. *Annu. Rev. Pathol.*, 6:479-507, 2011.
Fearon and Vogelstein, A genetic model for colorectal tumorigenesis. *Cell*, 61(5):759-767, 1990.
Feith et al., Tumor suppressor activity of ODC antizyme in MEK-driven skin tumorigenesis. *Carcinogenesis*, 27(5):1090-1098, 2006.
Feith et al., Targeted antizyme expression in the skin of transgenic mice reduces tumor promoter induction of ornithine decarboxylase and decreases sensitivity to chemical carcinogenesis. *Cancer Research*, 61(16):6073-6081, 2001.
Fenoglio and Lane, The anatomical precursor of colorectal carcinoma. *Cancer*, 34(S3):819-823, 1974.
Fodde, The APC gene in colorectal cancer. *Eur. J. Cancer*, 38(7):867-871, 2002.
Fultz and Gerner, APC-dependent regulation of ornithine decarboxylase in human colon tumor cells. *Molecular Carcinogenesis*, 34:10-18, 2002.
Gabriel et al., The structure of haplotype blocks in the human genome. *Science*, 296:2225-2229, 2002.
Gabriel et al., SNP genotyping using the Sequenom MassARRAY iPLEX platform. *Curr. Protoc. Hum. Genet.*, Chapter 2: Unit 2.12, 2009.
Gazdar et al., SV40 and human tumours: myth, association or causality? *Nat. Rev. Cancer*, 2(12):957-964, 2002.
Gendra et al., A sequence motif in the simian virus 40 (SV40) early core promoter affects alternative splicing of transcribed mRNA. *J. Biol. Chem.*, 282(16):11648-11657, 2007.
George et al., Identification of an X-linked locus modifying mouse skin tumor susceptibility. *Mol. Carcinog.*, 44(3):212-218, 2005.

Georgiades et al., Heterogeneity studies identify a subset of sporadic colorectal cancers without evidence for chromosomal or microsatellite instability. *Oncogene*, 18(56): 7933-7940, 1999.

Gerner and Meyskens, Polyamines and cancer: old molecules, new understanding. *Nature Reviews Cancer*, 4:781-792, 2004.

Gerner et al., A comprehensive strategy to combat colon cancer targeting the adenomatous polyposis coli tumor suppressor gene. *Annals of the New York Academy of Sciences*, 1059:97-105, 2005.

Gerner et al., Preclinical models for chemoprevention of colon cancer. *Recent Results in Cancer Research*, 163: 58-71; discussion:264-266, 2003.

Giardiello, Genetic testing in hereditary colorectal cancer. *JAMA*, 278:1278-1281, 1997.

Gjoerup and Chang, Update on human polyomaviruses and cancer. *Adv. Cancer Res.*, 106:1-51, 2010.

Groden et al., Identification and characterization of the familial adenomatous polyposis coli gene. *Cell*, 66:589-600, 1991.

Guo et al., Functional analysis of human ornithine decarboxylase alleles. *Cancer Research*, 60:6314, 2000.

Guo et al., Haploinsufficiency for odc modifies mouse skin tumor susceptibility. *Cancer Research*, 65(4):1146-1149, 2005.

Halder et al., Guanine quadruplex DNA structure restricts methylation of CpG dinucleotides genome-wide. *Mol. Biosyst.*, 6:2439-2447, 2010.

Hanahan and Weinberg, Hallmarks of cancer: the next generation. *Cell*, 144:646-674, 2011.

Hanahan and Weinberg, The hallmarks of cancer. *Cell*, 100:57-70, 2000.

Hanif et al., *Biochemical Pharmacology*, 52:237-245, 1996.

Hayes et al., Elevated levels of ornithine decarboxylase cooperate with Raf/ERK activation to convert normal keratinocytes into invasive malignant cells. *Oncogene*, 25(10):1543-1553, 2006.

He et al., Identification of c-MYC as a target of the APC pathway. *Science*, 281:1509, 1998.

Herman et al., Incidence and functional consequences of hMLH1 promoter hypermethylation in colorectal carcinoma. *Proc. Natl. Acad. Sci. USA*, 95:6870-6875, 1998.

Hermeking, The MYC oncogene as a cancer drug target. *Current Cancer Drug Targets*, 3:163-175, 2003.

Hickok et al., Complete amino acid sequence of human ornithine decarboxylase deduced from complementary DNA. *DNA*, 6(3):179-187, 1987.

Hubner et al., Ornithine decarboxylase G316A genotype is prognostic for colorectal adenoma recurrence and predicts efficacy of aspirin chemoprevention. *Clinical Cancer Research*, 14(8):2303, 2008.

Hughes et al., Ornithine Decarboxylase G316A Genotype and Colorectal Cancer Risk. *Colorectal Dis.*, 2010.

Huppert and Balasubramanian, Prevalence of quadruplexes in the human genome. *Nucleic Acids Res.*, 33:2908-2916, 2005.

Huppert, Hunting G-quadruplexes. *Biochimie*, 90:1140-1148, 2008.

Huppert, Four-stranded nucleic acids: structure, function and targeting of G-quadruplexes. *Chem. Soc. Rev.*, 37:1375-1384, 2008.

Igarashi and Kashiwagi, Polyamines: mysterious modulators of cellular functions. *Biochem. Biophys. Res. Commun.*, 271:559-564, 2000.

Ignatenko et al., Role of c-Myc in intestinal tumorigenesis of the ApcMin/+ mouse. *Cancer Biol. Ther.*, 5(12):1658-1664, 2006.

Ignatenko et al., Combination chemoprevention of intestinal carcinogenesis in a murine model of familial adenomatous polyposis. *Nutr. Cancer*, 60(Suppl. 1):30-35, 2008.

Imperiale et al., Five-year risk of colorectal neoplasia after negative screening colonoscopy. *N. Engl. J. Med.*, 359 (12):1218-1224, 2008.

Issa, Colon cancer: it's CIN or CIMP. *Clin. Cancer Res.*, 14(19):5939-5940, 2008.

Iwamoto et al., Expression of beta-catenin and full-length APC protein in normal and neoplastic colonic tissues. *Carcinogenesis*, 21(11):1935-1940, 2000.

Janne et al., Genetic approaches to the cellular functions of polyamines in mammals. *European Journal of Biochemistry*, 271:877-894, 2004.

Kern et al., Identification of p53 as a sequence-specific DNA-binding protein. *Science*, 252:1708-1711, 1991.

Kinzler et al., Identification of FAP locus genes from chromosome 5q21. *Science*, 253(5020):661-665, 1991.

Kronborg and Fenger, Clinical evidence for the adenoma-carcinoma sequence. *European Journal of Cancer Prevention*, 8(6): S87, 1999.

Kumar et al., Elevated polyamines induce c-MYC overexpression by perturbing quadruplex-WC duplex equilibrium. *Nucleic Acids Res.*, 37:3321-3331, 2009.

Kumar et al., Regulation of rat ornithine decarboxylase promoter activity by binding of transcription factor Sp1. *J. Biol. Chem.*, 270:4341-4348, 1995.

Kumar and Butler, Transcription factor Sp3 antagonizes activation of the ornithine decarboxylase promoter by Sp1. *Nucleic Acids Res.*, 25:2012-2019, 1997.

Kurian et al., Polyamine sensing by nascent ornithine decarboxylase antizyme stimulates decoding of its mRNA. *Nature*, 477:490-494, 2011.

Kypr et al., *Nucleic Acids Res.*, 37:1713-1725, 2009.

Lam et al., G-quadruplex structures are stable and detectable in human genomic DNA. *Nat. Commun.*, 4:1796, 2013.

Larque et al., Biological significance of dietary polyamines. *Nutrition*, 23(1):87-95, 2007.

Levin et al., Screening and surveillance for the early detection of colorectal cancer and adenomatous polyps, 2008: a joint guideline from the American Cancer Society, the US Multi-Society Task Force on Colorectal Cancer, and the American College of Radiology. *Gastroenterology*, 134(5):1570-1595, 2008.

Li and Davie, The role of Sp1 and Sp3 in normal and cancer cell biology. Ann. Anat., 192:275-283, 2010.

Li et al., Gene regulation by Sp1 and Sp3. *Biochem. Cell. Biol.*, 82:460-471, 2004.

Lieberman et al., Five-year colon surveillance after screening colonoscopy. *Gastroenterology*, 133(4):1077-1085, 2007.

Lippman, *Nat. Clin. Pract. Oncol.*, 3(10):523, 2006.

Love et al., *J. Natl. Cancer Inst.*, 85:732-737, 1993.

Luk and Baylin, Ornithine decarboxylase as a biologic marker in familial colonic polyposis. *N. Engl. J. Med.*, 311(2):80-83, 1984.

Lupulescu, *Cancer Detect. Prev.*, 20(6):634-637, 1996.

Lux et al., Ornithine decarboxylase is important in intestinal mucosal maturation and recovery from injury in rats. *Science*, 210:195-198, 1980.

Maginnis and Atwood, J C virus: an oncogenic virus in animals and humans? *Semin. Cancer Biol.*, 19(4):261-269, 2009.

Martinez et al., Pronounced reduction in adenoma recurrence associated with aspirin use and a polymorphism in the ornithine decarboxylase gene. *Proc. Natl. Acad. Sci. USA*, 100:7859, 2003.

Martinez et al., Adenoma characteristics as risk factors for recurrence of advanced adenomas. *Gastroenterology*, 120(5):1077-1083, 2001.

Martinez et al., A pooled analysis of advanced colorectal neoplasia diagnoses after colonoscopic polypectomy. *Gastroenterology*, 136(3):832-841, 2009.

Matsufuji et al., Autoregulatory frameshifting in decoding mammalian ornithine decarboxylase antizyme. *Cell*, 80:51-60, 1995.

Matsuoka et al., hnRNP U interacts with the c-Myc-Max complex on the E-box promoter region inducing the ornithine decarboxylase gene. *Oncol. Rep.*, 22:249-255, 2009.

McCormack and Johnson, Polyamines and cell migration. *J. Physiol. Pharmacol.*, 52:327-349, 2001.

McLaren et al., *Cancer Prev. Res.*, 1(7):514-521, 2008.

Messeguer et al., PROMO: detection of known transcription regulatory elements using species-tailored searches. *Bioinformatics*, 18:333-334, 2002.

Meyskens et al., Difluoromethylornithine Plus Sulindac for the Prevention of Sporadic Colorectal Adenomas: A Randomized Placebo-Controlled, Double-Blind Trial. *Cancer Prevention Research*, 1:32-38, 2008.

Mishra et al., The role of TGF- and Wnt signaling in gastrointestinal stem cells and cancer. *Oncogene*, 24:5775-5789, 2005.

Morson, Evolution of cancer of the colon and rectum. *Cancer*, 34(53):845-849, 1974.

Moser et al., A dominant mutation that predisposes to multiple intestinal neoplasia in the mouse. *Science*, 247:322-324, 1990.

Moshier et al., Isolation and expression of a human ornithine decarboxylase gene. *J. Biol. Chem.*, 265(9):4884-4892, 1990.

Narisawa et al., *Cancer Res.*, 41(5):1954-1957, 1981.

Nilsson et al., Mnt loss triggers Myc transcription targets, proliferation, apoptosis, and transformation. *Molecular and Cellular Biology*, 24:1560, 2004.

Oshima et al., Suppression of intestinal polyposis in Apc delta716 knockout mice by inhibition of cyclooxygenase 2 (COX-2). *Cell*, 87(5):803-809, 1996.

Paz et al., Polyamines are oncometabolites that regulate the LIN28/let-7 pathway in colorectal cancer cells. *Mol. Carcinog.*, 53(Suppl. 1): E96-106, 2014.

Paz et al., *Polyamines in cancer. Adv. Clin. Chem.*, 54:45-70, 2011.

Pegg, Regulation of ornithine decarboxylase. *J. Biol. Chem.*, 281:14529, 2006.

Pegg, Polyamine metabolism and its importance in neoplastic growth and a target for chemotherapy. *Cancer Research*, 48:759-774, 1988.

Pegg, Mammalian polyamine metabolism and function. *IUBMB Life*, 61:880-894, 2009.

Pena et al., Regulation of human ornithine decarboxylase expression by the c-Myc. Max protein complex. *J. Biol. Chem.*, 268:27277, 1993.

Pendeville et al., The ornithine decarboxylase gene is essential for cell survival during early murine development. *Mol. Cell. Biol.*, 21(19):6549-6558, 2001.

Physician's Desk Reference, Medical Economics Data, Montville, N.J., 1745-1747, 1999.

Piazza et al., *Cancer Res.*, (55):3110-3116, 1995.

Piazza et al., *Cancer Res.*, (57):2452-2459, 1997a.

Piazza et al., *Cancer Res.*, (57):2909-2915, 1997b.

Pipas, SV40: *Cell* transformation and tumorigenesis. Virology, 384(2):294-303, 2009.

Psaty and Potter, *N. Engl. J. Med.*, 355(9):950-952, 2006.

Qin and Hurley, Structures, folding patterns, and functions of intramolecular DNA G-quadruplexes found in eukaryotic promoter regions. *Biochimie*, 90:1149-1171, 2009.

Raiber et al., A non-canonical DNA structure is a binding motif for the transcription factor SP1 in vitro. *Nucleic Acids Res.*, 40:1499-1508, 2012.

Raj et al., Role of dietary polyamines in a phase III clinical trial of difluoromethylornithine (DFMO) and sulindac for prevention of sporadic colorectal adenomas. *Br. J. Cancer*, 108:512-518, 2013.

Rao et al., *Cancer Res.*, (55):1464-1472, 1995.

Reddy et al., *Cancer Res.*, (50):2562-2568, 1990.

Reya and Clevers, Wnt signalling in stem cells and cancer. *Nature*, 434:843-850, 2005.

Ricci et al., Direct repression of FLIP expression by c-myc is a major determinant of TRAIL sensitivity. *Mol. Cell Biol.*, 24:8541-8555, 2004.

Rounbehler et al., Targeting ornithine decarboxylase impairs development of MYCN-amplified neuroblastoma. *Cancer Res.*, 69(2):547-553, 2009.

Russell and Snyder, Amine synthesis in rapidly growing tissues: ornithine decarboxylase activity in regenerating rat liver, chick embryo, and various tumors. *Proc. Natl. Acad. Sci. USA*, 60(4):1420-1427, 1968.

Sapetschnig et al., Complexity of translationally controlled transcription factor Sp3 isoform expression. *J. Biol. Chem.*, 279:42095-42105, 2004.

Sen and Gilbert, A sodium-potassium switch in the formation of four-stranded G4-DNA. *Nature*, 344:410-414, 1990.

Shantz and Levin, Regulation of ornithine decarboxylase during oncogenic transformation: mechanisms and therapeutic potential. *Amino Acids*, 33(2):213-223, 2007.

Siegel et al., Cancer statistics, 2013. *CA Cancer J. Clin.*, 63(1):11-30, 2013.

Simoneau et al., Alpha-difluoromethylornithine and polyamine levels in the human prostate: results of a phase IIa trial. *J Natl. Cancer Inst.*, 93(1):57-59, 2001.

Simoneau et al., The effect of difluoromethylornithine on decreasing prostate size and polyamines in men: results of a year-long phase IIb randomized placebo-controlled chemoprevention trial. *Cancer Epidemiol Biomarkers Prev.*, 17(2):292-299, 2008.

Singh and Reddy, *Annals. NY Acad. Sci.*, 768:205-209, 1995.

Singh et al., *Carcinogenesis*, 15:1317-1323, 1994.

Sporn and Hong, Clinical Prevention of Recurrence of Colorectal Adenomas by the Combination of Difluoromethylornithine and Sulindac: An Important Milestone. *Cancer Prevention Research*, 1:9, 2008.

Stephens et al., A new statistical method for haplotype reconstruction from population data. *Am. J Hum. Genet.*, 68:978-989, 2001.

Stephens and Donnelly, A comparison of bayesian methods for haplotype reconstruction from population genotype data. *Am. J. Hum. Genet.*, 73:1162-1169, 2003.

Stewart et al., A population-based study of colorectal cancer histology in the United States, 1998-2001. *Cancer*, 107 (Suppl. 5):1128-1141, 2006.

Tabor et al., Construction of an *Escherichia coli* strain unable to synthesize putrescine, spermidine, or cadaverine: characterization of two genes controlling lysine decarboxylase. *J. Bacteriol.*, 144:952-956, 1980.

Tang et al., Ornithine decarboxylase is a target for chemoprevention of basal and squamous cell carcinomas in Ptch1+/−mice. *J. Clin. Invest.*, 113(6):867-875, 2004.

Thomas and Thomas, Polyamines in cell growth and cell death: molecular mechanisms and therapeutic applications. *Cell. Mol. Life Sci.*, 58:244-258, 2001.

Thompson et al., *J. Natl. Cancer Inst.*, (87):1259-1260, 1995.

Thompson and Gerner, Current concepts in colorectal cancer prevention. *Expert Review of Gastroenterology and Hepatology*, 3(4):369-382, 2009.

Todd and Neidle, The relationship of potential G-quadruplex sequences in cis-upstream regions of the human genome to SP1-binding elements. *Nucleic Acids Res.*, 36:2700-2704, 2008.

Toyota et al., CpG island methylator phenotype in colorectal cancer. *Proc. Natl. Acad. Sci. USA*, 96:8681-8686, 1999.

Uemura et al., Polyamine transport is mediated by both endocytic and solute carrier transport mechanisms in the gastrointestinal tract. *Am. J. Physiol. Gastrointest. Liver Physiol.*, 299(2): G517-22, 2010.

Uemura et al., Identification and characterization of a diamine exporter in colon epithelial cells. *J. Biol. Chem.*, 283(39):26428-26435, 2008.

Vane and Botting, *Adv. Exp. Med. Biol.*, 433:131-138, 1997.

Vargas et al., Dietary polyamine intake and risk of colorectal adenomatous polyps. *Am. J. Clin. Nutr.*, 96(1):133-141, 2012.

Walhout et al., Sequences flanking the E-box contribute to cooperative binding by c-Myc/Max heterodimers to adjacent binding sites. *Biochimica et Biophysica Acta (BBA)-Gene Structure and Expression*, 1397:189-201, 1998.

Walhout et al., c-Myc/Max heterodimers bind cooperatively to the E-box sequences located in the first intron of the rat ornithine decarboxylase (ODC) gene. *Nucleic Acids Research*, 25:1493, 1997.

Wasylyk et al., The SV40 72 bp repeat preferentially potentiates transcription starting from proximal natural or substitute promoter elements. *Cell*, 32(2):503-514, 1983.

Weinstein and Joe, Oncogene addiction. *Cancer Res.*, 68(9): 3077-3080; discussion: 3080, 2008.

Winawer et al., Prevention of colorectal cancer by colonoscopic polypectomy. *N. Engl. J. Med.*, 329:1977-1981, 1993.

Winawer et al., Guidelines for colonoscopy surveillance after polypectomy: a consensus update by the US Multi-Society Task Force on Colorectal Cancer and the American Cancer Society. *Gastroenterology*, 130(6):1872-1885, 2006.

Xie et al., Loss of intracellular putrescine pool-size regulation induces apoptosis. *Exp. Cell Res.*, 230(2):386-392, 1997.

Yu et al., Stability of the Sp3-DNA complex is promoter-specific: Sp3 efficiently competes with Sp1 for binding to promoters containing multiple Sp-sites. *Nucleic Acids Res.*, 31:5368-5376, 2003.

Zell et al., Meat consumption, ornithine decarboxylase gene polymorphism, and outcomes after colorectal cancer diagnosis. *J. Carcinog.*, 11:17, 2012.

Zell et al., Risk and risk reduction involving arginine intake and meat consumption in colorectal tumorigenesis and survival. *Int. J. Cancer*, 120(3):459-468, 2007.

Zell et al., Associations of a polymorphism in the ornithine decarboxylase gene with colorectal cancer survival. *Clinical Cancer Research*, 15:6208, 2009.

Zell et al., Ornithine decarboxylase-1 polymorphism, chemoprevention with eflornithine and sulindac, and outcomes among colorectal adenoma patients. *J. Natl. Cancer. Inst.*, 102:1513-1516, 2010.

What is claimed is:

1. A method for preventing recurrence of or treating colorectal carcinoma in a patient in need thereof, the method comprising administering to the patient effective amounts of a pharmaceutical therapy comprising:
    (i) a first agent that inhibits ornithine decarboxylase (ODC) within the patient, wherein the first agent is α-difluoromethylornithine (DFMO); and
    (ii) a second agent that modulates the polyamine pathway to reduce overall polyamine content within the patient when combined with the first agent, wherein the second agent is sulindac,
wherein the patient's genotype at rs2302616 of both alleles of the ODC1 gene is T/T.

2. The method of claim 1, wherein the patient's genotype at rs2302616 of both alleles of the ODC1 gene is obtained by receiving a report containing said genotype, taking a patient history that reveals said genotype, or testing the patient's genotype at rs2302616 of both ODC1 alleles.

3. The method of claim 1, wherein the patient's genotype at rs2302615 of at least one allele of the ODC1 gene is G.

4. The method of claim 1, wherein the method prevents the formation of new aberrant crypt foci, new adenomatous polyps or new adenomas with dysplasia in the patient.

5. The method of claim 1, wherein the method prevents the development or recurrence of a colorectal carcinoma in a patient at risk therefor.

6. The method of claim 1, wherein the method prevents ototoxicity or the risk thereof within the patient.

7. The method of claim 1, wherein the patient has been identified as having one or more advanced colorectal neoplasms or as having one or more adenomatous polyps in the colon, rectum or appendix.

8. The method of claim 1, wherein the patient has been diagnosed with familial adenomatous polyposis, Lynch syndrome, or familial colorectal cancer type X.

9. The method of claim 1, wherein the patient is human.

10. A method for preventing recurrence of or treating colorectal carcinoma in a patient in need thereof, the method comprising:
   a) detecting whether the patient's genotype at rs2302616 of both alleles of an ODC1 gene is T/T by:
      (i) obtaining or having obtained a biological sample from the patient; and
      (ii) performing or having performed a genotyping assay on the biological sample to determine if the patient has a T/T genotype at rs2302616 of both alleles of the ODC1 gene; and
   b) selecting or having selected the patient for treatment when a T/T genotype at rs2302616 of both alleles of the ODC1 gene is detected; and
   c) administering or having administered to the selected patient effective amounts of a pharmaceutical therapy comprising:
      (i) a first agent that inhibits ornithine decarboxylase (ODC) within the patient, wherein the first agent is α-difluoromethylornithine (DFMO); and
      (ii) a second agent that modulates the polyamine pathway to reduce overall polyamine content within the patient when combined with the first agent, wherein the second agent is sulindac.

11. The method of claim 3, wherein the patient's genotype at rs2302615 of at least one allele of the ODC1 gene is obtained by receiving a report containing said genotype, taking a patient history that reveals said genotype, or testing the patient's genotype at rs2302615 of at least one ODC1 allele.

12. The method of claim 3, wherein the patient's genotype at rs2302615 of one allele of the ODC1 gene is determined.

13. The method of claim 3, wherein the patient's genotype at rs2302615 of both alleles of the ODC1 gene is determined.

14. The method of claim 13, wherein the patient's genotype at rs2302615 of both alleles of the ODC1 gene is G/G or G/A.

15. The method of claim 14, wherein the patient's genotype at rs2302615 of both alleles of the ODC1 gene is G/G.

* * * * *